(12) United States Patent
Wang et al.

(10) Patent No.: US 11,739,375 B2
(45) Date of Patent: *Aug. 29, 2023

(54) DIGITAL AMPLIFICATION WITH PRIMERS OF LIMITED NUCLEOTIDE COMPOSITION

(71) Applicant: ATILA BIOSYSTEMS INCORPORATED, Palo Alto, CA (US)

(72) Inventors: Youxiang Wang, Palo Alto, CA (US); Zhijie Yang, Palo Alto, CA (US); Xin Chen, Palo Alto, CA (US); Yu Zhao, Palo Alto, CA (US); Rong Wang, Palo Alto, CA (US)

(73) Assignee: ATILA BIOSYSTEMS INCORPORATED, Palo Alto, CA (US)

( * ) Notice: Subject to any disclaimer, the term of this patent is extended or adjusted under 35 U.S.C. 154(b) by 278 days.

This patent is subject to a terminal disclaimer.

(21) Appl. No.: 16/638,346

(22) PCT Filed: Aug. 10, 2018

(86) PCT No.: PCT/US2018/046360
§ 371 (c)(1),
(2) Date: Feb. 11, 2020

(87) PCT Pub. No.: WO2019/033065
PCT Pub. Date: Feb. 14, 2019

(65) Prior Publication Data
US 2020/0165668 A1      May 28, 2020

Related U.S. Application Data

(60) Provisional application No. 62/544,605, filed on Aug. 11, 2017.

(51) Int. Cl.
*C12Q 1/6858* (2018.01)
*C12Q 1/6853* (2018.01)

(52) U.S. Cl.
CPC ......... *C12Q 1/6858* (2013.01); *C12Q 1/6853* (2013.01); *C12Q 2523/125* (2013.01);
(Continued)

(58) Field of Classification Search
CPC ................ C12Q 1/6844; C12Q 1/6853; C12Q 2523/125; C12Q 2537/16; C12Q 2525/185; C12Q 2563/159
See application file for complete search history.

(56) References Cited

U.S. PATENT DOCUMENTS

| 11,091,799 B2 | 8/2021 | Wang et al. |
| 2006/0014167 A1 | 1/2006 | Church et al. |

(Continued)

FOREIGN PATENT DOCUMENTS

| JP | 2006519621 A | 8/2006 |
| JP | 2010539971 A | 12/2010 |

(Continued)

OTHER PUBLICATIONS

Hindson et al. Analytical Chemistry 2011; 83: 8604-8610. (Year: 2011).*

(Continued)

*Primary Examiner* — Angela M. Bertagna
(74) *Attorney, Agent, or Firm* — Alston & Bird LLP

(57) ABSTRACT

The invention provides methods of digital amplification using primers of limited nucleotide composition. Limited nucleotide composition means that the primers are underrepresented in at least one nucleotide type. Such primers have much reduced capacity to prime from each other or to (Continued)

extend initiated by mispriming from other than at their intended primer binding sites in a target nucleic acid.

33 Claims, 10 Drawing Sheets

Specification includes a Sequence Listing.

(52) U.S. Cl.
CPC ... *C12Q 2525/185* (2013.01); *C12Q 2537/16* (2013.01); *C12Q 2563/159* (2013.01)

(56) References Cited

U.S. PATENT DOCUMENTS

| | | | |
|---|---|---|---|
| 2007/0178453 | A1 | 8/2007 | Rujan et al. |
| 2007/0202525 | A1* | 8/2007 | Quake .................. C12Q 1/6858 435/6.12 |
| 2009/0036315 | A1 | 2/2009 | Labgold et al. |
| 2010/0035303 | A1 | 2/2010 | Rhee |
| 2011/0294129 | A1 | 12/2011 | Ali et al. |
| 2013/0115595 | A1 | 5/2013 | Hantash et al. |
| 2014/0065613 | A1 | 3/2014 | Bormann Chung et al. |
| 2014/0228254 | A1 | 8/2014 | Adessi et al. |
| 2014/0274811 | A1 | 9/2014 | Arnold |
| 2015/0232929 | A1 | 8/2015 | Stephens et al. |
| 2016/0208322 | A1 | 7/2016 | Anderson et al. |
| 2018/0148775 | A1 | 5/2018 | Wang et al. |

FOREIGN PATENT DOCUMENTS

| | | |
|---|---|---|
| JP | 2014-521337 A | 8/2014 |
| JP | 2015-500013 A | 1/2015 |
| WO | WO 06/058393 | 6/2006 |
| WO | WO 2007/092473 A2 | 8/2007 |
| WO | WO 2010/021702 A1 | 2/2010 |
| WO | WO 2014/201254 A1 | 12/2014 |
| WO | WO 2016/046183 A1 | 3/2016 |
| WO | WO 16/172632 A2 | 10/2016 |
| WO | WO 19/033065 A1 | 2/2019 |

OTHER PUBLICATIONS

Pallisgaard et al. Clinica Chimica Acta 2015; 446: 141-146. (Year: 2015).*

McDermott et al. Analytical Chemistry 2013; 85: 11619-11627. (Year: 2013).*

Hayashi et al. Cancer Prevention Research 2015; 8: 1017-1026. (Year: 2015).*

McDermott et al. Analytical Chemistry 2013; 85: 11619-11627 + Supporting Information. (Year: 2013).*

Mazaika, et al., "Digital Droplet PCR: CNV analysis and Other Applications," Curr Protoc Hum Genet., 82: 7.24.1-7.24.13, (Jul. 2015).

Ono, et al., "An improved digital polymerase chain reaction protocol to capture low-copy KRAS mutations in plasma cell-free DNA by resolving 'subsampling' issues," Molecular Oncology, 11, 1448-1458, (2017).

Suzawa, et al., "Optimal method for quantitative detection of plasma EGFR T790M mutation using droplet digital PCR system," Oncology Reports, 37:3100-3106, (2017).

EP 18844988.8 Extended European Search Report dated Apr. 13, 2021.

Braun et al., "Detecting CFTR Gene Mutations by Using Primer Oligo Base Extension and Mass Spectrometry," Clinical Chemistry, 43(7): 1151-1158, (1997).

Tyagi et al., "Molecular Beacons: Probes that Fluoresce upon Hybridization," Nature Biotechnology, 14:303-308, (1996).

Van Harmelen et al., "Increased Adipose Angiotensinogen Gene Expression in Human Obesity" Obesity Research, 8(4):337-341, (2000).

Vet et al., "Design and Optimization of Molecular Beacon Real-Time Polymerase Chain Reaction Assays," Methods in Molecular Biology, 288:273-288, (2005).

Yao et al., "Purification and Characterization of a Novel Deoxyinosine-specific Enzyme, Deoxyinosine 3' Endonuclease, from *Escherichia coli*," The Journal of Biological Chemistry, 269(23):16260-16268, (1994).

Zeng et al., "Array-MLPA: comprehensive detection of deletions and duplications and its application to DMD patients," Human Mutation, 29(1): 190-197, doi: 10.1002/humu.20613, (2008).

EP Application No. 16784032.1 (Published as EP3286338), Supplementary European Search Report and European Search Opinion dated Nov. 16, 2018.

U.S. Appl. No. 15/569,080, Non-Finai Office Action dated Dec. 11, 2019.

U.S. Appl. No. 15/569,080, Requirement for Restriction/Election dated Jun. 27, 2019.

WIPO Application No. PCT/US2016/029054, PCT International Preliminary Report on Patentability dated Nov. 2, 2017.

WIPO Application No. PCT/US2016/029054, PCT International Search Report and Written Opinion of the International Searching Authority dated Dec. 1, 2016.

WIPO Application No. PCT/US2018/046360, PCT International Preliminary Report on Patentability dated Feb. 11, 2020.

WIPO Application No. PCT/US2018/046360, PCT International Search Report and Written Opinion of the International Searching Authority dated Oct. 17, 2018.

* cited by examiner

Fig. 2

Mismatch three nucleotides primers

```
                                                    Reverse primer, 3dNTP, 2 mismatch with template
                                                    cctaaccataacCtccaataattattaCtacct  3'
5' ctccatacccaGtatcaatGatatcaGcatcctcgtaggagcctaaccataacGtccaataattattaGcacct  Template
3' gaggtatgggtCatagttaCtatagtCgtaggagcctaaccataacGtccaataattattaGcacct  5'
   ctccatacccaCtatcaatCatatcaCcatcctc
Forward primer, 3dNTP, 3 mismatch with template ctccatacccaCtatcaatCatatcaCcatcctc
   gaggtatgggtCatagttaCtatagtCgtaggagcctaaccataacGtccaataattattaGcacct
                                                                              ↑
                                                                              ┆
                                                                              ┆
                                                                              ↓
   ctccatacccaGtatcaatGatatcaGcatcctcgtaggagcctaaccataacGtccaataattattaGcacct
                                                    cctaaccataacCtccaataattattaCcacct
```

Fig. 3
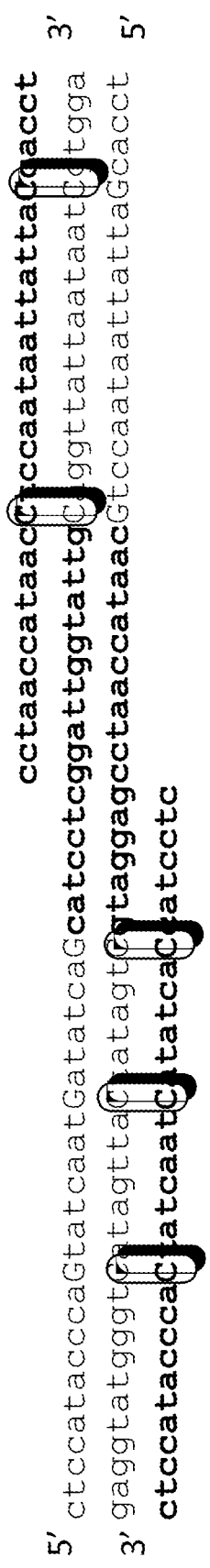
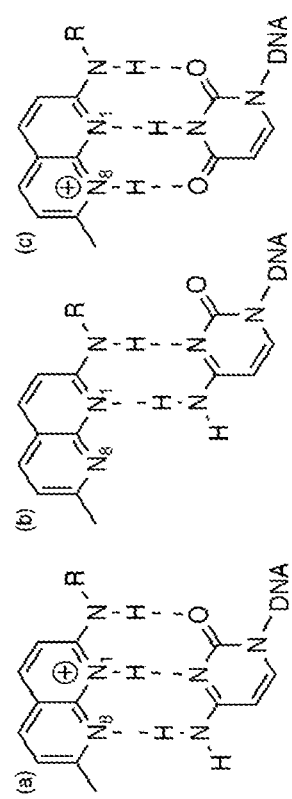

Three nucleotides primer amplify 4 Nucleotide Regions with four nucleotides dNTPs

SEQUENCE LISTING

<160> NUMBER OF SEQ ID NOS: 87

<210> SEQ ID NO 1
<211> LENGTH: 36
<212> TYPE: DNA
<213> ORGANISM: Artificial sequence
<220> FEATURE:
<223> OTHER INFORMATION: Synthesized

<400> SEQUENCE: 1
tttaatacct caatctctat cacaatatcc acattc   36

<210> SEQ ID NO 2
<211> LENGTH: 36
<212> TYPE: DNA
<213> ORGANISM: Artificial sequence
<220> FEATURE:
<223> OTHER INFORMATION: Synthesized

<400> SEQUENCE: 2
aacaacaata tctactcaat ctccacactc ccctac   36

<210> SEQ ID NO 3
<211> LENGTH: 36
<212> TYPE: DNA
<213> ORGANISM: Artificial sequence
<220> FEATURE:
<223> OTHER INFORMATION: Synthesized

<400> SEQUENCE: 3
tttaatacct caatgtgtat cacaatatcc acattc                36

<210> SEQ ID NO 4
<211> LENGTH: 36
<212> TYPE: DNA
<213> ORGANISM: Artificial sequence
<220> FEATURE:
<223> OTHER INFORMATION: Synthesized

<400> SEQUENCE: 4
aacaagaata tctactcaat ctccagactc ccctac                36

<210> SEQ ID NO 5
<211> LENGTH: 29
<212> TYPE: DNA
<213> ORGANISM: Artificial sequence
<220> FEATURE:
<223> OTHER INFORMATION: Synthesized

<400> SEQUENCE: 5
cccacactct tcttcaaggt tcaccttcc                29

<210> SEQ ID NO 6
<211> LENGTH: 27
<212> TYPE: DNA
<213> ORGANISM: Artificial sequence
<220> FEATURE:
<223> OTHER INFORMATION: Synthesized

<400> SEQUENCE: 6
gaccttcatc acctttgtt tcatctc                27

<210> SEQ ID NO 7
<211> LENGTH: 37
<212> TYPE: DNA
<213> ORGANISM: Artificial sequence
<220> FEATURE:
<223> OTHER INFORMATION: Synthesized

<400> SEQUENCE: 7
cctacttctg tcaattcatc agactcattc tccatcc                37

<210> SEQ ID NO 8
<211> LENGTH: 32
<212> TYPE: DNA
<213> ORGANISM: Artificial sequence
<220> FEATURE:
<223> OTHER INFORMATION: Synthesized

<400> SEQUENCE: 8
aacatctctt ccccaaagga tcacaactcc tc                32

<210> SEQ ID NO 9
<211> LENGTH: 29
<212> TYPE: DNA
<213> ORGANISM: Artificial sequence
<220> FEATURE:
<223> OTHER INFORMATION: Synthesized

<400> SEQUENCE: 9
ctcttgccta cacctgcatt taccccaac                29

```
<210> SEQ ID NO 10
<211> LENGTH: 27
<212> TYPE: DNA
<213> ORGANISM: Artificial sequence
<220> FEATURE:
<223> OTHER INFORMATION: Synthesized

<400> SEQUENCE: 10
tccacagctc ctgcttatat caaaacc                                        27

<210> SEQ ID NO 11
<211> LENGTH: 32
<212> TYPE: DNA
<213> ORGANISM: Artificial sequence
<220> FEATURE:
<223> OTHER INFORMATION: Synthesized

<400> SEQUENCE: 11
catacctcct tgtcttgaac cccaaacctt cc                                  32

<210> SEQ ID NO 12
<211> LENGTH: 31
<212> TYPE: DNA
<213> ORGANISM: Artificial sequence
<220> FEATURE:
<223> OTHER INFORMATION: Synthesized

<400> SEQUENCE: 12
aatcttctac cgatgccttt cttatttccc c                                   31

<210> SEQ ID NO 13
<211> LENGTH: 32
<212> TYPE: DNA
<213> ORGANISM: Artificial sequence
<220> FEATURE:
<223> OTHER INFORMATION: Synthesized

<400> SEQUENCE: 13
catacctcct tgtcttgaac cccaaacctt cc                                  32

<210> SEQ ID NO 14
<211> LENGTH: 31
<212> TYPE: DNA
<213> ORGANISM: Artificial sequence
<220> FEATURE:
<223> OTHER INFORMATION: Synthesized

<400> SEQUENCE: 14
aatcttctac cgatgccttt cttatttccc c                                   31

<210> SEQ ID NO 15
<211> LENGTH: 29
<212> TYPE: DNA
<213> ORGANISM: Artificial sequence
<220> FEATURE:
<223> OTHER INFORMATION: Synthesized

<400> SEQUENCE: 15
cccacactct tcttcaaggt tcaccttcc                                      29

<210> SEQ ID NO 16
<211> LENGTH: 27
<212> TYPE: DNA
<213> ORGANISM: Artificial sequence
<220> FEATURE:
<223> OTHER INFORMATION: Synthesized
```

<400> SEQUENCE: 16
gaccttcatc accttttgtt tcatctc                                    27

<210> SEQ ID NO 17
<211> LENGTH: 27
<212> TYPE: DNA
<213> ORGANISM: Artificial sequence
<220> FEATURE:
<223> OTHER INFORMATION: Synthesized

<400> SEQUENCE: 17
ctctcaaagt tttctgcctc aaattcc                                    27

<210> SEQ ID NO 18
<211> LENGTH: 33
<212> TYPE: DNA
<213> ORGANISM: Artificial sequence
<220> FEATURE:
<223> OTHER INFORMATION: Synthesized

<400> SEQUENCE: 18
tttcgaaacc ccctcattcc acgaaaaata ccc                             33

<210> SEQ ID NO 19
<211> LENGTH: 36
<212> TYPE: DNA
<213> ORGANISM: Artificial sequence
<220> FEATURE:
<223> OTHER INFORMATION: Synthesized

<400> SEQUENCE: 19
tgtcccccta aaattcatat gccaatctta acctcc                          36

<210> SEQ ID NO 20
<211> LENGTH: 45
<212> TYPE: DNA
<213> ORGANISM: Artificial sequence
<220> FEATURE:
<223> OTHER INFORMATION: Synthesized

<400> SEQUENCE: 20
tctccacccc catgacctaa tcacctccca aagttcccca ccttc                45

<210> SEQ ID NO 21
<211> LENGTH: 27
<212> TYPE: DNA
<213> ORGANISM: Artificial sequence
<220> FEATURE:
<223> OTHER INFORMATION: Synthesized

<400> SEQUENCE: 21
aacccttata accagagatc tttctcc                                    27

<210> SEQ ID NO 22
<211> LENGTH: 27
<212> TYPE: DNA
<213> ORGANISM: Artificial sequence
<220> FEATURE:
<223> OTHER INFORMATION: Synthesized

<400> SEQUENCE: 22
tcaagtccct ctcatgcttc taatcac                                    27

<210> SEQ ID NO 23
<211> LENGTH: 29
<212> TYPE: DNA
<213> ORGANISM: Artificial sequence
<220> FEATURE:
<223> OTHER INFORMATION: Synthesized

<400> SEQUENCE: 23
aacactccca tgattcagtt atctcccac                                    29

<210> SEQ ID NO 24
<211> LENGTH: 41
<212> TYPE: DNA
<213> ORGANISM: Artificial sequence
<220> FEATURE:
<223> OTHER INFORMATION: Synthesized

<400> SEQUENCE: 24
tcctcaccca aatctcctat tgtagcttcc ataattccca c                      41

<210> SEQ ID NO 25
<211> LENGTH: 37
<212> TYPE: DNA
<213> ORGANISM: Artificial sequence
<220> FEATURE:
<223> OTHER INFORMATION: Synthesized

<400> SEQUENCE: 25
tgtcctaacc caaatcccat cttgaatttt aatcccc                           37

<210> SEQ ID NO 26
<211> LENGTH: 33
<212> TYPE: DNA
<213> ORGANISM: Artificial sequence
<220> FEATURE:
<223> OTHER INFORMATION: Synthesized

<400> SEQUENCE: 26
gaaactactc ccatgattca attacctcct acc                               33

<210> SEQ ID NO 27
<211> LENGTH: 23
<212> TYPE: DNA
<213> ORGANISM: Artificial sequence
<220> FEATURE:
<223> OTHER INFORMATION: Synthesized

<400> SEQUENCE: 27
tttgaaagta ttccctcctc ctc                                          23

<210> SEQ ID NO 28
<211> LENGTH: 24
<212> TYPE: DNA
<213> ORGANISM: Artificial sequence
<220> FEATURE:
<223> OTHER INFORMATION: Synthesized

<400> SEQUENCE: 28
cttccctgct gaattctatc aaac                                         24

<210> SEQ ID NO 29
<211> LENGTH: 28
<212> TYPE: DNA
<213> ORGANISM: Artificial sequence
<220> FEATURE:
<223> OTHER INFORMATION: Synthesized

<400> SEQUENCE: 29
ttgtcctttc ccagttattt ccctcaac					28

<210> SEQ ID NO 30
<211> LENGTH: 29
<212> TYPE: DNA
<213> ORGANISM: Artificial sequence
<220> FEATURE:
<223> OTHER INFORMATION: Synthesized

<400> SEQUENCE: 30
cactttgctt ccaatcattg attccaccc					29

<210> SEQ ID NO 31
<211> LENGTH: 29
<212> TYPE: DNA
<213> ORGANISM: Artificial sequence
<220> FEATURE:
<223> OTHER INFORMATION: Synthesized

<400> SEQUENCE: 31 cccccccca aaaaaggaa atacaaatc					29

<210> SEQ ID NO 32
<211> LENGTH: 26
<212> TYPE: DNA
<213> ORGANISM: Artificial sequence
<220> FEATURE:
<223> OTHER INFORMATION: Synthesized

<400> SEQUENCE: 32
tctttagcta aatcagctca ctaccc					26

<210> SEQ ID NO 33
<211> LENGTH: 26
<212> TYPE: DNA
<213> ORGANISM: Artificial sequence
<220> FEATURE:
<223> OTHER INFORMATION: Synthesized

<400> SEQUENCE: 33
caaagccttc tctcgcacat tctttc					26

<210> SEQ ID NO 34
<211> LENGTH: 35
<212> TYPE: DNA
<213> ORGANISM: Artificial sequence
<220> FEATURE:
<223> OTHER INFORMATION: Synthesized

<400> SEQUENCE: 34
aaccacgtcc tttcctccgt catccctaca ccaac					35

<210> SEQ ID NO 35
<211> LENGTH: 39
<212> TYPE: DNA
<213> ORGANISM: Artificial sequence
<220> FEATURE:
<223> OTHER INFORMATION: Synthesized

<400> SEQUENCE: 35
cccccactca aatctcatct tgtagctccc ataatcccc					39

<210> SEQ ID NO 36
<211> LENGTH: 31
<212> TYPE: DNA
<213> ORGANISM: Artificial sequence
<220> FEATURE:
<223> OTHER INFORMATION: Synthesized

<400> SEQUENCE: 36
acttgtcccc atgattcaat tatctcccac c        31

<210> SEQ ID NO 37
<211> LENGTH: 32
<212> TYPE: DNA
<213> ORGANISM: Artificial sequence
<220> FEATURE:
<223> OTHER INFORMATION: Synthesized

<400> SEQUENCE: 37
ttctaaaact ctttgctgca cccccattta ac       32

<210> SEQ ID NO 38
<211> LENGTH: 39
<212> TYPE: DNA
<213> ORGANISM: Artificial sequence
<220> FEATURE:
<223> OTHER INFORMATION: Synthesized

<400> SEQUENCE: 38
aatttcagcc taaatttccc gacaccttca ttttctccc   39

<210> SEQ ID NO 39
<211> LENGTH: 57
<212> TYPE: DNA
<213> ORGANISM: Artificial sequence
<220> FEATURE:
<223> OTHER INFORMATION: Synthesized

<400> SEQUENCE: 39
tcctatccgg ccttccatat cacccctccc cacactcttc ttcaaggttc accttcc   57

<210> SEQ ID NO 40
<211> LENGTH: 27
<212> TYPE: DNA
<213> ORGANISM: Artificial sequence
<220> FEATURE:
<223> OTHER INFORMATION: Synthesized

<400> SEQUENCE: 40
gaccttcatc acctttgtt tcatctc      27

<210> SEQ ID NO 41
<211> LENGTH: 57
<212> TYPE: DNA
<213> ORGANISM: Artificial sequence
<220> FEATURE:
<223> OTHER INFORMATION: Synthesized

<400> SEQUENCE: 41
tcctatccgg ccttccatat cacccctccc cacactcttc ttcaaggttc accttcc   57

<210> SEQ ID NO 42
<211> LENGTH: 27
<212> TYPE: DNA
<213> ORGANISM: Artificial sequence
<220> FEATURE:
<223> OTHER INFORMATION: Synthesized

<400> SEQUENCE: 42
gaccttcatc accttttgtt tcatctc					27

<210> SEQ ID NO 43
<211> LENGTH: 55
<212> TYPE: DNA
<213> ORGANISM: Artificial sequence
<220> FEATURE:
<223> OTHER INFORMATION: Synthesized

<400> SEQUENCE: 43
tcctatccgg ccttccatat cacccctcct ctcaaagttt tctgcctcaa attcc					55

<210> SEQ ID NO 44
<211> LENGTH: 33
<212> TYPE: DNA
<213> ORGANISM: Artificial sequence
<220> FEATURE:
<223> OTHER INFORMATION: Synthesized

<400> SEQUENCE: 44
tttcgaaacc ccctcattcc acgaaaaata ccc					33

<210> SEQ ID NO 45
<211> LENGTH: 64
<212> TYPE: DNA
<213> ORGANISM: Artificial sequence
<220> FEATURE:
<223> OTHER INFORMATION: Synthesized

<400> SEQUENCE: 45
tcctatccgg ccttccatat cacccctctg tcccctaaa attcatatgc caatcttaac					60 ctcc					64

<210> SEQ ID NO 46
<211> LENGTH: 45
<212> TYPE: DNA
<213> ORGANISM: Artificial sequence
<220> FEATURE:
<223> OTHER INFORMATION: Synthesized

<400> SEQUENCE: 46
tctccacccc catgacctaa tcacctccca aagttcccca ccttc					45

<210> SEQ ID NO 47
<211> LENGTH: 55
<212> TYPE: DNA
<213> ORGANISM: Artificial sequence
<220> FEATURE:
<223> OTHER INFORMATION: Synthesized

<400> SEQUENCE: 47
tcctatccgg ccttccatat cacccctcaa cccttataac cagagatctt tctcc					55

<210> SEQ ID NO 48
<211> LENGTH: 27
<212> TYPE: DNA
<213> ORGANISM: Artificial sequence
<220> FEATURE:
<223> OTHER INFORMATION: Synthesized

<400> SEQUENCE: 48
tcaagtccct ctcatgcttc taatcac					27

```
<210> SEQ ID NO 49
<211> LENGTH: 65
<212> TYPE: DNA
<213> ORGANISM: Artificial sequence
<220> FEATURE:
<223> OTHER INFORMATION: Synthesized

<400> SEQUENCE: 49
accactcttc ctcagaagat atccttcccc tacttctgtc aattcatcag actcattctc      60
catcc                                                                  65

<210> SEQ ID NO 50
<211> LENGTH: 32
<212> TYPE: DNA
<213> ORGANISM: Artificial sequence
<220> FEATURE:
<223> OTHER INFORMATION: Synthesized

<400> SEQUENCE: 50
aacatctctt ccccaaagga tcacaactcc tc                                    32

<210> SEQ ID NO 51
<211> LENGTH: 51
<212> TYPE: DNA
<213> ORGANISM: Artificial sequence
<220> FEATURE:
<223> OTHER INFORMATION: Synthesized

<400> SEQUENCE: 51
accactcttc ctcagaagat atccttcctt tgaaagtatt ccctcctcct c               51

<210> SEQ ID NO 52
<211> LENGTH: 24
<212> TYPE: DNA
<213> ORGANISM: Artificial sequence
<220> FEATURE:
<223> OTHER INFORMATION: Synthesized

<400> SEQUENCE: 52
cttccctgct gaattctatc aaac                                             24

<210> SEQ ID NO 53
<211> LENGTH: 56
<212> TYPE: DNA
<213> ORGANISM: Artificial sequence
<220> FEATURE:
<223> OTHER INFORMATION: Synthesized

<400> SEQUENCE: 53
accactcttc ctcagaagat atccttcctt gtcctttccc agttatttcc ctcaac          56

<210> SEQ ID NO 54
<211> LENGTH: 29
<212> TYPE: DNA
<213> ORGANISM: Artificial sequence
<220> FEATURE:
<223> OTHER INFORMATION: Synthesized

<400> SEQUENCE: 54
cactttgctt ccaatcattg attccaccc                                        29

<210> SEQ ID NO 55
<211> LENGTH: 57
<212> TYPE: DNA
<213> ORGANISM: Artificial sequence
```

```
<220> FEATURE:
<223> OTHER INFORMATION: Synthesized

<400> SEQUENCE: 55
accactcttc ctcagaagat atccttcccc cccccccaaa aaaggaaat acaaatc          57

<210> SEQ ID NO 56
<211> LENGTH: 26
<212> TYPE: DNA
<213> ORGANISM: Artificial sequence
<220> FEATURE:
<223> OTHER INFORMATION: Synthesized

<400> SEQUENCE: 56
tctttagcta aatcagctca ctaccc                                          26

<210> SEQ ID NO 57
<211> LENGTH: 54
<212> TYPE: DNA
<213> ORGANISM: Artificial sequence
<220> FEATURE:
<223> OTHER INFORMATION: Synthesized

<400> SEQUENCE: 57
accactcttc ctcagaagat atccttccca aagccttctc tcgcacattc tttc           54

<210> SEQ ID NO 58
<211> LENGTH: 35
<212> TYPE: DNA
<213> ORGANISM: Artificial sequence
<220> FEATURE:
<223> OTHER INFORMATION: Synthesized

<400> SEQUENCE: 58
aaccacgtcc tttcctccgt catccctaca ccaac                                35

<210> SEQ ID NO 59
<211> LENGTH: 57
<212> TYPE: DNA
<213> ORGANISM: Artificial sequence
<220> FEATURE:
<223> OTHER INFORMATION: Synthesized

<400> SEQUENCE: 59
aaccccgtac aaaatcgcca ccaccaacct cttgcctaca cctgcattta ccccaac        57

<210> SEQ ID NO 60
<211> LENGTH: 27
<212> TYPE: DNA
<213> ORGANISM: Artificial sequence
<220> FEATURE:
<223> OTHER INFORMATION: Synthesized

<400> SEQUENCE: 60
tccacagctc ctgcttatat caaaacc                                         27

<210> SEQ ID NO 61
<211> LENGTH: 65
<212> TYPE: DNA
<213> ORGANISM: Artificial sequence
<220> FEATURE:
<223> OTHER INFORMATION: Synthesized
```

<400> SEQUENCE: 61
aaccccgtac aaaatcgcca ccaccaacta aaacacattc aacactgtct cccagacacc    60
caaac                                                                65

<210> SEQ ID NO 62
<211> LENGTH: 28
<212> TYPE: DNA
<213> ORGANISM: Artificial sequence
<220> FEATURE:
<223> OTHER INFORMATION: Synthesized

<400> SEQUENCE: 62
ctcttcccca ccatgtgttc attcattc                                       28

<210> SEQ ID NO 63
<211> LENGTH: 57
<212> TYPE: DNA
<213> ORGANISM: Artificial sequence
<220> FEATURE:
<223> OTHER INFORMATION: Synthesized

<400> SEQUENCE: 63
aaccccgtac aaaatcgcca ccaccaactc ctctagcatt aatagttacc acacctc       57

<210> SEQ ID NO 64
<211> LENGTH: 34
<212> TYPE: DNA
<213> ORGANISM: Artificial sequence
<220> FEATURE:
<223> OTHER INFORMATION: Synthesized

<400> SEQUENCE: 64
tactgaccaa tccaatgtca aattcctcta ccac                                34

<210> SEQ ID NO 65
<211> LENGTH: 62
<212> TYPE: DNA
<213> ORGANISM: Artificial sequence
<220> FEATURE:
<223> OTHER INFORMATION: Synthesized

<400> SEQUENCE: 65
aaccccgtac aaaatcgcca ccaccaacaa accccaatgc ccaaatcttg ccattttttc    60
ac                                                                   62

<210> SEQ ID NO 66
<211> LENGTH: 36
<212> TYPE: DNA
<213> ORGANISM: Artificial sequence
<220> FEATURE:
<223> OTHER INFORMATION: Synthesized

<400> SEQUENCE: 66
tacccttcct tccctgaaca cagtcaatca tttctc                              36

<210> SEQ ID NO 67
<211> LENGTH: 60
<212> TYPE: DNA
<213> ORGANISM: Artificial sequence
<220> FEATURE:
<223> OTHER INFORMATION: Synthesized

<400> SEQUENCE: 67
aaccccgtac aaaatcgcca ccaccaacct ctgccctcac gacccaatca cctttcaaac    60

```
<210> SEQ ID NO 68
<211> LENGTH: 34
<212> TYPE: DNA
<213> ORGANISM: Artificial sequence
<220> FEATURE:
<223> OTHER INFORMATION: Synthesized

<400> SEQUENCE: 68
cctccaaaac tcatctggaa atttattccc ccac                              34

<210> SEQ ID NO 69
<211> LENGTH: 40
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: FAM

<400> SEQUENCE: 69
aggagttcct atccggcctt ccatatcacc cctcactcct                        40

<210> SEQ ID NO 70
<211> LENGTH: 40
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: FAM

<400> SEQUENCE: 70
aggagtacca ctcttcctca gaagatatcc ttccactcct                        40

<210> SEQ ID NO 71
<211> LENGTH: 40
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: HEX

<400> SEQUENCE: 71
aggagtaacc ccgtacaaaa tcgccaccac caacactcct                        40

<210> SEQ ID NO 72
<211> LENGTH: 67
<212> TYPE: DNA
<213> ORGANISM: Artificial sequence
<220> FEATURE:
<223> OTHER INFORMATION: Synthesized

<400> SEQUENCE: 72
ctccataccc actatcaatc atatcaccat cctcggattg gtattggagg ttattaataa  60
tggtgga                                                            67

<210> SEQ ID NO 73
<211> LENGTH: 33
<212> TYPE: DNA
<213> ORGANISM: Artificial sequence
```

<220> FEATURE:
<223> OTHER INFORMATION: Synthesized

<400> SEQUENCE: 73
tccaccatta ttaataacct ccaataccaa tcc          33

<210> SEQ ID NO 74
<211> LENGTH: 34
<212> TYPE: DNA
<213> ORGANISM: Artificial sequence
<220> FEATURE:
<223> OTHER INFORMATION: Synthesized

<400> SEQUENCE: 74
ctccataccc actatcaatc atatcaccat cctc          34

<210> SEQ ID NO 75
<211> LENGTH: 67
<212> TYPE: DNA
<213> ORGANISM: Artificial sequence
<220> FEATURE:
<223> OTHER INFORMATION: Synthesized

<400> SEQUENCE: 75
tccaccatta ttaataacct ccaataccaa tccgaggatg gtgatatgat tgatagtggg    60
tatggag                                                              67

<210> SEQ ID NO 76
<211> LENGTH: 33
<212> TYPE: DNA
<213> ORGANISM: Artificial sequence
<220> FEATURE:
<223> OTHER INFORMATION: Synthesized

<400> SEQUENCE: 76
tccaccatta ttaataacct ccaataccaa tcc          33

<210> SEQ ID NO 77
<211> LENGTH: 67
<212> TYPE: DNA
<213> ORGANISM: Artificial sequence
<220> FEATURE:
<223> OTHER INFORMATION: Synthesized

<400> SEQUENCE: 77
ctccataccc agtatcaatg atatcagcat cctcggattg gtattgcagg ttattaataa    60
tcgtgga                                                              67

<210> SEQ ID NO 78
<211> LENGTH: 67
<212> TYPE: DNA
<213> ORGANISM: Artificial sequence
<220> FEATURE:
<223> OTHER INFORMATION: Synthesized

<400> SEQUENCE: 78
tccacgatta ttaataacct gcaataccaa tccgaggatg ctgatatcat tgatactggg    60
tatggag                                                              67

<210> SEQ ID NO 79
<211> LENGTH: 34
<212> TYPE: DNA
<213> ORGANISM: Artificial sequence
<220> FEATURE:
<223> OTHER INFORMATION: Synthesized

<400> SEQUENCE: 79
ctccataccc actatcaatc atatcaccat cctc                                 34

<210> SEQ ID NO 80
<211> LENGTH: 34
<212> TYPE: DNA
<213> ORGANISM: Artificial sequence
<220> FEATURE:
<223> OTHER INFORMATION: Synthesized

<400> SEQUENCE: 80
ctccataccc actatcaatc atatcaccat cctc                                 34

<210> SEQ ID NO 81
<211> LENGTH: 67
<212> TYPE: DNA
<213> ORGANISM: Artificial sequence
<220> FEATURE:
<223> OTHER INFORMATION: Synthesized

<400> SEQUENCE: 81
tccacgatta ttaataacct gcaataccaa tccgaggatg ctgatatcat tgatactggg    60
tatggag                                                              67

<210> SEQ ID NO 82
<211> LENGTH: 67
<212> TYPE: DNA
<213> ORGANISM: Artificial sequence
<220> FEATURE:
<223> OTHER INFORMATION: Synthesized

<400> SEQUENCE: 82
ctccataccc agtatcaatg atatcagcat cctcggattg gtattgcagg ttattaataa    60
tcgtgga                                                              67

<210> SEQ ID NO 83
<211> LENGTH: 33
<212> TYPE: DNA
<213> ORGANISM: Artificial sequence
<220> FEATURE:
<223> OTHER INFORMATION: Synthesized

<400> SEQUENCE: 83
tccaccatta ttaataacct ccaataccaa tcc                                 33

<210> SEQ ID NO 84
<211> LENGTH: 33
<212> TYPE: DNA
<213> ORGANISM: Artificial sequence
<220> FEATURE:
<223> OTHER INFORMATION: Synthesized

<400> SEQUENCE: 84
tccaccatta ttaataacct ccaataccaa tcc                                 33

<210> SEQ ID NO 85
<211> LENGTH: 67
<212> TYPE: DNA
<213> ORGANISM: Artificial sequence
<220> FEATURE:
<223> OTHER INFORMATION: Synthesized

```
<400> SEQUENCE: 85 ctccatacccc agtatcaatg atatcagcat cctcggattg gtattgcagg ttattaataa    60
tcgtgga                                                               67

<210> SEQ ID NO 86
<211> LENGTH: 67
<212> TYPE: DNA
<213> ORGANISM: Artificial sequence
<220> FEATURE:
<223> OTHER INFORMATION: Synthesized

<400> SEQUENCE: 86
tccacgatta ttaataacct gcaataccaa tccgaggatg ctgatatcat tgatactggg    60
tatggag                                                               67

<210> SEQ ID NO 87
<211> LENGTH: 34
<212> TYPE: DNA
<213> ORGANISM: Artificial sequence
<220> FEATURE:
<223> OTHER INFORMATION: Synthesized

<400> SEQUENCE: 87 ctccatacccc actatcaatc atatcaccat cctc                                34
```

DIGITAL AMPLIFICATION WITH PRIMERS OF LIMITED NUCLEOTIDE COMPOSITION

CROSS-REFERENCE TO RELATED APPLICATION

The present application is a US national stage entry of international application no. PCT/US2018/046360 filed Aug. 10, 2018, which claims the benefit of U.S. 62/544,605 filed Aug. 11, 2017 incorporated by reference in its entirety, for all purposes.

SEQUENCE LISTING

The application includes sequences in a txt filing designated 543918SEQLST.TXT, of 17,544 bytes, created Feb. 10, 2020, which is incorporated by reference.

BACKGROUND

The polymerase chain reaction (PCR) is used to quantify nucleic acids by amplifying a nucleic acid molecule with the enzyme DNA polymerase. Conventional PCR is based on the theory that amplification is exponential. Therefore, nucleic acids may be quantified by comparing the number of amplification cycles and amount of PCR end-product to those of a reference sample.

Digital PCR (or dPCR) is a variation of PCR in a sample is partitioned so that individual nucleic acid molecules within the sample are localized and concentrated within many discrete regions, such as micro well plates, capillaries, oil emulsion, and arrays of miniaturized chambers. Each region is subject to an individual PCR. The PCR solution is divided into smaller reactions and are then made to run PCR individually. After multiple PCR amplification cycles, the samples are checked for fluorescence with a binary readout of "0" or "1". The number of fluorescing samples provides an indication of the number of target molecules in the initial sample. Although there is growing interest in dPCR, interpretation of results can be complicated due to unintended amplification products resulting in intermediate values between the expected binary readouts.

SUMMARY

The invention provides a method of performing a digital amplification on a target nucleic acid in a sample comprising: partitioning a sample comprising a target nucleic acid into aliquots, conducting amplification reactions in the aliquots wherein an amplified segment of the target nucleic acid is formed by extension of a pair of forward and reverse primers on the target nucleic acid if the target nucleic acid is present in the aliquot; wherein the primers are underrepresented in one or more of the four standard nucleotide types, the underrepresented nucleotide type(s) being the same in the primers, and detecting an amplified segment, if present, in each aliquot. Optionally, the amplified segment is the predominant amplification product formed from by extension of the forward and/or reverse primers.

Optionally, the copy number of the target nucleic acid is determined by the number of aliquots containing or lacking the amplified segment, e.g., following a Poisson distribution. Optionally, the sample comprises a plurality of target nucleic acids, and the amplification is performed with a plurality of forward and reverse primer pairs corresponding to the respective targets.

Optionally the sample comprises a plurality of target nucleic acids, and the amplification is performed with a plurality of forward and reverse primer pairs corresponding to the respective targets, each of which is underrepresented in the same standard nucleotide type(s), optionally wherein the pluralities are each at least 2, 3, 4, 5, 6, 7, 8, 9 or 10. Optionally, each of the primer pairs is underrepresented in the same one and only one standard nucleotide type.

Optionally, the target nucleic acids are from different chromosomes or the same chromosome. Optionally, the target nucleic acid is DNA, RNA, cDNA, cell-free DNA, cell-free fetal DNA, or circulating tumor DNA. Optionally, the sample is a tissue, or a body fluid. Optionally, the amplification reactions in the aliquots are polymerase chain reactions. Optionally, the amplification reactions in the aliquots are isothermal amplification reactions. Optionally, the amplification reactions in the aliquots are a combination of isothermal and polymerase chain reactions.

In some methods, before or after partitioning a sample comprising a target nucleic acid into aliquots, the target nucleic acid is pre-amplified. In some methods, before or after partitioning a sample comprising a target nucleic acid into aliquots, the target nucleic acid is treated with a chemical, protein or enzyme. In some methods, the target nucleic acid is treated with bisulfite to determine methylation state of the target nucleic acid.

Optionally, the detecting indicates whether a predefined genetic abnormality is present in the target nucleic acid. Optionally, the predefined genetic abnormality is a chromosome aneuploidy, single nucleotide polymorphism (SNP), insertion, or deletion. Optionally, the chromosome aneuploidy is trisomy 21, trisomy 18, trisomy 13, triple X, or monosomy X. Optionally, a chromosome aneuploidy is determined based on a ratio of copy numbers of target nucleic acids on the two chromosomes.

Optionally, a chromosome aneuploidy is determined based on a ratio of copy numbers of target nucleic acids on two chromosomes, one of which is subject to the aneuploidy and the other of which is not. Optionally, the method is performed on a plurality of target nucleic acids including a target nucleic acid from chromosome 21, a target nucleic acid from chromosome 18 and a target nucleic acid from chromosome 13, wherein the detecting indicates one of the target nucleic acids includes the aneuploidy. Optionally, the method is performed on samples from a population, wherein the method identifies samples containing the chromosome aneuploidy, chromosomes lacking the aneuploidy and inconclusive samples, and the method further comprising sequencing DNA from the inconclusive samples to determine whether the samples determined to be inclusive by the digital amplification analysis have the chromosome aneuploidy. Optionally, the sequencing is by a next generation technique. Optionally, the sample is a cell-free nucleic acid sample. Optionally, the cell-free nucleic acid sample from a pregnant female and the target nucleic is a fetal nucleic acid. Optionally the fetal nucleic acid is a segment of the Y-chromosome or encoded by the Y-chromosome. Optionally, the fetal nucleic acid is differentially methylated compared with a corresponding maternal nucleic acid. Optionally, the method is performed with a plurality of target nucleic acids which include a fetal nucleic acid target and a corresponding maternal target nucleic acid target. Optionally, the method is performed with a plurality of target nucleic acids which include a genomic target released by lysed blood cells and a cell free nucleic acid target.

Optionally, the target nucleic acid includes a site of a single nucleotide polymorphism (SNP), insertion, or deletion. Optionally, the digital PCR is droplet digital PCR (ddPCR). Optionally, the amplified segment is detected with an intercalating dye. Optionally, the DNA intercalating dye is EVAGreen®. Optionally, the amplified segment is detected with a fluorophore labeled oligonucleotide probe. Optionally, the fluorophore labeled oligonucleotide probe is a Taqman probe, Molecular Beacon probe or ying yang probe. Optionally, the fluorophore is FAM, or HEX. Optionally, the plurality of target nucleic acids are detected in a single droplet reaction. Optionally, the plurality of targets are detected based on amplicon signal intensity. Optionally, amplicon signal intensities of the plurality of target nucleic acids are distinguishable due to differences in amplicon sizes and/or primer concentrations. Optionally, the amplified segments are detected using a DNA intercalating dye and a fluorophore labeled oligonucleotide probe. Optionally, two target nucleic acid are components of the same contiguous nucleic acid. Optionally, the forward primer and/or reverse primer is linked at its 5' end to an artificial sequence underrepresented in the nucleotide. Optionally, the multiple target nucleic acids are amplified with the same or different artificial sequence underrepresented in the nucleotide linked to the primer pairs. Optionally, the amplified segment is detected by melting curve analysis.

In some methods, the forward and reverse primers are underrepresented in only one of the four standard nucleotide types. In some method, the forward and reverse primers contain no more than two nucleotides of the underrepresented nucleotide type. In some methods, primer binding sites for the forward and reverse primers are identified by searching the target nucleic acid for primer binding sites underrepresented in the complement of the nucleotide type(s) underrepresented in the forward and reverse primers. In some methods, the amplified segment is the predominant amplification product formed by extension of the forward and/or reverse primers.

In some methods, the primers have one and only one underrepresented standard nucleotide type, and the complement of the underrepresented standard nucleotide type is present at the 3' terminal position of at least one of the primers. In some methods, the complement of the underrepresented standard nucleotide type is present at the 3' terminal position of each of the primers. In some methods, the primers have one and only one underrepresented standard nucleotide type, and the underrepresented nucleotide type is present at the 5' terminal position of one of the primers. In some methods, the underrepresented standard nucleotide type is present at the 5' terminal position of all of the primers.

BRIEF DESCRIPTION OF THE DRAWINGS

FIG. 2 shows a template in which primer binding sites show three mismatches (forward primer) or two mismatches (reverse primer) to primers of three nucleotide-type composition. The sequences in FIG. 2 (top to bottom) are SEQ ID NO:76 (reversed from as shown so as to depict 5' to 3' in SL), SEQ ID NO:77, SEQ ID NO:78 (reversed from as shown so as to depict 5' to 3' in SL), SEQ ID NO:79, SEQ ID NO:80, SEQ ID NO:81 (reversed from as shown so as to depict 5' to 3' in SL), SEQ ID NO:82, SEQ ID NO:83 (reversed from as shown so as to depict 5' to 3' in SL).

FIG. 3 shows examples of mismatch binding reagents. The sequences in FIG. 3 are (top to bottom) SEQ ID NO:84 (reversed from as shown so as to depict 5' to 3' in SL); SEQ ID NO:85; SEQ ID NO:86 (reversed from as shown so as to depict 5' to 3' in SL); and SEQ ID NO:87.

DEFINITIONS

Figure 1:
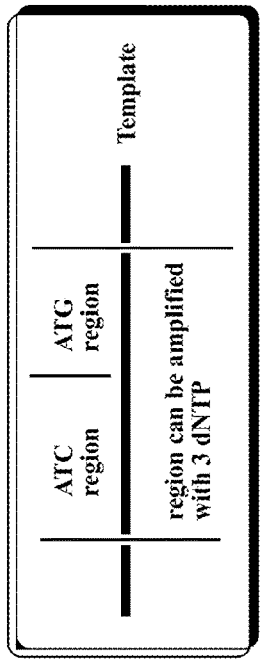
FIG. 1 shows a target nucleic acid and exemplary three nucleotide primers and primer binding sites. The upper portion of the figure shows one strand of the target nucleic acid containing the complement of the forward primer binding site (ATC nucleotides) contiguous with the reverse primer binding site (ATG site). The lower portion shows the primers bound to their respective binding sites on opposing strands. Amplification can proceed in the presence of dTTP, dATP, and dGTP (and other typical PCR components) but dCTP is not required because there are no G nucleotides in the strands of the target nucleic acid being amplified. The sequences in FIG. 1 are (top to bottom) SEQ ID NO:72, SEQ ID NO:73 (reversed from as shown so as to depict 5' to 3' in SL), SEQ ID NO:74, SEQ ID NO:75 (reversed from as shown so as to depict 5' to 3' in SL).

Unless defined otherwise, all technical and scientific terms used herein have the same meaning as commonly understood in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting. The term "a" or "an" entity refers to one or more of that entity; for example, "a nucleic acid," represents one or more nucleic acids. Therefore, the terms "a" (or "an"), "one or more," and "at least one" can be used interchangeably herein.

Nucleic acids include DNA and RNA and DNA-RNA chimeras can be double-stranded or single-stranded. DNA can be genomic, cDNA, methylated DNA or synthetic DNA. RNA can be mRNA, miRNA, tRNA, rRNA, hnRNA, methylated RNA among others. The term "nucleic acid" encompasses any physical string of monomer units that can be corresponded to a string of nucleotides, including a polymer of nucleotides (e.g., a typical DNA or RNA polymer), peptide nucleic acid (PNA), modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

The four conventional nucleotide bases are A, T/U, C and G with T being present in DNA and U in RNA. The nucleotides found in targets are usually natural nucleotides (deoxyribonucleotides or ribonucleotides). Such is also the case is nucleotides forming primers.

Complementarity of nucleic acid strands means that the strands form a stabile duplex due to hydrogen bonding between their nucleobase groups. The complementary bases are in DNA, A with T and C with G, and, in RNA, C with G, and U with A. Nucleotides in respective strands are complementarity when they form one of these (Watson-Crick pairings) when the strands are maximally aligned. Nucleotides are mismatched when they do not form a complementarity pair when their respective strands are maximally aligned. Complementarity of strands can be perfect or substantial. Perfect complementarity between two strands means that the two strands can form a duplex in which every base in the duplex is bonded to a complementary base by Watson-Crick pairing. Substantial complementary means most but not necessarily all bases in strands form Watson-Crick pairs to form a stable hybrid complex in set of hybridization conditions (e.g., salt concentration and temperature). For example, some primers can duplex with a primer binding site notwithstanding up to 1, 2 or 3 positions of mismatch, provided such mismatches are not at the 3' end and preferably not proximate thereto (e.g., within 4 nucleotides). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41 (% G+C)−675/N−% mismatch, where N=total number of bases.

A mismatch means that a nucleotide in one strand of nucleic acid does not or cannot pair through Watson-Crick base pairing with a nucleotide in an opposing complementary nucleic acid strand. Examples of mismatches are but not limited to AA, AG, AC, GG, CC, TT, TG, TC, UU, UG, UC, and UT base pairs. Mismatches can happen between DNA and DNA molecules, DNA and RNA molecules, RNA and RNA molecules, and among other natural or artificial nucleic acid analogs.

Mismatch binding reagents or agents are any molecules or any modification in underrepresented primers that can stabilize the underrepresented primer hybridization with underrepresented primer binding sites through chemical interaction or physical interaction. Modification of underrepresented primers may be modified in any way, as long as a given modification is compatible with the desired function of a given underrepresented primers as can be easily determined. Modifications include base modifications, sugar modifications or backbone modifications. Some small molecules can bind to mismatched bases through hydrogen bonds presumably complementary to those in the unpaired base and stabilize the duplex with a high base selectivity. Metal ions have been shown to interact with nucleic acids for their structure formation and folding. Ono A., Togashi H. (Ono & Togashi, 2004, *Angewandte Chemie* (International Ed. in English), 43(33), 4300-4302) showed that addition of mercury ion in solution increases the Tm DNA duplex with T-T mismatch by 5° C. Torigoe H., Okamoto I. et al. (Torigoe et al., 2012, *Biochimie*, 94(11), 2431-2440) showed that silver ion selectively bind and stabilize C—C mismatch. A series of rhodium complexes capable of high-selectivity mismatch site recognition has been designed and synthesized by Cordier C., Pierre V. C. et al. (Cordier, Pierre, & Barton, 2007, *Journal of the American Chemical Society*, 129(40), 12287-12295). Nakatani K., Sando S., et al. (Nakatani, Sando, Kumasawa, Kikuchi, & Saito, 2001, *Journal of the American Chemical Society*, 123(50), 12650-12657) have developed a series of naphthyridine based small molecules to selectively recognize mismatched DNA.

Hybridization or annealing conditions include chemical components and their concentrations (e.g., salts, chelating agents, formamide) of an aqueous or organic solution containing the nucleic acids, and the temperature of the mixture in which one nucleic acid strand bonds to a second nucleic acid strand by complementary strand interactions to produce a hybridization complex.

A sample is a composition in which one or more target nucleic acids of interest may be present, including patient samples, plant or animal materials, waste materials, materials for forensic analysis, environmental samples, Circulation tumor cell (CTC), cell free DNA, liquid biopsy, and the like. Samples include any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are tissue samples (including body fluids) from a human or an animal having or suspected of having a disease or condition, particularly infection by a virus. Other samples of interest include industrial samples, such as for water testing, food testing, contamination control, and the like. Sample components may include target and non-target nucleic acids, and other materials such as salts, acids, bases, detergents, proteins, carbohydrates, lipids and other organic or inorganic materials. A sample may or may not be subject of processing to purify a target nucleic acid before amplification. Further processing can treatment with a detergent or denaturant to release nucleic acids from cells or viruses, removal or inactivation of non-nucleic acid components and concentration of nucleic acids.

A "target nucleic acid" refers to a nucleic acid molecule or population of related nucleic acid molecules that is or may be present within a sample. A target nucleic acid can include a segment to be amplified defined by primer binding sites. The segment can be the entire nucleic acid or any segment thereof of length amenable to amplification. A target nucleic acid can be an entire chromosome, gene or cDNA, and a target segment can be for example, only 40-500 of these nucleotides. A target segment can present on any strand (sense or anti-sense) of the structure. A target nucleic acid can be RNA (e.g., viral RNA, microRNA, mRNA, cRNA, rRNA, hnRNA, cfRNA, or DNA (genomic, somatic, cfDNA, cffDNA, or cDNA) among others.

The target nucleic acid can be from a pathogenic microorganism, such as a virus, bacteria or fungus, or can be endogenous to a patient. Viral nucleic acids (e.g., genomic, mRNA) form a useful target for analyses of viral sequences. Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus. Examples of such bacteria include chlamydia, rickettsial bacteria, mycobacteria, staphylococci, treptocci, pneumonococci, meningococci and conococci, *klebsiella, proteus, serratia, pseudomonas, legionella,* diphtheria, *salmonella,* bacilli, cholera, tetanus, botulism, anthrax, plague, leptospirosis, Lymes disease bacteria, streptococci, or *neisseria*. rRNA is a particularly useful target nucleic acid for typing bacteria. Detection of human or animal genes is useful for detecting presence or susceptibility to disease. Examples of genes that can be the subject of detection include cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses.

An underrepresented nucleotide type is one present in no more than 20% of positions in a primer or primer binding site. Typically if one nucleotide type is underrepresented in a primer, its complement is underrepresented in the primer binding site (or vice versa). Typically a primer has nucleotide composition of, A, G, C, T or, A, G, C, U, although in the present methods one or more of the standard nucleotide types may be absent. A primer may include unnatural nucleotide, such as Iso C and IsoG, deaza G or deaza A. These are scored the same way as corresponding standard nucleotides in determining the number or percentage of underrepresented nucleotides. An analog corresponds with a natural nucleotide if it has the same relative pairing affinity with other natural nucleotides. Thus deaza G or inosine are analogs of G because they pair more strongly with C than any of the other natural nucleotides. As an example, if G is an underrepresented nucleotide type, to determine a percentage of the underrepresented nucleotide type in a primer, deaza G is included in the numerator (as well as the denominator) and deaza A only in the denominator. Thus, the percentage of underrepresented nucleotide in a primer containing one G, one deaza G and 20 nucleotides total is 10%. Typically an underrepresented nucleotide type is present in 0, 1 or 2 units at internal positions and optionally one at the 5' terminal position in each primer and 0, 1, 2, 3 or 4 units in each primer binding sites, and in 0 units in an artificial sequence. Ideally one and only unit of the underrepresented nucleotide type is at the 5' terminal position. If one and only one of the four-nucleotide-types is underrepresented it is the least represented (including null representation) of the four standard nucleotide types. If the primer contains a degenerate position, the position is counted as being an underrepresented nucleotide type position (i.e., in the numerator as well as the denominator) if the degeneracy includes the underrepresented nucleotide type and in the denominator only otherwise. A nucleotide analog having no preference among binding to the natural nucleotide types is treated the same as a degenerate position. A primer containing underrepresented nucleotide type(s) is called an underrepresented primer. A probe containing underrepresented nucleotide type(s) called underrepresented probe.

The term "dNTP" generally refers to an individual or combination of deoxynucleotides containing a phosphate, sugar and organic base in the triphosphate form, that provide precursors required by a DNA polymerase for DNA synthesis. A dNTP mixture may include each of the naturally occurring deoxynucleotides (i.e., adenine (A), guanine (G), cytosine (C), uracil (U), and Thymine (T)). In some embodiments, each of the naturally occurring deoxynucleotides may be replaced or supplemented with a synthetic analog; such as inosine, isoG, IsoC, deaza G, deaza A, and so forth. When nucleotides are underrepresented in a primer or a probe, the nucleotides are called underrepresented nucleotides. The underrepresented nucleotides can be included in a reaction system as the form of deoxynucleotides or dideoxynucleotides or ribonucleotides. Their complements are called complementary nucleotides of underrepresented nucleotides. The term "ddNTP" generally refers to an individual or combination of dideoxynucleotides containing a phosphate, sugar and organic base in the triphosphate form, that provide precursors required by a DNA polymerase for DNA synthesis. A ddNTP mixture may include each of the naturally occurring dideoxynucleotides (i.e., adenine (A), guanine (G), cytosine (C), uracil (U), and Thymine (T)). In some embodiments, each of the naturally occurring dideoxynucleotides may be replaced or supplemented with a synthetic analog; such as inosine, isoG, IsoC, deazaG, deaza A, and so forth. The term "NTP" generally refers to an individual or combination of Ribonucleotides containing a phosphate, sugar and organic base in the triphosphate form, that provide precursors required by a RNA polymerase for RNA synthesis. A NTP mixture may include each of the naturally occurring Ribonucleotides (i.e., adenine (A), guanine (G), cytosine (C), uracil (U)). In some embodiments, each of the naturally occurring Ribonucleotides may be replaced or supplemented with a synthetic analog; such as inosine, isoG, IsoC, deazaG, deaza A, and so forth.

A primer binding site or probe binding site is interchangeable with underrepresented primer binding site or underrepresented probe binding site in this invention. A primer binding site is a complete or partial site in a target nucleic acid to which a primer hybridizes. A partial site can be supplemented by provision of toehold and junction sequences, which also contain partial primer binding sites as described in WO2016/172632. A partial binding site from a toehold or junction sequence can combine with a partial primer binding site on a target nucleic acid to form a complete primer binding site.

The term "primer" or "probe" is interchangeable with underrepresented primer or underrepresented probe in this invention. A primer or a probe is an oligonucleotide complementary to primer or probe binding site contributed in whole or part by a target nucleic acid. A primer or a probe can be linked at its 5' end to another nucleic acid (sometimes referred to as a tail), not found in or complementary to the target nucleic acid. A 5' tail can have an artificial sequence. For a primer or probe exactly complementary to a primer or a probe binding site, the demarcation between primer or probe and tail is readily apparent in that the tail starts with the first noncomplementary nucleotide encountered moving from the 3' end of the primer or probe. For a primer substantially complementary to a primer binding site, the last nucleotide of the primer is the last nucleotide complementary to the primer binding site encountered moving away from the 3' end of the primer that contributes to primer binding to the target nucleic acid (i.e., primer with this 5' nucleotide has higher TM for the target nucleic acid than a primer without the 5' nucleotide). Complementarity or not between nucleotides in the primer and priming binding site is determined by Watson-Crick pairing or not on maximum alignment of the respective sequences.

A primer or a probe is an oligonucleotide. The term "oligonucleotide" encompasses a singular "oligonucleotide"

as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof and/or DNA RNA chimeric. The term oligonucleotide does not denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, it may contain detection reagents for signal generation/amplification, and it may function to prevent hybridization or impede primer extension if appropriately situated and/or modified. Specific oligonucleotides of the present invention are described in more detail below. As used herein, an oligonucleotide can be virtually any length, limited only by its specific function in the amplification reaction or in detecting an amplification product of the amplification reaction. Oligonucleotides of a defined sequence and chemical structure may be produced by conventional techniques, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof. Oligonucleotides may be modified in any way, as long as a given modification is compatible with the desired function of a given oligonucleotide as can be easily determined. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl (2'-O-ME) substitution to the ribofuranosyl moiety. See "Method for Amplifying Target Nucleic Acids Using Modified Primers," (Becker, Majlessi, & Brentano, 2000, U.S. Pat. No. 6,130,038). Other sugar modifications include, but are not limited to 2'-amino, 2'-fluoro, (L)-alpha-threofuranosyl, and pentopuranosyl modifications. The nucleoside subunits may be joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al., "Peptide Nucleic Acids," (Nielsen, Buchardt, Egholm, & Berg, 1996, U.S. Pat. No. 5,539,082). Other linkage modifications include, but are not limited to, morpholino bonds. Non-limiting examples of oligonucleotides or oligomers contemplated by the present invention include nucleic acid analogs containing bicyclic and tricyclic nucleoside and nucleotide analogs (LNAs). See Imanishi et al., "Bicyclonucleoside and Oligonucleotide Analogues," (Imanishi & Obika, 2001, U.S. Pat. No. 6,268,490); and Wengel et al., "Oligonucleotide Analogues," (Wengel & Nielsen, 2003, U.S. Pat. No. 6,670, 461). Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions. The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

The term "degenerate primer" refers to a mixture of similar primers with differing bases at the varying positions (Mitsuhashi, J. Clin. Lab. Anal., 10(5): 285 93 (1996); von Eggeling et al., Cell. Mol. Biol., 41(5):653 70 (1995); (Zhang et al., Proc. Natl. Acad. Sci. USA, 89:5847 5851 (1992); Telenius et al., Genomics, 13(3):718 25 (1992)). Such primers can include inosine, as inosine is able to base pair with adenosine, cytosine, guanine or thymidine. Degenerate primers allow annealing to and amplification of a variety of target sequences that can be related. Degenerate primers that anneal to target DNA can function as a priming site for further amplification. A degenerate region is a region of a primer that varies, while the rest of the primer can remain the same. Degenerate primers (or regions) denote more than one primer and can be random. A random primer (or regions) denotes that the sequence is not selected, and it can be degenerate but does not have to be. In some embodiments, the 3' target specific regions have a Tm of between about 5° C. and 50° C. In some embodiments, a 15-mer has a Tm of less than about 60° C.

A primer "3' segment or 3' binding region or 3' binding site or 3' hybridization region" is able to bind to a genomic sequence occurring in a genome at a particular frequency or other nucleic acid sequence. In some embodiments, this frequency is between about 0.01% and 2.0%, such as, between about 0.05% and 0.1% or between about 0.1% and 0.5%. In some embodiments, the length of the "binding site" of a primer depends mainly on the averaged lengths of the predicted PCR products based on bioinformatic calculations. The definition includes, without limitation, a "binding region" of between about 4 and 12 bases in length. In more particular embodiments, the length of the 3' binding region can be, for example, between about 4 and 20 bases, or between about 8 and 15 bases. Binding regions having a Tm of between about 10° C. and 60° C. are included within the definition. The term, "primer binding segment," when used herein refers to a primer of specified sequence.

A polymerase is an enzyme that can perform template directed extension of a primer hybridized to the template. It can be a DNA polymerase, an RNA polymerase or a reverse transcriptase. Examples of DNA polymerases include: *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1

DNA polymerase, T4 DNA polymerase, thermosequenase or a wild-type or modified T7 DNA polymerase, 029 Polymerase, Bst Polymerase, Vent Polymerase, 9° Nm Polymerase, Klenow fragment of DNA Polymerase I. Examples of reverse transcriptase: AMV Reverse Transcriptase, MMLV Reverse Transcriptase, HIV Reverse Transcriptase. Examples of RNA polymerases include: T7 RNA polymerase or SP6 RNA polymerase, bacterial RNA polymerases and eukaryotic RNA polymerases.

Amplification refers to either producing an additional copy or copies of all or a segment of a target nucleic acid by template-directed primer extension (target amplification) or amplifying detection signal for qualitatively/quantitatively measurement (signal amplification) or both. Amplification can be performed under temperature cycled or isothermal conditions or combined. Amplification can be linear or exponential.

Many well-known methods of nucleic acid target amplification require thermocycling to alternately denature double-stranded nucleic acids and hybridize primers; however, other well-known methods of nucleic acid amplification are isothermal. The polymerase chain reaction, commonly referred to as PCR (Mullis, 1987 U.S. Pat. No. 4,683,202; Saiki et al., 1985, *Science* (New York, N.Y.), 230(4732), 1350-1354), uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA (Gelfand et al., "Reverse Transcription with Thermostable DNA Polymerases—High Temperature Reverse Transcription," (Gelfand, 1994, U.S. Pat. No. 5,322,770; Gelfand & Myers, 1994, U.S. Pat. No. 5,310,652). Another method of amplifying nucleic acid is called the LCR method (ligase chain reaction, Laffler, Carrino, & Marshall, 1993, *Annales De Biologie Clinique*, 51(9), 821-826). LCR (Laffler et al., 1993, *Annales De Biologie Clinique*, 51(9), 821-826) is based on the reaction in which two adjacent probes are hybridized with a target sequence and ligated to each other by a ligase. The two probes could not be ligated in the absence of the target nucleotide sequence, and thus the presence of the ligated product is indicative of the target nucleotide sequence. The LCR method also requires control of temperature for separation of a complementary chain from a template. Another method is strand displacement amplification (George T. Walker, Little, & Nadeau, 1993, U.S. Pat. No. 5,270,184; George T. Walker, 1995, U.S. Pat. No. 5,455,166; G. T. Walker et al., 1992, *Nucleic Acids Research*, 20(7), 1691-1696, 1992, *Proceedings of the National Academy of Sciences of the United States of America*, 89(1), 392-396), commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (Frailer, Spargo, Van, Walker, & Wright, 2002, European Pat. No. 0 684 315). Other amplification methods include: nucleic acid sequence based amplification (Compton, 1991, *Nature*, 350(6313), 91-92, Malek, Davey, Henderson, & Sooknanan, 1992), commonly referred to as NASBA; one that uses an RNA replicase to amplify the probe molecule itself (Lizardi, Guerra, Lomeli, Tussie-Luna, & Russell Kramer, 1988, *Nature Biotechnology*, 6(10), 1197-1202), commonly referred to as Qβ replicase; a transcription-based amplification method (Kwoh et al., 1989, *Proceedings of the National Academy of Sciences of the United States of America*, 86(4), 1173-1177); self-sustained sequence replication (3SR), (Guatelli et al., 1990, *Proceedings of the National Academy of Sciences of the United States of America*, 87(5), 1874-1878; Landgren (1993) *Trends in Genetics* 9, 199-202; and Lee, H. et al., NUCLEIC ACID AMPLIFICATION TECHNOLOGIES (1997)); and, transcription-mediated amplification (Kwoh et al., 1989, *Proceedings of the National Academy of Sciences of the United States of America*, 86(4), 1173-1177; Kacian & Fultz, 1995, U.S. Pat. No. 5,480,784; Kacian & Fultz, 1996, U.S. Pat. No. 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.). Other illustrative amplification methods suitable for use in accordance with the present invention also include rolling circle amplification (RCA) (Fire & Xu, 1995, *Proceedings of the National Academy of Sciences*, 92(10), 4641-4645; Lizardi, 1998, U.S. Pat. No. 5,854,033); Nucleic Acid Amplification Using Nicking Agents (Van Ness, Galas, & Van Ness, 2006, U.S. Pat. No. 7,112,423); Nicking and Extension Amplification Reaction (NEAR) (Maples et al., 2009, US 2009-0017453 A1); Helicase Dependent Amplification (HDA) (Kong, Vincent, & Xu, 2004, US 2004-0058378 A1; Kong, Vincent, & Xu, 2007 US pat. US2007/0254304 A1); and Loop-Mediated Isothermal Amplification (LAMP) (Notomi & Hase, 2002, U.S. Pat. No. 6,410,278), and Quadruplex priming amplification (*Analyst*, 2014, 139, 1644-1652). Expar amplification (PNAS Apr. 15, 2003 100, 4504-4509). Cross priming amplification (Sci Rep. 2012; 2: 246). SMAP amplification (Nature Methods April 2007; 4(3):257-62). Multiple displacement amplification (MDA, *Proceedings of the National Academy of Sciences* 2005, 102 (48): 17332-6.), Recombinase Polymerase Amplification (*Journal of Clinical Virology* 54 (4): 308-12). Single primer isothermal amplification (SPIA) (clinical chemistry, 2005 vol. 51 no. 10 1973-1981).

Another aspect of amplification is signal amplification. When a sufficient amount of nucleic acids to be detected is available, there are advantages to detecting that sequence directly, instead of making more copies of that target, (e.g., as in PCR and LCR). Traditional methods of direct detection including Northern and Southern blotting and RNase protection assays usually require the use of radioactivity and are not amenable to automation. Other techniques have sought to eliminate the use of radioactivity and/or improve the sensitivity in automatable formats. The cycling probe reaction (CPR) (Duck, Alvarado-Urbina, Burdick, & Collier, 1990b, *BioTechniques*, 9(2), 142-148), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. Branched DNA (bDNA), described by Urdea et al., 1987,

*Gene*, 61(3), 253-264, involves oligonucleotides with branched structures that allow each individual oligonucleotide to carry 35 to 40 labels (e.g., alkaline phosphatase enzymes). While this enhances the signal from a hybridization event, signal from non-specific binding is similarly increased. Other signal amplification include: Invasive Cleavage of Nucleic Acids (Prudent, Hall, Lyamichev, Brow, & Dahlberg, 2006, U.S. Pat. No. 7,011,944); Hybridization Chain Reaction (HCR) (R. M. Dirks & Pierce, 2004, *Proceedings of the National Academy of Sciences of the United States of America*, 101(43), 15275-15278, R. Dirks & Pierce, 2012, U.S. Pat. No. 8,105,778) and G-quadruplex DNAzyme-based colorimetric detection. CHA amplification (*J. Am. Chem. Soc.*, 2013, 135 (20), pp 7430-7433). SMART signal amplification (Biotechniques 2002 March; 32(3):604-6, 608-11.)

Amplification products can be detected qualitatively (i.e., positive signal relative to control) or quantitatively (signal intensity related to absolute amount or relative amount of analyte giving rise to amplification product). Detection can include but does not require further analysis, such as sequencing of an amplification product. The methods provided by the invention may also include directly detecting a particular nucleic acid in a capture reaction product or amplification reaction product, such as a particular target amplicon or set of amplicons. Accordingly, mixtures of the invention can comprise specialized probe sets including TAQMAN™, which uses a hydrolyzable probe containing detectable reporter and quencher moieties, which can be released by a DNA polymerase with 5'→3' exonuclease activity (Livak, Flood, & Marmaro, 1996, U.S. Pat. No. 5,538,848); molecular beacon, which uses a hairpin probe with reporter and quenching moieties at opposite termini (Tyagi, Kramer, & Lizardi, 1999, U.S. Pat. No. 5,925,517); Fluorescence resonance energy transfer (FRET) primers, which use a pair of adjacent primers with fluorescent donor and acceptor moieties, respectively (Wittwer, Ririe, & Rasmussen, 2001, U.S. Pat. No. 6,174,670); and LIGHTUP™, a single short probe which fluoresces only when bound to the target (Kubista & Svanvik, 2001, U.S. Pat. No. 6,329,144). Similarly, SCORPION™ (Whitcombe, Theaker, Gibson, & Little, 2001, U.S. Pat. No. 6,326,145) and SIMPLEPROBES™ (Wittwer et al., 2003, U.S. Pat. No. 6,635,427) use single reporter/dye probes. Amplicon-detecting probes can be designed according to the particular detection modality used, and as discussed in the above-referenced patents. Other detection methods include: gel electrophoresis, mass spectrometry, or capillary electrophoresis, melting curve, nucleic acid-based fluorescent chelating dye such as SYBR™ green, or detection of amplification products using a fluorescent label and a soluble quencher (Will, Gupta, & Geyer, 2014, U.S. Pat. No. 8,658,366).

The term "multiplex amplification" refers to the amplification of more than one nucleic acid of interest. For example, it can refer to the amplification of multiple sequences from the same sample or the amplification of one of several sequences in a sample as discussed, for example, in George T. Walker, Nadeau, & Little, 1995 U.S. Pat. No. 5,422,252; and George T. Walker, Nadeau, Spears, et al., 1995, U.S. Pat. No. 5,470,723, which provide examples of multiplex strand displacement amplification. The term also refers to the amplification of one or more sequences present in multiple samples either simultaneously or in step-wise fashion.

The term "digital polymerase chain reaction" or "dPCR" refers to a refined version of conventional polymerase chain reaction (PCR) methods used to directly quantify and clonally amplify nucleic acids including DNA, cDNA or RNA, such that the amount of target nucleic acid can be directly quantitatively measured. Digital PCR achieves this direct quantitative measurement by partitioning individual target nucleic acid molecules present in a sample into multiple aliquots within many separate reaction chambers that are able to localize and concentrate the amplification product to detectable levels. Preferably, the sample is partitioned such that most aliquots (e.g., at least 50%, 75%, 90%, 95% or 99%) receive zero or one molecule of each target nucleic acid to be detected. After PCR amplification, the presence of a signal in any chamber is an indication the target nucleic is present and a count of chambers containing the PCR end-product is a direct measure of the absolute nucleic acid quantity. The capture or isolation of individual nucleic acid molecules, typically by way of dilution, may be effected in capillaries, microemulsions, arrays of miniaturized chambers, or on nucleic acid binding surfaces. The basic methodology of digital PCR is described in, e.g., Sykes et al., Biotechniques 13 (3): 444-449, 1992; and Vogelstein and Kinzler, Proc Natl Acad Sci USA 1999; 96:9236-41. Other forms of amplification described herein, such as transcription mediated amplification, can analogously be performed digitally.

The term "real-time amplification" refers to an amplification reaction for which the amount of reaction product, i.e. amplicon, is monitored as the reaction proceeds. Forms of real-time amplification differ mainly in the detection mechanisms used for monitoring the reaction products. Detection methods are reviewed in Mackay, Arden, & Nitsche, 2002, *Nucleic Acids Research*, 30(6), 1292-1305, which is incorporated herein by reference.

The term "detection label" refers to any atom or molecule which can be used to provide or aid to provide, a detectable (preferably quantifiable) signal, and can be attached to a nucleic acid or protein. Labels may provide signals detectable by fluorescence, radioactivity, colorimetry, gravimetry, magnetism, enzymatic activity and the like. Detection labels can be incorporated in a variety of ways: (1) the primers comprise the label(s), for example, attached to the base, a ribose, a phosphate, or analogous structures in a nucleic acid analog; (2) nucleotides triphosphates are modified at either the base or the ribose (or to analogous structures in a nucleic acid analog) with the label(s); the label-modified nucleotides are then incorporated into a newly synthesized strand by an extension enzyme such as a polymerase; (3) modified nucleotides are used that comprise a functional group that can be used (post-enzymatic reaction) to add a detectable label; (4) modified primers are used that comprise a functional group that can be used to add a detectable label in a similar manner; (5) a label probe that is directly labeled and hybridizes to a portion of the amplicon can be used; (6) a label that can be incorporated into amplified products; (7) a label that can react with byproducts of amplification reaction.

The terms "thermally cycling," "thermal cycling", "thermal cycles" or "thermal cycle" refer to repeated cycles of temperature changes from a total denaturing temperature, to an annealing (or hybridizing) temperature, to an extension temperature and back to the total denaturing temperature. The terms also refer to repeated cycles of a denaturing temperature and an extension temperature, where the annealing and extension temperatures are combined into one temperature. A totally denaturing temperature unwinds all double-stranded fragments into single strands. An annealing temperature allows a primer to hybridize or anneal to the complementary sequence of a separated strand of a nucleic acid template. The extension temperature allows the synthesis of a nascent DNA strand of the amplicon.

The term "reaction mixture", "amplification mixture" or "PCR mixture" refer to a mixture of components necessary to amplify at least one amplicon from nucleic acid templates. The mixture may comprise nucleotides (dNTPs), a thermostable polymerase, primers, and a plurality of nucleic acid templates. The mixture may further comprise a Tris buffer, a monovalent salt, and Mg'. The concentration of each component is well known in the art and can be further optimized.

The terms "amplified product" or "amplicon" refer to a fragment of DNA amplified by a polymerase using a pair of primers in an amplification method such as PCR.

The term "fluorophore" refers to a moiety that absorbs light energy at a defined excitation wavelength and emits light energy at a different defined wavelength.

The term "quencher" includes any moiety that is capable of absorbing the energy of an excited fluorescent label when it is located in close proximity to the fluorescent label and is capable of dissipating that energy. A quencher can be a fluorescent quencher or a non-fluorescent quencher, which is also referred to as a dark quencher. The fluorophores listed above can play a quencher role if brought into proximity to another fluorophore, wherein either FRET quenching or contact quenching can occur. It is preferred that a dark quencher which does not emit any visible light is used. Examples of dark quenchers include, but are not limited to, DABCYL (4-(4'-dimethylaminophenylazo) benzoic acid) succinimidyl ester, diarylrhodamine carboxylic acid, succinimidyl ester (QSY-7), and 4',5'-dinitrofluorescein carboxylic acid, succinimidyl ester (QSY-33), quencherl, or Black Hole Quencher® (BHQ-1, BHQ-2 and BHQ-3), nucleotide analogs, nucleotide G residues, nanoparticles, and gold particles.

The term "mutation" refers to one or more nucleotides in a target nucleic acid sequence that differ from a prototypical form of the target nucleic acid designated wildtype. The sequence designated wildtype is the most common allelic form of a sequence, the first discovered form of the sequence, and/or a form of the sequence associated with a normal (non-diseased phenotype). Single nucleotide polymorphisms (SNPs) are one form of mutation.

The term "surface" refers to any solid surface to which nucleic acids can be covalently attached, such as for example latex beads, dextran beads, polystyrene, polypropylene surface, polyacrylamide gel, gold surfaces, glass surfaces and silicon wafers. Preferably the solid support is a glass surface.

The term "attached to surface" refers to any chemical or non-chemical attachment method including chemically-modifiable functional groups. "Attachment" relates to immobilization of nucleic acid on solid supports by either a covalent attachment or via irreversible passive adsorption or via affinity between molecules (for example, immobilization on an avidin-coated surface by biotinylated molecules). The attachment must be of sufficient strength that it cannot be removed by washing with water or aqueous buffer under DNA-denaturing conditions.

A sticky end is a single-stranded end of a nucleic acid adjacent a double-stranded segment of the nucleic acid. Nucleic acids with stick ends with complementary sequences can anneal via the sticky ends and undergo ligation to one another.

An artificial sequence is a sequence lacking complementarity to or at least not intended to have complementarity to a naturally occurring target nucleic acid known or suspected may be present in a sample. Artificial sequences can serve as linkers joining segments hybridizing to a target nucleic acid, or as tails for labelling primers, among other purposes.

The term "chromosomal aneuploidy," refers to any genetic defect exhibiting an abnormal number of chromosomes. For example, chromosomal aneuploidy can include but is not limited to, including having more or fewer than normal number of any one chromosome, as well as having an extra portion of any one chromosome in addition to the normal pair, or missing a portion of any one chromosome in the normal pair. In some cases, the abnormality can involve more than one chromosome, or more than one portion of one or more chromosomes. Common chromosome aneuploidy diseases, include but are not limited to, trisomy, e.g., trisomy 21, where the genome of an afflicted patient has three rather than the normal two (i.e., a pair) chromosome 21. In rarer cases, the patient may have an extra piece of chromosome 21 (less than full length) in addition to the normal pair. In other cases, a portion of chromosome 21 may be translocated to another chromosome, e.g. chromosome 14. In this example, chromosome 21 is referred as the "chromosome relevant to the chromosomal aneuploidy" and a second, irrelevant chromosome, i.e., one that is present in the normal pair in the patient's genome, for example chromosome 1, is a "reference chromosome." There are also cases where the number of a relevant chromosome is less than the normal number of 2. Turner syndrome is one example of a chromosomal aneuploidy where the number of X chromosome in a female subject has been reduced from two to one.

A "genetic marker," refers to a polynucleotide sequence or a modification to a polynucleotide sequence present in the genomic sequence of a reference chromosome with a known physical location that permits identification. Examples of some genetic markers include but are not limited to, different alleles (e.g., alleles from two different individuals, such as alleles from a fetus v. alleles from the pregnant woman) to be distinguished from each other based on difference in the polynucleotide sequence (e.g., polymorphism), or presence or absence of the sequence at all (e.g., a sequence present on the Y chromosome from a male fetus but not present in the pregnant woman's genome). In this context, a "methylation marker" located on a chromosome relevant to the chromosomal aneuploidy refers to a genomic polynucleotide sequence on a chromosome having an abnormal number; or in the case where there is an extra piece of the chromosome or a portion of the chromosome is missing, the "methylation marker" is located within the piece or portion of the relevant chromosome. Difference in methylation profiles of the methylation marker allows distinction of the corresponding methylation marker from two different individuals, e.g., a fetus and the pregnant woman.

The term "single nucleotide polymorphism" or "SNP" refers to the polynucleotide sequence variation present at a single nucleotide residue among different alleles of the same gene, which may be the same gene located on the two copies of the same chromosome from the same individual (e.g., two alleles from a fetus) or may be the same gene from two different individuals (e.g., fetus and pregnant woman). This variation may occur within the coding region or non-coding region (e.g., the promoter region or its proximity, or the intron) of a gene, or in the intergenic region. Detection of one or more SNP allows differentiation of different alleles of a single gene.

The term "simple tandem repeat polymorphism" refers to the polynucleotide sequence variation demonstrated in the varying number of tandem repeats of a nucleotide sequence (e.g., a tandem repeat of 1 or more nucleotides) among different alleles of the same gene, which may be the same gene located on two copies of the same chromosome from the same individual (e.g., fetus) or may be the same gene from two different individuals (e.g., fetus and pregnant woman). This variation often occurs within the non-coding region (e.g., the promoter region or its proximity, or intron) of a gene, or in the intergenic region. Detection of difference in tandem repeat numbers allows differentiation of different alleles of a single gene.

The term "insertion-deletion polymorphism" refers to the polynucleotide sequence variation demonstrated in the presence or absence of a short nucleotide sequence (e.g., 1-3 nucleotides) among different alleles of the same gene, which may be the same gene located on two copies of the same chromosome from the same individual (e.g., fetus) or may be the same gene from two different individuals (e.g., fetus and pregnant woman). This variation can occurs within both the coding region and the non-coding region (e.g., the promoter region or its proximity, or intron) of a gene, or in the intergenic region. Detection of whether a short nucleotide sequence is present allows differentiation of different alleles of a single gene.

The term "blood" refers to a blood sample. The term encompasses whole blood or any fractions of blood, such as serum, cell-free DNA in blood plasma, and plasma as conventionally defined. Examples of blood samples include but are not limited to, preparation from a pregnant woman or a woman being tested for possible pregnancy, a person with a disease or infection monitoring for a possible disease or infection.

The term "bisulfite" refers to all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

The term "locus" refers to a segment of DNA defined by a start nucleotide position to an end nucleotide position on a chromosome (i.e., a genomic location, or a chromosomal location) of a reference genome assembly (e.g., the Human Genome March 2006 assembly (hg18) on the UCSC Genome Browser). A locus may or may not overlap with the genomic location of a gene, a CpG island, or any product of transcription/translation. For example, a locus usually can include but is not limited to a continuous segment of DNA identified by experimental data (e.g., a MeDIP-chip dataset) and the subsequent data analysis (e.g., MAT, TAS) to contain different DNA methylation levels. A locus may contain one or more CpG sites. A locus may be sub-divided into shorter segments (e.g., CpG-containing genomic sequences, fragments or regions) that are amenable to analysis (e.g., Epityper assay, bisulfite sequencing, polynucleotide amplification and determination). A locus may be developed into one or more fetal epigenetic markers. In some context of this application, a locus also refers to a continuous segment of DNA identified by certain bioinformatics criteria.

The term "molecular counting" refers to any method that allows quantitative measurement of the number of a molecule or molecular complex, often the relative number in the context of other co-existing molecules or complexes of distinct characteristics. Various methods of molecular counting are described in, e.g., Leaner et al., Analytical Chemistry 69:2115-2121, 1997; Hirano and Fukami, Nucleic Acids Symposium Series No. 44:157-158, 2000; Chiu et al., Trends in Genetics 25:324-331, 2009; and U.S. Pat. No. 7,537,897.

DETAILED DESCRIPTION

I. General Overview

Methods of amplification using primers of limited nucleotide composition are described by WO2016/172632, which claims the benefit of US62/152,752, filed Apr. 24, 2015, each incorporated by reference in its entirety for all purposes. The present discloses the use of such primers in digital amplification, for example, digital PCR.

II. Primer Design

The invention uses methods of amplification from a single primer or a pair of forward and reverse primers of limited nucleotide composition. Limited nucleotide composition means that the primers are underrepresented in at least one nucleotide type. Such primers have much reduced capacity to prime from each other or to extend initiated by mispriming from other than at their intended primer binding sites in a target nucleic acid. The use of such primers for target-specific amplification requires identification of primer binding sites in a target nucleic acid that support primer binding and amplification. In some target nucleic acids, primer binding sites having complete complementarity to primers of limited nucleotide composition can be identified. More often, segments of limited nucleotide composition in target nucleic acids are too short by themselves to serves as primer binding sites. However, such sites can be adapted to undergo amplification with primers of limited nucleotide composition by a variety of techniques described below including the use of ancillary toehold or junction oligonucleotide, primer with mismatch hybridization to primer binding site, mismatch stabilizing agents and presence of limited numbers of the underrepresented nucleotide in the primers as further described in WO2016/172632.

a. Basic Principles

The present method start with a basic concept of a limited nucleotide composition of primers in which one or more nucleotide type(s) is underrepresented (e.g., A, T, C and no G) and then selects the best primer binding sites within a target nucleic acid for pairing with primers of that composition (e.g., A, T and G). Depending on the primer binding sites selected, the nucleotide composition of the primers may then be further adjusted (e.g., by allowing a limited number units of an underrepresented nucleotide) to improve complementarity with to the primer binding sites.

A preferred primer design is that one and only one of the four standard nucleotide types is underrepresented in both the forward and reverse primers. In other words, such primers can consist of A, T/U and C with G underrepresented, A, T/U, G with C underrepresented, A, G and C with T underrepresented or T, G and C with A underrepresented. The underrepresented nucleotide type is preferably G or C. If the underrepresented nucleotide type is present at all in a primer, it is preferably at position(s) other than the 3' nucleotide, most preferably as the 5' nucleotide or a 5' tail nucleotide linked to the 5' nucleotide of the primer. Inclusion of a 5' underrepresented nucleotide increases the melting temperature (TM) of primer binding without significantly increasing in unintended amplification products.

The 3' nucleotide of a primer is preferably occupied by the complement of the underrepresented nucleotide type. For example, if the underrepresented nucleotide type is G, then the 3' nucleotide is preferably C and vice versa. The terminal C or G inhibits primer dimer extension because there is no complementary base on the primers for it to pair with. The elimination or underrepresentation of one nucleotide type substantially limits the number of nucleotides than can form Watson-Crick pairs between the primers or between primers and mismatched primer binding sites. Correct base paring of the 3' nucleotide of a primer is of greatest importance in its ability to support template dependent extension. Use of the complement of the underrepresented nucleotide type at this position substantially reduces primer dimer and primer mismatch extension.

Other features of primer design are similar to conventional primers. A primer has a sequence complementary to its primer binding site. Some primers are at least 15, 20, 25, 30, 35 or 40 nucleotides long. Some primers are no more than 25, 30, 40, 50 or 75 nucleotides long. Primers can have any permutation of these lower and upper lengths, e.g., from 15-50 of 20-30 or 30-40 nucleotides. The melting temperature of a primer to its primer binding site can be for example 45-80 C or preferably 55-65 C. By convention, for primers binding to opposite strands, one of which is the coding strand, the forward primer is complementary to the noncoding strand so the extended product is the coding strand, and the reverse primer to the coding strand so the extended product is the noncoding strand. For target nucleic acids not having coding and noncoding strands, designation of forward and reverse primer is arbitrary. Such is also the case when forward and reverse primers bind to primer binding sites on the same strand. Primers can have 5' tails not complementary to a target nucleic acid. Such tails can be used for attaching fluorophore or quenchers, or can contain identification codes, or can link discontinuous segments of primer complementary to its target nucleic acid.

Amplification conditions are usually similar to conventional primers in terms of buffers, $Mg^{2+}$, enzymes, temperatures and so forth. Conventional amplification is performed with all four standard nucleotide types present as dNTP monomers. Amplification with primers of limited nucleotide composition can be so performed, but can also be performed with the complements of the underrepresented nucleotide type(s) absent or present at reduced concentration or provided as ddNTP(s).

Usually but not invariably forward and reverse primers bind to opposite strands of a target nucleic acid. Thus, one strand of a target nucleic acid contains for example, the complement of the forward primer binding site and the reverse primer binding site, and the other strand contains the forward primer binding site and complement of the reverse primer binding site. In some formats, forward and reverse primer binding sites are on the same strand. For example, linked forward and reverse primers can bind to binding sites on the same strand and amplify by a rolling circle mechanism. Some pairs of three way junction primers can also bind to sites on the same nucleic acid strand, such that one primer serves as a template for the other.

The search for suitable primer binding sites in a target nucleic acid is informed by the principles of primer design in that the primer binding sites should be complementary to the primers. For example, for use with primers that are underrepresented in a single nucleotide type, one can search a target nucleic acid for a forward primer binding site and a reverse primer binding site that are underrepresented in the complement of the nucleotide type underrepresented in the primers. Preferably, a forward primer binding site and a reverse primer binding site are identified in which the complement of the underrepresented nucleotide type is absent. However, if such sites cannot be found, other primer binding sites can be still be used, preferably those in which the number of units of the complement of the underrepresented nucleotide type is minimized. Often, the complement of the underrepresented nucleotide type in the primers is itself underrepresented in the primer binding sites, but this is not essential. Some forward and reverse primer binding sites each have no more than 4, 3, 2 or 1 units of the complement of the nucleotide underrepresented in the primers.

For ATC primers, software can be used to look for contiguous or proximate ATC and ATG regions representing the complement of the forward primer binding site and reverse primer binding site respectively. To use ATG primers, software can look for ATG and ATC regions for the complement of the forward primer binding site and the reverse primer binding site respectively. To use CGA primers, software can look for CGA and CGT regions representing the complement of the forward primer binding site and the reverse primer binding site respectively. To use CGT primers, software can look for CGT and CGA regions for the complement of the forward primer binding site and the reverse primer binding site respectively.

The complement of the forward primer binding site (or the forward primer binding site itself if on the same strand as the reverse primer) and the reverse primer binding site can be contiguous with one another or separated by intervening nucleotides in a strand of the target nucleic acid. The intervening nucleotides, if any, may exclude the underrepresented nucleotide in the primers and its complement, or may include one or both of these nucleotides and either of the other two of the four standard nucleotide types. If non-contiguous, the complement of the forward primer binding site (or the forward primer binding site itself) and reverse primer binding site should be close enough together to prime extension compatible with the amplification technique (e.g., no more than 100, 500, 1000, or 10000 nucleotides).

FIG. 1 shows a simple representation of the method in which the forward and reverse primers each consist of A, T and C nucleotides, with a C nucleotide at the 3' positions. In other words G is the underrepresented nucleotide type. The reverse primer binding site consists of A, T and G (the complement of the C, and underrepresented in the primers). The complement of the forward primer binding site shown consists of A, T and C, implying that the forward primer binding site (like the reverse primer binding site) consists of A, T and G. The forward and reverse primers are perfectly complementary to the forward and reverse primer binding sites, respectively. The complement of the forward primer binding site and the reverse primer binding sites are contiguous. An amplification product can form when a reaction is supplied with the three nucleotide triphosphate monomers complementary to the three-nucleotide-types in the forward and reverse primers, A, T and G. Primer dimer formation and mispriming are inhibited as described because few bases can pair between primers and or between a primer and a mismatched primer binding site. But even if the primers could sufficiently bind to unintended primer binding sites sufficient to initiate extension, no amplification product would form because the omitted nucleotide triphosphate monomer in the amplification mix brings amplification to a stop whenever the extended chain need to incorporate a C.

Figure 4:
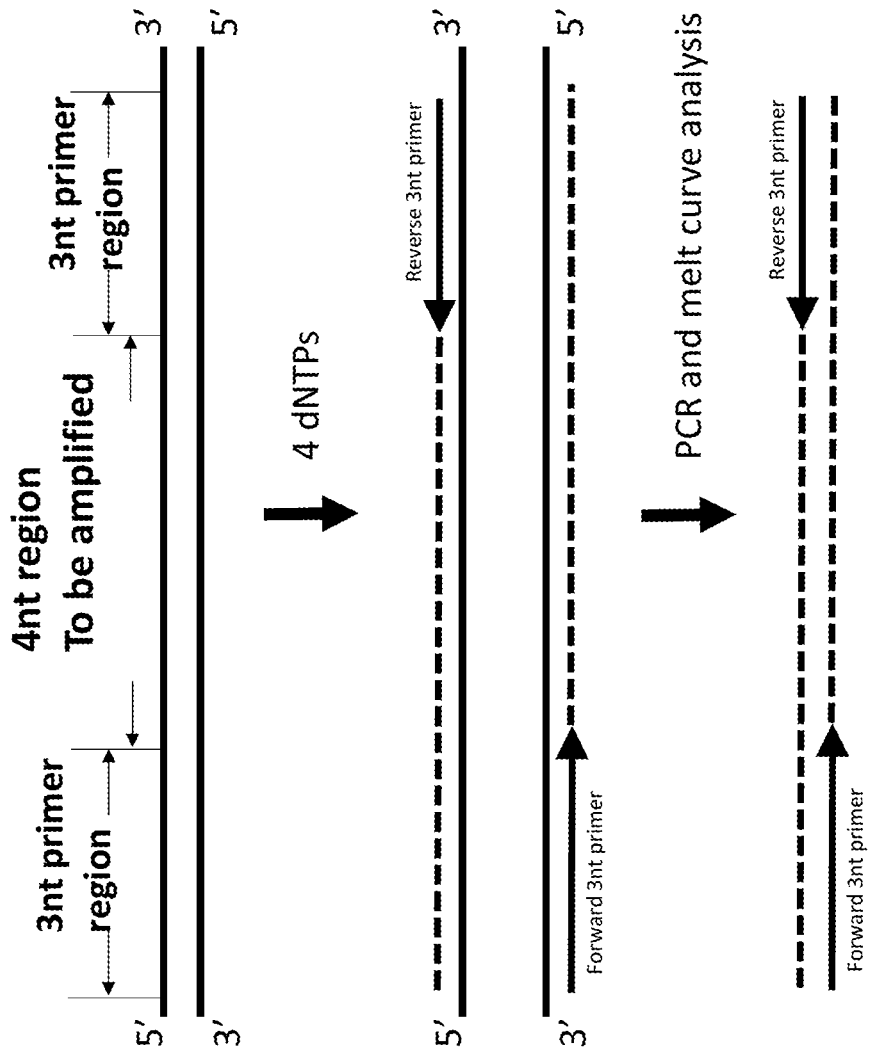
FIG. 4 shows amplification of a template in which three nucleotide-type primer binding sites are separated by a segment including all four-nucleotide-types. Amplification is performed in the presence of all four-nucleotide-types mononucleotide triphosphates.

Alternatively, the primer binding sites can be noncontiguous and separated by a region including all four of the standard nucleotides, as shown in FIG. 4. In such a case, amplification is performed with all four of the standard nucleotide triphosphate monomers.

b. Mismatches Between Primer Binding Sites and Primers

FIG. 2 shows a more typical situation in which a search of a target nucleic acids for forward and reverse primer binding sites showed no suitable pair of forward and reverse prime binding sites having complete complementarity to primers consisting of A, T, C nucleotides (i.e., no primer binding sites in which the underrepresented nucleotide type is entirely absent). The longest ATC region contains 7 nucleotides (CATCCTC) and the longest ATG region (GGATTGGTATTG) contains 12 nucleotides (nucleotides 35-46 of SEQ ID NO:72). These regions are not long enough to use as primers because their Tm's are too low. In such cases, primers mismatched with the primer binding sites can be used. In FIG. 2 the forward primer binding site has three units of C and the reverse primer binding site has two units of C aligned with C-nucleotides in the primers. Accordingly when such primers and primer binding sites are hybridized with one another there are three mismatch positions between forward primer and its binding site and two mismatches between the reverse primer and its binding site. Nevertheless hybridization and extension can still occur albeit with reduced efficiency. Hybridization and extension can be increased if the reaction mix is supplied with a mismatch stabilizing agent. Mismatch binding or stabilizing agent are any molecules or any modification in underrepresented primers that can stabilize the underrepresented primer hybridization with underrepresented primer binding sites through chemical interaction or physical interaction (se FIG. 3). Modification of underrepresented primers may be modified in any way, as long as a given modification is compatible with the desired function of a given underrepresented primers as can be easily determined. Modifications include base modifications, sugar modifications or backbone modifications, such as PNA, LNA, or 2' Fluorine 2' methyloxy. Rhodium metalloinsertors as examples of mismatch stabilizing agents are described by Ernst et al. J. Am. Chem. Soc. 131, 2359-2366 (2009). Chemicals such as rhodium metalloinsertors can specifically bind DNA mismatches and have a binding constant of $2.0 \times 10^7$ $M^{-1}$ at a CC mismatch. Binding of rhodium metalloinsertors can increase the melting temperature of double-stranded DNA including a mismatch by 18.7° C. Therefore such mismatch binding reagents can be added to three-nucleotide-type primer PCR reactions to specifically stabilize mismatches and increase PCR efficiency. As well as C—C mismatches, T-C or A-C mismatches can be stabilized by such reagents among other possibilities. Even with such stabilizing agents, mismatched primers may hybridize to a template with slightly reduced efficiency but amplification can proceed.

c. Inclusion of a Few Units of Underrepresented Nucleotide

Alternatively or additionally to using a mismatch stabilizing agent, the number of mismatches can be reduced by introducing a limited number of units of the underrepresented nucleotide type (typically up to 2 internal position) at positions in a primer that reduce the number of mismatches with its primer binding site. An underrepresented nucleotide can also be used at the 5' position of the primer or in a tail immediately 5' to the 5' end of the primer. For example, with the primers and primer binding sites shown in FIG. 2, introduction of two G's into each of the forward and reverse primers reduces the mismatches to one in the case of the forward primer and none in the case of the reverse primer.

The choice whether to use a mismatch stabilizing agent or to include one or more units of the underrepresented nucleotide type in the primers depends on the number of mismatch positions between hypothetical forward and reverse primers completely lacking the underrepresented nucleotide types and their respective binding sites. If there are more than two mismatches between such a primer and its binding site or a mismatch occurs close (e.g., within 4 nucleotides) to the 3' end of a primer, it is preferred to eliminate one or more mismatches by inclusion of one or more underrepresented nucleotides in the primer.

In the case of ATC primers, instead of introducing G into the underrepresented primer, one or more unnatural bases can be introduced as alternative as long as the unnatural bases can help to reduce primer dimer interaction comparing to conventional ATGC primers. An example of the unnatural bases is inosine. Introducing G increases the hybridization efficiency of primer to its binding site, but also increases inter- and intra-primer interactions because CG pairs are present now. Inosine on the other hand maintains the hybridization efficiency of primer to its binding site with the help of flanking bases pairs. But a single or a few of C and I pairs between or within primers make little contribution to binding and do no result in substantial primer dimer formation. Preferably such primers consist of a 3' segment that contains only A, T, and C to minimize the mismatch effect on primer extension efficiency, and a 5' segment including only any number of inosine residues (e.g., 1-10)

In situations in which the primer binding sites are not perfectly matched with primers in which an underrepresented nucleotide type is entirely absent, the amplification can still occur without the complement of the underrepresented nucleotide type in the primers being supplied as a nucleotide triphosphate monomer, but proceeds more efficiently if this nucleotide type is supplied. This nucleotide type can however by supplied at reduced concentration compared with the others of the standard four nucleotides (e.g., <10×, <100× or <1000× each of the other nucleotide triphosphate monomers), or can be supplied as a dideoxy NTP. Extension resulting from mispriming is terminated by the dideoxy NTP. Use of either strategy (reducing nucleotide concentration or use of ddNTP) decreases unintended amplification products from mispriming or primer dimers. The primers with inosine substitutions require dCTP in the reaction for efficient extension on the inosine bases. The dCTP however can be supplied at reduced concentration compared with the other types of nucleotide triphosphate monomers.

When target sequences are from organisms of a variety of species or genotypes, the template is a mixture of more than one allele. Primer with underrepresented nucleotide can contain degenerate bases at certain positions to match different sequence variations.

Underrepresented primers with mismatches or inosine substitutions can be used in combination with the conventional primers of their original sequences (i.e. no mismatches or inosine substitutions) in amplification reactions. However, a conventional primer should have reduced concentrations, between 0.1% to 50% of an underrepresented primer's concentration. The conventional primers hybridize to their binding sites more efficiently than the underrepresented primers and their extension products provide the underrepresented primers with more templates. The types of dNTP which are complement of the underrepresented nucleotide are provided at reduced concentrations as mentioned above or are completely omitted depending on the composition of the underrepresented primers. Such combination of conventional and underrepresented primers facilitates the amplification from underrepresented primers and maintains the low primer-primer interactions.

d. Primers Underrepresented in More than One Nucleotide Type

The strategy and principles for primers with a single underrepresented nucleotide type can be applied to primers or with two or even three underrepresented nucleotides can be applied to primers (or in other words consisting entirely or primarily of a single nucleotide). Use of primers underrepresented in a single nucleotide has wider applicability in natural target nucleic acids because binding sites for such primers occur at statistically greater frequency. However, some forms of amplification, such as immune-PCR, amplify nucleic acids of artificial sequences. Such artificial sequences can be designed to be amplified with primers with two or even three underrepresented nucleotide type as with one underrepresented nucleotide type.

In primers underrepresented in two nucleotide types, the two underrepresented nucleotide types should not be complementary to one another. In others words, the underrepresented nucleotide types can be A with C, A with G, T/U with C or T/U with G. This leaves primers consisting entirely or primarily of the same two noncomplementary nucleotide types. Such primers have reduced ability to support primer-dimer or primer-mismatch extension. Primers have three nucleotides underrepresented or in other words, consisting entirely or substantially of a single nucleotide type also have reduced ability to support primer dimer or mismatched primer extension. Primer binding sites are selected by analogous principles to those described above, and primer sequences can be adjusted to accommodate a small number of underrepresented nucleotide(s) if necessary. Toehold and junction primer strategies can also be used as described in WO2016/172632. Amplification with such primers is performed at least with the complements of the nucleotides not underrepresented in the primers, and optionally, with the complements of the underrepresented nucleotide(s) as well, which as noted can be supplied in reduced concentration or as dideoxy nucleotides.

III. Sample Preparation

A target nucleic acid can be prepared from various biological samples of interest. Examples of samples include but are not limited to, fetal or maternal genetic material, maternal plasma or blood, a biopsy sample of a subject having a cancer or being suspect of having a cancer, any human of known or unknown status with respect to genetic variations, blood cells, blood cells enriched for (a) particular cell type(s), bone marrow derived mononuclear cells, placenta cells, umbilical cord sample, fetal tissue, fetal fibroblasts or blood cells, tissue from infant or child, neonatal tissue, non-cellular entity comprising nucleic acid (e.g. virus), cell-based organisms (e.g. plant, fungi, eubacteria, archeabacteria, protist, or animal), plants or food products.

Before analyzing the sample using the methods provided herein, it may be desirable to perform one or more sample preparation operations on the sample. Examples of sample preparation operations may include extraction of intracellular material from a cell, tissue, blood, or microorganisms. Extracted intracellular material can include nucleic acids, protein, or other macromolecules from the samples. In some applications, a sample is prepared using formalin-fixed, paraffin embedded (FFPE), or frozen section for sectioning. In some applications the sample is microdissected with a laser before any extraction methods are used. Another example of sample preparation operations may include extraction of cell free DNA from plasma or blood.

A biological sample can be obtained by methods known in the art including swabbing, scraping, phlebotomy, a biopsy (e.g., excisional, fine needle aspiration, incisional, core needle), or any other suitable method particularly for subjects having or suspected of having a disease or infection. In some applications, serial biopsies are obtained from a diseased tissue or organ.

Biological samples can be obtained from any of the tissues provided herein. Examples of biological samples include but not limited to, lung, respiratory tract, nasal cavity, gastrointestinal tract, mouth, skin, heart, lung, kidney, breast, pancreas, liver, blood, muscle, smooth muscle, bladder, gall bladder, colon, intestine, brain, prostate, esophagus, or thyroid.

a. Nucleic Acid Extraction

For whole cells, viruses or other tissue samples to be analyzed, nucleic acids are typically extracted from these samples.

The target nucleic acid can be isolated from the biological samples using any techniques known in the art. In some applications, DNA or RNA can be extracted from a biological sample before analysis by either physical, chemical methods, or a combination of both. Extraction can be by means including, but not limited to, the use of detergent lysates, sonication, or vortexing with glass beads. In particular embodiments, DNA can be extracted according to standard methods from blood, e.g., with the use of the Qiagen UltraSens DNA extraction kit. In some applications, nucleic acid molecules can be isolated using gradient centrifugation (e.g., cesium chloride gradients, sucrose gradients, glucose gradients), centrifugation protocols, boiling, purification kits (e.g., Qiagen purification systems; Promega purification systems; Amersham purification systems; Invitrogen Life Technologies Purification; Mo-Bio Laboratories purification systems, etc.). Methods of extracting nucleic acids can also include the use of liquid extraction using Trizol or DNAzol.

RNA can be isolated from various body fluids. Methods of isolating RNA analysis from blood, plasma and serum. See, for example Tsui N B et al. *Clin. Chem.* 48, 1647-53, 2002.

In some applications, the target nucleic acid is prepared from an RNA using RT-PCR. In some applications, the target nucleic acid is prepared by an RT-PCR and following dPCR, which can be carried out in two distinct steps or a single step. In some applications, the target nucleic acid is pre-amplified in a separate reaction to specifically or non-specifically enrich the target sequences of interest.

IV. Amplification Methods

The strategy and principles described above can be incorporated into any amplification method involving template-directed extension from single or paired primers. The polymerase chain reaction is one implementation including optionally RT-PCR. PCR is characterized by temperature cycling to permit primer annealing, primer extension and denaturation of an extended strand from its template.

Transcription mediated amplification (TMA) is an alternative isothermal form in which one or both of the primers is linked to a promoter at its 5' end, usually a T7 promoter. Once the double-stranded promoter is formed, the RNA polymerase starts transcription amplification. The amplification product is single stranded RNA molecules. TMA can also be coupled to reverse transcription.

Another isothermal amplification format amenable to use with primers of the invention is the nicking amplification reaction (NEAR). NEAR exponentially amplifies DNA at a constant temperature using a polymerase and nicking enzyme. The primers for nicking amplification are linked to artificial segments at their 5' ends, the 5' segments containing a cleavage site for the nicking enzyme. In the first cycle both primers hybridize to a template and extend. In the next cycle, both primers can hybridizes to the first cycle products and extend to generate the full nicking site on the artificial tail. Once a nicking site is formed, nicking enzyme nicks and releases one strand. Extension and nicking repeat in the next cycle.

Another isothermal amplification procedure amenable to use with primers of the invention is loop mediated isothermal amplification or (LAMP). LAMP uses one or more primers having underrepresented nucleotides in accordance with the invention. In LAMP, the target sequence is amplified at a constant temperature of 60-65° C. using either two or three sets of primers and a polymerase with high strand displacement activity in addition to a replication activity. Typically, 4 different primers are used to identify 6 distinct regions on the target gene, which adds highly to the specificity. An additional pair of "loop primers" can further accelerate the reaction.

Another isothermal amplification format is Recombinase Polymerase Amplification (RPA) is a single tube, isothermal alternative to the Polymerase Chain Reaction (PCR). The RPA process employs three core enzymes—a recombinase, a single-stranded DNA-binding protein (SSB) and strand-displacing polymerase. Recombinases are capable of pairing oligonucleotide primers with homologous sequence in duplex DNA. SSB bind to displaced strands of DNA and prevent the primers from being displaced. Finally, the strand displacing polymerase begins DNA synthesis where the primer has bound to the target DNA. By using two opposing primers, much like PCR, if the target sequence is indeed present, an exponential DNA amplification reaction is initiated. The two primers can both be primers with underrepresented nucleotide types as described above.

Still other amplification format in which primers of the invention can be used include strand displacement assay, transcription-based amplification systems, self-sustained sequence replication (3SR), a ligation chain reaction (sometimes referred to as oligonucleotide ligase amplification OLA), cycling probe technology (CPT), rolling circle amplification (RCA), Recombinase Polymerase Amplification (RPA), nucleic acid sequence bases amplification (NASBA), invasive cleavage technology, Helicase dependent amplification (I), Exponential amplification (EXPAR), Hybridization chain reaction (HCR), and catalyzed hairpin assembly (CHA).

Another amplification format is immune-PCR in which an analyte is linked to a nucleic acid (which can have an artificial sequence) and the analyte is detected by amplification of the nucleic acid. Such amplification can be performed with a primer pair with underrepresented nucleotide types (e.g., completely absent) complementary to primer binding sites underrepresented in the complements of the underrepresented nucleotide(s).

The above methods amplify a specific predetermined target nucleic acid or segment thereof determined by the selected primers and their complementary primer binding sites (in other words, target-specific amplification). The amplification product from a pair of primers binding to its intended primer binding sites predominates over any or all other amplification products primed from the same primer pair either by primer dimer binding or mispriming on the target sequence. Preferably the amplification product from primers binding to their intended primer binding sites is present in at least 10, 50, 100 or 1000 fold excess (by moles, mass or copy number) of any or all other amplification products primed from the primer pair. In some methods, a single pair of primers is used in amplification. In other methods, multiple primer pairs are used in a multiplex amplification. The number of primer pairs can be for example 2-50 or more, preferably 5-25 or 10-20, or at least 2, 3, 4, 5, 6, 7, 8, 9, 10, 11, 12, 13, 14, 15, 16, 17, 18, 19 or 20. When multiple primer pairs are used the intended amplification product of each primer pair from binding of the primer pair to its intended primer binding sites is present in at least 10, 50, 100 or 1000 fold excess (by moles, mass or copy number) to any or all other amplification products primed by that primer pair. When multiple primer pairs are present in the same reaction, preferably each primer of each primer pair has the same underrepresented standard nucleotide type or types. Preferably one and only one standard nucleotide type is underrepresented in each primer of each primer pair. Primers used in the methods are not random primers in which most or all primer positions are occupied by random or degenerate selections of nucleotides varying among primers. Rather each primer pair is designed to hybridize to specific primer binding sites in a target nucleic acid, and typically different primer pairs are unrelated from each other as required by the different primer binding sites in target nucleic acids being detected. For example, one primer pair can be designed to bind to primer binding sites on a target nucleic acid in one pathogen and a second primer pair to primer binding sites on a different target nucleic acid in a different pathogen. Except by coincidence the different target nucleic acids and consequently primer binding sites and primers are unrelated to one another.

V. Digital Amplification

Digital amplification (e.g., digital PCR or dPCR) is a highly sensitive quantitation method for nucleic acids. The method can detect and quantify nucleic acids by directly measuring the number of target molecules without relying on any normalization standard or external standards. In this manner, the absolute number of target molecules can be determined, with a lower limit being a single copy of the molecule.

The strategy used by dPCR or analogously other form of digital amplification can be referred to as "Divide and Conquer" strategy where a sample can be first diluted and divided into thousands to tens of thousands of micro reaction chambers, so that most reaction chambers (e.g., at least 50%, 75%<90%, 95 or 99%) contains only either zero or one copy of the target gene sequence (a small number of reaction chambers may contain multiple copies). By counting the number of reaction chambers with positive amplification results, the absolute number of target gene molecules in the original sample can be determined.

The distribution of the target molecules across the partitions can be seen as a Poisson process (the targets end up in partitions independently and with a fixed rate). Poisson statistics thus allow a more accurate calculation of the initial number of targets from the number of positive and negative partitions taking into account that some reaction chambers receive multiple copies.

In comparison to traditional PCR technology, dPCR or other digital amplification method is considered to have multiple advantages, including low required sample amount, reduced consumption of reagents, absolute quantification of nucleic acid molecules, reduced interference among different copies within a sample, and superb sensitivity and specificity. Furthermore, the standard division process of the reaction system in digital amplification can greatly reduce the concentration of background sequences that could compete with the target sequence; therefore, digital amplification may be especially suitable for detection of rare mutations in a complex biological background, such for example DNA from circulating tumor cells and cffDNA for NIPT (non-invasive prenatal testing) applications.

a. Digital Amplification Primers

Digital amplification amplifies a single copy of a template. Like traditional or first-generation PCR, digital amplification also requires a high concentration of primers in the reaction mix. However, having a high concentration primers results in the production of non-targeted products, such as primer-dimer or non-specific amplifications.

Non-targeted primer-dimer products tend to have a smaller size than the intended amplification product, and owing to their small size are amplified with higher efficiency than the intended product. This creates competition within the reaction between these products and in many cases the intended amplification products cannot be differentiated from the non-targeted primer-dimer products, where the reaction is monitored by DNA intercalating dyes. Consequently, primer dimer formation hinders the efficiency, sensitivity, and specificity of digital amplification. Furthermore, the problem of primer-dimer formation and non-specific amplification becomes significantly more pronounced as more primers are multiplexed in high-throughput digital amplifications.

These types of problems can be reduced or avoided by performing digital PCR or other amplification with limited composition primers as described herein. Such primers can increase efficiency, sensitivity, and specificity of in the digital amplification.

Figure 5:
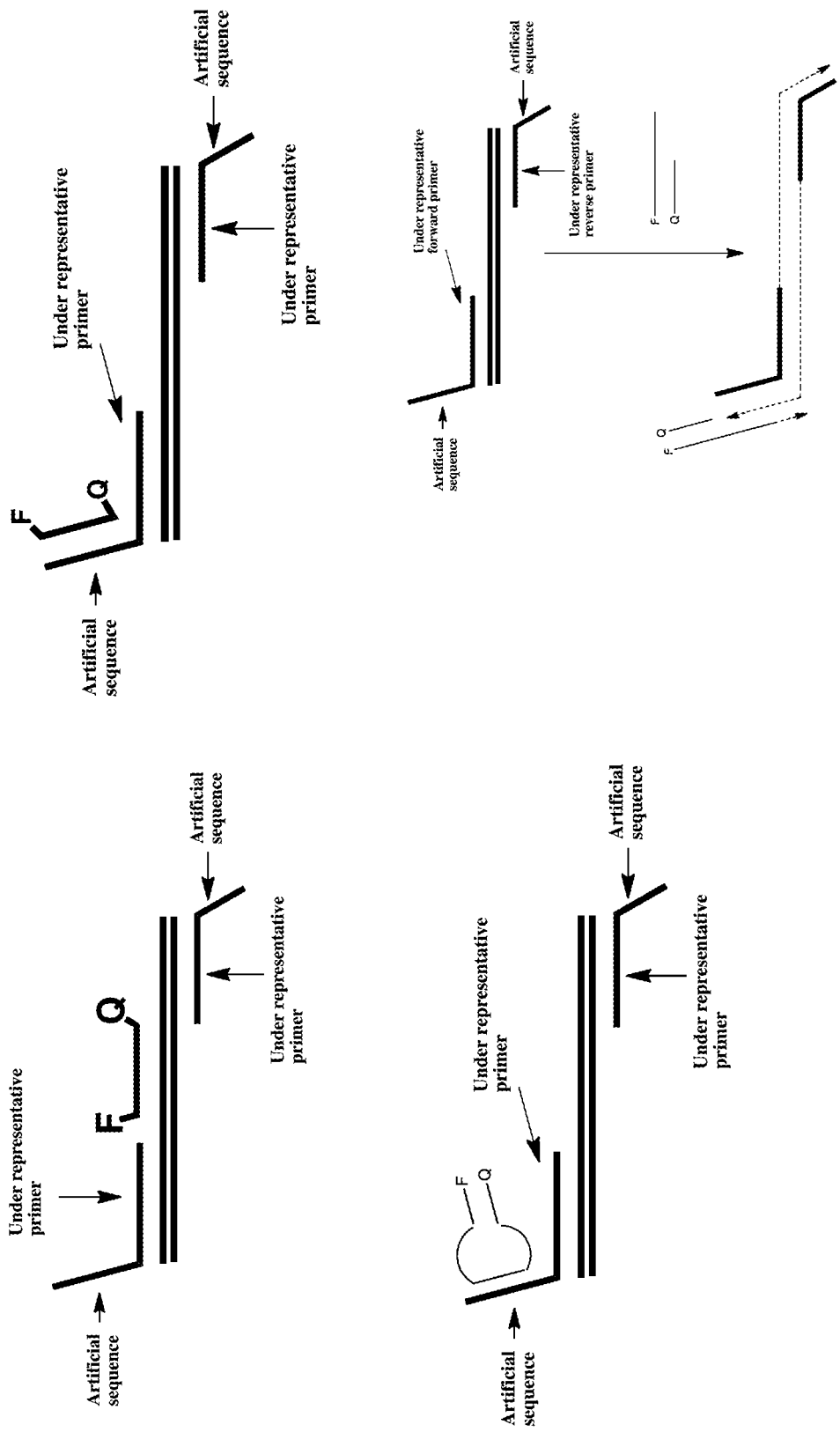
FIG. 5 shows primers with underrepresented nucleotide types attached to fluorophores suitable for digital amplification.

Any of the primers described herein by used for a digital amplification. FIG. 5 shows examples of primers with an underrepresented nucleotide type comprising fluorophore labeled probes which can be used in a digital amplification.

In some applications primers with an underrepresented nucleotide type provided herein can be linked to a peptide nucleic acid (PNA) for higher sensitivity.

In some applications, the primers of limited nucleotide composition reduce primer dimer formation in a single or multiplex digital amplification by greater than 70%, 75%, 80%, 90%, 95%, 97%, or 99% compared with an otherwise comparable reaction with conventional primers.

b. dPCR Platforms

The compositions, methods, and kits can be used with various commercial dPCR platforms currently know or developed in the future.

Depending on the application a clinician or researcher can choose a dPCR platform that meet its technical demands of required throughput and accuracy requirements or its application. For example, a microfluidic-chip-based dPCR can have up to several hundred partitions per panel. Droplet-based dPCR usually has approximately 20,000 partitioned droplets, but it can have up to 10,000,000.

In some application the dPCR compositions and methods provided by the disclosure can be used with microfluidic-chip-based dPCR. In some application the dPCR compositions and methods provided by the disclosure can be used with Droplet-based dPCR.

In some applications the dPCR compositions and methods provided by the disclosure can be used with microfluidic-chamber-based BioMark® dPCR from Fluidigm. In some applications the dPCR compositions and methods provided by the disclosure can be used with micro-well chip-based QuantStudio12k flex dPCR. In some applications the dPCR compositions and methods provided by the disclosure can be used with 3D dPCR from Life Technologies. In some applications the dPCR compositions and methods provided by the disclosure can be used with droplet-based ddPCR (ddPCR) QX100 and QX200 from Bio-Rad®. In some applications the dPCR compositions and methods provided by the disclosure can be used with RainDrop from RainDance®.

In some applications, the methods provided herein enhance accuracy of quantification or detection in a dPCR reaction by greater than 70%, 75%, 80%, 90%, 95%, 97%, or 99% relative to otherwise comparable assays with conventional primers not containing an underrepresented nucleotide. In some applications, the methods provided herein enhance sensitivity of quantification or detection in a dPCR reaction by greater than 70%, 75%, 80%, 90%, 95%, 97%, or 99% relative to otherwise comparable assays with conventional primers.

Other forms of digital amplification can be performed with the same or similar platforms.

c. Multiplexing dPCR Assays

Digital PCR or other amplification can be performed as a multiplex. A multiplex assay is particularly useful in applications were the biological material is limited or rare so that splitting the sample for separate analysis is infeasible or difficult. In some cases, the multiplex amplification assay enables the detection of quantification of at least 2, 3, 4, 5, 6, 7, 8, 9, 10, 11, 12, 13, 14, 15, 16, 17, 18, 19, 20, 21, different genetic variations, such as single nucleotide polymorphisms (SNPs), insertions, inversions, rearrangements, transversions, deletions, indels, microsatellite repeats, minisatellite repeats, short tandem repeats, transposable elements, large scale structural chromosomal variants, methylation, and combinations thereof. In some applications, the genetic variations assayed are a combination of different genetic variations.

In some applications, the multiplexing dPCR enables detection of least 2, 3, 4, 5, 6, 7, 8, 9, 10, 15, 20, 25, 30, 40, 50, 60, 70, 80, 90, or 100 different genetic alternations in a single reaction tube. In some applications, the multiplexing dPCR enables detection of least 100, 200, 300, 400, 500, 600, 700, 800, 900, or 1000 different genetic alternations in a single reaction tube.

d. Detection Methods

Amplification reactions used with the methods, compositions, and kits of the disclosure can generate one or more signals. In some applications, labels are used in or after the amplification reaction to generate the signal. In some applications, dyes are used in or after the amplification reaction to generate the signal.

In some applications, the target nucleic acid is detected with DNA intercalating dye. Examples of intercalating dyes that can be used with the disclosure include but are not limited to, ethidium bromide, propidium iodide, acridine orange, 9-amino-6-chloro-2-methoxyacridine (ACMA), SYBR™ Green, SYBR™ Green II, SYBR™ Gold, YO (Oxazole Yellow), TO (Thiazole Orange), PG (PicoGreen®), or EvaGreen®. Positive dPCR reactions are distinguished from negative dPCR reactions by their elevated signal intensity over the background signal generated by primers.

In some applications, multiple target nucleic acids or genetic variants are detected simultaneously in one dPCR reaction. In some applications, multiple targets are two or more alleles of the same target locus. In some cases, multiplex targets are different target locus. The reaction mixture comprises two or more primer pairs, each pair comprising a forward primer and a reverse primer. By varying the lengths of amplified products and/or primer concentration, the different targets can be discriminated by their signal intensity of amplified products. The space between background signal generated by primers alone and the saturation signal intensity limited by dPCR machine determines how many targets can be multiplexed in one dPCR reaction. The three-nucleotide-type primers (3N primers) greatly reduce primer-primer interaction, and thus reduce the background signal, allowing more targets to be multiplexed. In some embodiments, multiple amplicons are detected for quantification of one target. The three-nucleotide-type primers (3N primers) greatly increase dPCR multiplicity allowing accurate quantification where the target nucleic acid in at extremely low amounts in the biological sample.

In some applications, the target nucleic acid of the dPCR is detected with fluorophore labeled probes, such as Taqman probe, Molecular Beacon, and fluorophore labeled primers provided with a quencher labeled complementary oligo (FIG. 5). In another embodiment, the target nucleic acid of the dPCR is detected with a combination of DNA intercalating dyes and fluorophore labeled probes.

A "fluorescent label" or "fluorophore" can be a compound with a fluorescent emission maximum between about 350 and 900 nm.

Examples of fluorophores used with the disclosure include but are not limited to, 5-FAM (also called 5-carboxyfluorescein; also called Spiro(isobenzofuran-|(3H)' 9'-(9H)xanthene)-5-carboxylic aci',3',6'-dihydroxy-3-oxo-6-carboxyfluorescein); 5-Hexachloro-Fluorescein; ([4,',2',4',5',7'-hexachloro'(3',6'-dipivaloyl-fluorosceinyl)-6-carboxyli-c acid]); 6-Hexachloro-Fluorescein; ([4,',2',4',5', 7'-hexachloro'(3',6'-dipivaloylfluorosceinyl)-5-carboxylic acid]); 5-Tetrachloro-Fluorescein; ([4,',2',7'-tetra-chloro'(3', 6'-dipivaloylfluoresceinyl)-5-carboxylic acid]); 6-Tetrachloro-Fluorescein; ([4,',2',7'-tetrachloro'(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS-5-((2-aminoethyl) amino)naphthalene-l-sulfonic acid); 1,5-IAEDANS (5-((((2-iodoacetyl)amino)ethyl)amino)naphthalene-l-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-pr-oprionic acid); Quasar™-670 dye (Biosearch Technologies); Cal Fluor™ Orange dye (Biosearch Technologies); Rox dyes; Max dyes (Integrated DNA Technologies), as well as derivatives thereof.

A "quencher" can be a molecule or part of a compound, which is capable of reducing the emission from a fluorescent donor when coupled to or in proximity to the donor. Quenching can occur by any of several mechanisms including fluorescence resonance energy transfer, photo-induced electron transfer, and paramagnetic enhancement of intersystem crossing, Dexter exchange coupling, and exciton coupling such as the formation of dark complexes.

Fluorescence can be "quenched" when the fluorescence emitted by the fluorophore is reduced as compared with the fluorescence in the absence of the quencher by at least 10%, for example, at least 15%, 20%, 25%, 30%, 35%, 40%, 45%, 50%, 55%, 60%, 65%, 70%, 75%, 80%, 85%, 90%, 95%, 98%, 99%, or more. The selection of the quencher can depend on the identity of the fluorophore. Examples of quenchers used with the disclosure include but are not limited to, DABCYL, Black Hole™ Quenchers (BHQ-1, BHQ-2, and BHQ-3), Iowa Black™ FQ and Iowa Black™ RQ.

In some applications, both a fluorophore and a quencher can be coupled to the primer using methods known in the art. In general, a fluorophore can be coupled to the 5' portion of a hot-start primer 5' of the cleavage site. Fluorophores can be added during oligonucleotide synthesis through standard phosphoramidite chemistry. They can also be added post synthesis by introducing a linker with an appropriate functional group during oligo synthesis. Following synthesis, the fluorophore can be coupled to the oligonucleotide functional group. For longer sequences, to permit efficient quenching, the sequence immediately 3' of the fluorophore and outside the target region of the primer can be made to be partially complementary to permit the formation of a stem-group of a hairpin (i.e., molecular beacon). Thus, the fluorophore can remain with the primer while the primer is hybridized to the target polynucleotide and extended by the polymerase. The quencher can be coupled to the 3' portion of the hot-start primer 3' of the cleavage site. Thus, the quencher can be released from the primer while the primer is hybridized to the target polynucleotide and thus no longer quench the fluorophore that remains coupled to the primer. The proper site of coupling a fluorophore and quencher and the distance between the fluorophore and the quencher can be known in the art. In some cases, a fluorophore is positioned about, more than, less than, or at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases from a quencher in a primer.

Figure 6:
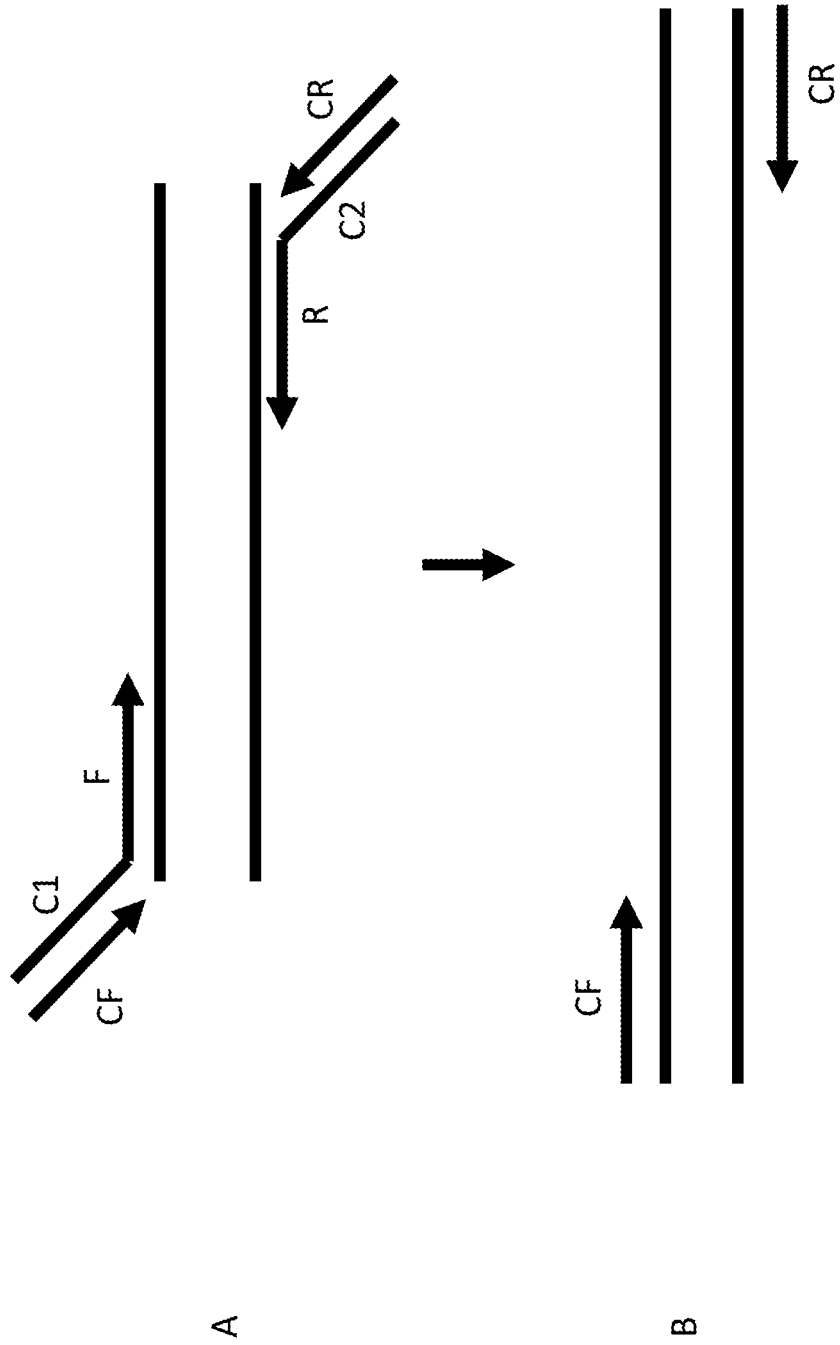
FIGS. 6A, B show a two-step dPCR amplification method using a three nucleotide-type primer underrepresentative primer.

In some applications, detection of the target nucleic acid can be achieved, using a two-step method as shown in FIGS. 6A-B. In one embodiment, the forward three-nucleotide-type primer is linked to the 5' end of a universal artificial 3N sequence (C1), and the other reverse three-nucleotide-type primers is linked to the 5' end of a different universal artificial 3N sequence (C2). Next, a pair of common primers (CF and CR) are provided in the dPCR reaction. The CF primer has the same sequence as C1, and the CR primer has the same sequence as C2. In initial stages of reaction, specific primers C1-F and C2-R hybridize to the template and generate amplicons with C1 and C2 at two ends. In later stages of the reaction, common primers CF and CR participate and dominate the reaction. In some applications of detecting multiple targets in a single reaction solution, the specific primers for each specific target may have the same or different common sequences attached at its 5' end. Multiple targets in a single reaction can be detected by one or more than one set of common primers as described in FIG. 5 by using detection probes associated with common forward primer sequences (CF) or common reverse primer sequences (CR).

e. Analyses

The compositions, methods, and kits can be used to conduct analyses of various genomic alterations associated with a diseased state or other phenotype.

The methods can be used to carry out analyses of chromosomal abnormalities of multiple genes or whole chromosomes for a particular disease. A representative procedure can include comparing either the copy number of a target chromosome (or segment thereof) against that of a reference chromosome or segment thereof or the copy number of a mutant allele relative to a wild-type allele. Such an analyses can be used, for example, in trisomy detection or sex determination.

The methods can be used to carry out analyses of single gene, such as a deletion or point mutation (e.g., single nucleotide change) for a particular disease. A representative procedure for detecting a point mutation or a small deletion in a gene can include comparing the amount of the mutant allele relative to the wild-type allele. A representative procedure for detecting a deletion of a single gene can include comparing either the copy number of a target deleted gene against that of a reference gene.

The methods can be used to carry out SNP-association analyses for a particular disease. A representative procedure can include comparing the dosage of paternally or maternally-inherited single nucleotide polymorphisms (SNPs) to a relative reference haplotype dosage. In some applications, a representative procedure can include preferential allelic imbalance analysis (PAI). PAI occurs when a disease-associated heritable SNP is preferentially retained relative to the wild-type allele. PAI analysis can include comparing the copy number of an allele with a disease-associated heritable SNP to a wild-type allele.

The methods can be used to carry out epigenetic analyses. DNA methylation plays an important role in cancer and neurodegenerative disorders. A representative procedure can include comparing methylation levels from the target region of a diseased sample to a methylation level of the target region from a control sample.

Other analyses that can be used with the present disclosure are described or referenced in Butchbach, M. E. R. *Biomolecular Detection and Quantification* 10: 9-14 (2016).

VI. Computer Implementation

Selection of primer binding sites and primers can be performed by computer-implemented analysis of a target nucleic acid in a computer programmed by non-transitory computer readable storage media. The sequence of a target nucleic acid (one or both strands) is received in a computer. The computer also stores or receives by user input desired nucleotide compositions of primers (e.g., A, T, C). The computer is then programmed to search the target sequence to identify forward and reverse primer binding sites within a distance of one another compatible with amplification that most closely correspond to the primer composition. If the primer composition is A, T, C, then forward and reverse primer binding sites should most closely correspond to A, T and G. The computer can identify forward and reverse primer binding sites on opposite strands or can identify a complement of the forward primer binding sites and reverse primer binding site on the same strand and calculate the forward primer binding site from its complement. The computer can then provide output of candidate pairs of primer binding sites, which may differ to varying degrees with the ideal composition sought. The computer can also show primer designs that hybridize to each of the primer binding site pairs. Multiple primer designs can be shown for the same primer binding site pair with different numbers of units of the underrepresented nucleotide and different numbers of mismatches.

A computer system can include a bus which interconnects major subsystems such as a central processor, a system memory, an input/output controller, an external device such as a printer via a parallel port, a display screen via a display adapter, a serial port, a keyboard, a fixed disk drive, and an internet connection. Many other devices can be connected such as a scanner via I/O controller, a mouse connected to serial port or a network interface. Many other devices or subsystems may be connected in a similar manner. Also, it is not necessary for all of the devices to be present to practice the present invention, as discussed below. The devices and subsystems may be interconnected in different ways. Source code to implement the present invention may be operably disposed in system memory or stored on storage media such as a fixed disk, compact disk or the like. The computer system can be a mainframe, PC, table or cell phone among other possibilities.

VII. Kits

Kits are provided for carrying out the methods and applications described herein.

Kits may often comprise compositions, reagents, devices, and instructions on how to perform the methods or test on a particular biological sample type. Depending on the method desired a kits can comprise one or more of the following components: reagents, primers, reaction mixtures, buffers, enzymes (e.g. endonucleases, exonucleases, ligases, polymerases, RNA polymerases, DNA polymerases, Hot-start polymerases, reverse transcriptases, topoisomerases, kinases, phosphatases), antibodies, primers, probes, dyes, experimental standards (e.g. nucleic acids, DMR-nucleic acids and the like), computer software (e.g. computer-executable logic that instructs a processor) to drive and instruct the devices, and instructions for the user or technical staff such as, researchers or clinicians for implementing the methods provided herein. The DNA polymerase and under-representative primers used in the assay can be stored in a state where they exhibit long-term stability, e.g., in suitable storage buffers or in a lyophilized or freeze dried state. In addition, the kits can further comprise a buffer for the DNA polymerase.

In some embodiments, the kits can further comprise reagents or devices to enable the detection by additional downstream methods that can enhance or add in further clinical detection, prognosis, drug response determination, and diagnosis of a patient suffering from a disease.

In other embodiments, a kit can further comprise a software package for data analysis of genetic profiling, which can include reference genetic profiles for comparison. In some applications the kits software package including connection to a central server to conduct for data analysis and where a report is generated which comprises with recommendation on disease state, drug interactions, or treatment suggestions to a health care provider. In some applications, the report provided with the kit can be a paper or electronic report. It can be generated by computer software provided with the kit, or by a computer sever which the user uploads to a website wherein the computer server generates the report.

In some embodiments, the report may include prognosis such as predicted overall survival, predicted response to therapy, predicted disease-free survival, predicted progression-free survival, or predicted non-reoccurrence survival. The report may include a diagnosis of a condition. The report may include a recommendation for a treatment modality such as treatment or stopping treatment with of a particular drug.

In some embodiments, the kits further include reaction mixtures provided by the disclosure. In some embodiment the kits further including a set of underrepresentative primers for amplifying a particular species-specific gene, wherein the primers for amplifying at least one end of the target sequence include hot-start primers, and optionally non-hot-start primers.

In some embodiments, a kit comprises a underrepresentative primer that is complementary to a first sequence of a target polynucleotide, comprising: (a) a first nucleoside residue at a position corresponding to a target locus residing within the first sequence; (b) a fluorophore coupled to the primer and immediately 5' of the position corresponding to the target locus; and (c) a quencher coupled to the first primer and immediately 3' of the position corresponding to the target locus.

In some embodiments, the kit comprises reagents for selective amplification of a nucleic acid from a sample. The kit comprises (a) a first and/or a second underrepresentative primer, each having '3' end an '5' end, wherein each primer is complementary to a portion of a nucleic acid to be amplified or its complement, and wherein at least one underrepresentative primer comprises (i) a first underrepresentative primer at a position corresponding to a target locus residing within the first sequence; (ii) a fluorophore coupled to the primer an '5' of the position corresponding to the target locus; and (iii) a quencher coupled to the first primer an '3' of the position corresponding to the target locus; (b) an instruction manual for amplifying the nucleic acid. The kit can optionally include a DNA polymerase.

In a further embodiment, the kit comprises reagents for selective amplification of a nucleic acid. The kit comprises (i) an oligonucleotide probe having '3' end and '5' end comprising an RNaseH cleavable domain, (ii) a fluorophore and a quencher, wherein the cleavable domain is positioned between the fluorophore and the quencher, and wherein the probe is complementary to a portion of the target nucleic acid to be amplified or its complement.

Any of the disclosed primers or probes can be incorporated into kits. In some applications the kit includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 primer pairs or probes. Such a kit preferably includes at least one primer pair and preferably at least 5, 20 or 20 primer pairs. The primer pairs in a kit are preferably capable of use in the same multiplex reaction meaning that they have compatible melting temperatures as well as the same underrepresented nucleotide type(s).

a. Applications and Methods

The current disclosure provides compositions, methods, and kits that can be used to detect, diagnose, prognose, monitor, or predict drug response to various diseases, type of infection, and research-related applications.

b. Cancer

Cancer is a disease of genetic aberrations. In the advent of personalized oncological medicine, the clinical management of cancer has move towards tumor genotyping. The present disclosure provides methods for detecting, diagnosing, prognosing, monitoring or predicting drug response in a cancer patient.

Briefly, a representative process starts with obtaining a biological sample from a patient that has or is suspected to have cancer. Next, the nucleic acids of interest are extracted and isolated from the biological sample. Then the isolated nucleic acids are subjected to amplification thereby making PCR amplicons to the target DNA. The PCR amplicons are purified and then diluted and partitioned with the dPCR reaction mixture. After the dPCR reaction is finished, the data is then read and analyzed to identify the status or absolute quantification one or more genetic aberrations such as, mutational status of a specific allele, presence of SNPs, loss of heterozygosity, quantification of copy number variation, quantification of gene expression level, nucleic acid methylation status, or detection of gene rearrangements. Generally, genetic aberrations affecting oncogenes, tumor suppressor genes, DNA amplification, DNA replication, DNA recombination, or other genes known to be correlated with cancer onset, progression, or drug response (e.g., BRCA1 gene, p53 gene, APC gene, Her2/Neu amplification, Bcr/AB1, K-ras gene, and human papillomavirus Types 16 and 18 or other driver or passenger mutations of cancer, as described in Vogelstein, et al., Science. 2013 Mar. 29; 339(6127). In some applications the method can also comprise using the presence or absence of clinical symptoms associated with a particular cancer.

In some embodiments, detection of a mutation in a specific allele, increase in copy number variation, increase gene expression level, hypermethylation status, or detection of a gene rearrangement, or a combination thereof diagnoses the presence of a cancer or grade of cancer. In some embodiments, detection of a lack of a mutation in a specific allele, decrease in copy number variation, decrease gene expression level, hypomethylation status, or detection of no gene rearrangement, or a combination thereof diagnoses the presence of a cancer or grade of cancer.

In some embodiments, one or more mutations in a specific allele, increase in copy number variation, increase gene expression level, hypermethylation status, or detection of gene rearrangements, or a combination thereof diagnoses the absence of cancer. In some embodiments, detection of a lack of a mutation in a specific allele, decrease in copy number variation, decrease gene expression level, hypomethylation status, or detection of no gene rearrangement, or a combination thereof diagnoses the absence of cancer.

In some embodiments, detection of a mutation in a specific allele, increase in copy number variation, increase gene expression level, hypermethylation status, or detection of a gene rearrangement, or a combination thereof predicts a good outcome. In some embodiments, detection of a lack of a mutation in a specific allele, decrease in copy number variation, decrease gene expression level, hypomethylation status, or detection of no gene rearrangement, or a combination thereof predicts a good outcome.

In some embodiments, detection of a mutation in a specific allele, increase in copy number variation, increase gene expression level, hypermethylation status, or detection of a gene rearrangement, or a combination thereof predicts a bad outcome. In some embodiments, detection of a lack of a mutation in a specific allele, decrease in copy number variation, decrease gene expression level, hypomethylation status, or detection of no gene rearrangement, or a combination thereof predicts a bad outcome.

Types of cancers that can be used with the methods include but are not limited to, acute myeloid leukemia, bladder cancer, including upper tract tumors and urothelial carcinoma of the prostate, bone cancer, including chondrosarcoma, Ewing's sarcoma, and osteosarcoma, breast cancer, including noninvasive, invasive, phyllodes tumor, Paget's disease, and breast cancer during pregnancy, central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer; chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcmoma, and extrahepatic cholangiocarcmoma, Hodgkin disease/lymphoma, kidney cancer, melanoma, multiple myeloma, systemic light chain amyloidosis, Waldenstrom's macro globulinemia, myelodysplasia syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sezary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intra-abdominal sarcoma, and desmoid; testicular cancer; thymic malignancies, including thyroid carcinoma, nodule evaluation, papillary carcinoma, follicular carcinoma, Hiirthle cell neoplasm, medullary carcinoma, and anaplastic carcinoma; uterine neoplasms, including endometrial cancer and uterine sarcoma.

c. Autoimmune Disease

Autoimmune diseases are common conditions which appear to develop in genetically susceptible individuals. Genome-wide analyses have resulted in the discovery of more than 300-susceptibility loci for autoimmune disease. See, Gutierrez-Arcelus et al. Nature Reviews Genetics 17, 160-174, February (2016). Furthermore, genome-wide microsatellite screens and large-scale single nucleotide polymorphism (SNP) association studies have identified chromosomal loci that are associated with specific autoimmune diseases including systemic lupus erythematosus, rheumatoid arthritis, juvenile arthritis, multiple sclerosis, and diabetes See, Gutierrez-Roelens et al., Curr Mol Med. 2008 September; 8(6):551-61.

Additional applications of the disclosure provide methods to detect, diagnose, prognose, or monitor an autoimmune disease by determining if a biological sample has one or more of the 300-susceptability or chromosomal loci known to be associated to risk of developing an autoimmune disease.

Briefly, a representative process starts with obtaining a biological sample from a patient that has or is suspected to have cancer. Next, the nucleic acids of interest are extracted and isolated from the biological sample. Then the isolated nucleic acids are subjected to amplification thereby making PCR amplicons to the target DNA. The PCR amplicons are purified and then diluted and partitioned with the dPCR reaction mixture. After the dPCR reaction is finished, the data is the reactions are read and analyzed to identify the presence or absence of one or more susceptibility loci as provided herein. The analysis used will depend on which loci is being investigated. The method can also comprise assessing the presence or absence of clinical symptoms associated with a particular autoimmune disease.

In some embodiments, the determination that the biological sample has one or more susceptibility or chromosomal loci (e.g., set of loci hallmarks, such as, microsatellite, SNPs) relative to wild type indicates an increased risk for developing an autoimmune disease. In some embodiments, the determination that the biological sample does not comprise one or more susceptibility or chromosomal loci relative to wild type indicates an increased risk for developing an autoimmune disease.

In some embodiments, the determination that the biological sample has one or more susceptibility or chromosomal loci (e.g., a set of loci hallmarks, such as, microsatellite, SNPs) relative to wild type indicates a decreased risk for developing an autoimmune disease. In some embodiments, the determination that the biological sample does not comprise one or more susceptibility or chromosomal loci relative to wild type indicates a decreased risk for developing an autoimmune disease.

In some embodiments, the determination that the biological sample has one or more susceptibility or chromosomal loci relative to wild type predicts a good outcome. In some embodiments, the determination that the biological sample does not comprise one or more susceptibility or chromosomal loci relative to wild type predicts a good outcome.

In some embodiments, the determination that the biological sample has one or more susceptibility or chromosomal loci relative to wild type predicts a bad outcome. In some embodiments, the determination that the biological sample does not comprise one or more susceptibility or chromosomal loci relative to wild type predicts a bad outcome.

Moreover, the methods of the disclosure can further include other means of investigating autoimmune diseases as described in, U.S. Pat. Nos. 5,641,864 and 6,617,171.

d. Neurological Disorders

Many neurological disorders are caused by single mutations in genes or chromosomal mutations that affect the normal function of the brain, spinal cord, peripheral nerves or muscles. Many of these types of mutations cause pediatric neurological disorders. Yet, other neurological disorders are complex disorders, caused by several genetic and environmental factors.

Here we provide methods to detect, diagnose, prognose, or monitor a neurological disease caused by chromosomal aberrations and single gene deletions. In short, a representative process starts with obtaining a biological sample from a patient that has or is suspected to have cancer. Next, the nucleic acids of interest are extracted and isolated from the biological sample. Then the isolated nucleic acids are subjected to amplification thereby making PCR amplicons to the target DNA. The PCR amplicons are purified and then diluted and partitioned to come in contact with a dPCR reaction mixture. After the dPCR reaction is finished, the data is then read and positive reactions are counted to determine the presence/absence, mutational status, or absolute quantification of the target DNA comprising the chromosomal aberration associated with the disease. The methods can also comprise using the presence or absence of clinical symptoms associated with a neurological disease.

Examples of neurological disease cause by chromosomal aberrations used with the methods provide herein include but are not limited to, trisomy 13; trisomy 18; and trisomy 21; Pallister-Killian by detection of the presence of a mosaic supernumerary marker isochromosome 12p (iso12p); Chromosome 22q11 Microdeletion Syndrome, by quantify copy number changes within the deleted region; Autosomal Recessive Nonsyndromic Sensorineural hearing loss by quantitatively measuring the deletions within the DFNB1 locus of Chromosome 22q11.

Examples of neurological disease caused by single gene deletions or point mutations used with the methods provide herein include but are not limited to, SMA disorder can be determined by detecting the deletion of a single gene (SMN1 (survival motorneuron 1)); East Asian-type alpha(0)-thalassemia disorder by the detection of the deletion of the gene (HBA1/HBA2 (alpha-globin)); Hypoparathyroidism type-diseases, by determining the mutational status of GCM2 (glial cells missing homolog 2; GCM2(T370M) and GCM2 (R367Tfs*)); Verrucous Venus Malformation type diseases by determining the mutational status of MAP3K3 (mitogen-activated protein kinase 3; MAP3K3(I441M)); Lymphatic malformation and Klippel-Trenaunay syndrome determining the mutational status of PIK3CA (alpha catalytic subunit of phosphatidylinositol-4,5-bisphosphate 3-kinase; PIK3CA (C420R), PIK3CA(E542K), PIK3CA(E545K), PIK3CA (H1047R) and PIK3CA(H1047L)); Trenaunay syndrome by determining the mutational status of SMN1 (SMN1 (Y272C)) with SMA; McCune-Albright syndrome and in GNAS (stimulatory alpha-subunit of G protein, Gs-alpha; GNAS(R201C)). In many cases, the disease-associated intragenic mutations were initially identified using next generation sequencing.

Examples of neurological disorders that can be use with present disclosure include but are not limited to, Adie's syndrome, adrenoleukodystrophy, agenesis of the corpus callosum, agnosia, Aicardi syndrome, Aicardi-Goutieres syndrome disorder, AIDS—neurological complications, akathisia, alcohol related disorders, Alexander disease, Alien hand syndrome (anarchic hand), allochiria, Alpers' disease, altitude sickness, alternating hemiplegia, Alzheimer's disease, amyotrophic lateral sclerosis, anencephaly, aneurysm, Angelman syndrome, angiomatosis, anoxia, Antiphospholipid syndrome, aphasia, apraxia, arachnoid cysts, arachnoiditis, arnold-chiari malformation, Asperger syndrome, arteriovenous malformation, ataxia, ataxias and cerebellar or spinocerebellar degeneration, ataxia telangiectasia, atrial fibrillation, stroke, attention deficit hyperactivity disorder, auditory processing disorder, autism, autonomic dysfunction, back pain, Barth syndrome, Batten disease, becker's myotonia, Behcet's disease, bell's palsy, benign essential blepharospasm, benign focal amyotrophy, benign intracranial hypertension, Bernhardt-Roth syndrome, bilateral frontoparietal polymicrogyria, Binswanger's disease, blepharospasm, Bloch-Sulzberger syndrome, brachial plexus birth injuries, brachial plexus injury, Bradbury-Eggleston syndrome, brain or spinal tumor, brain abscess, brain aneurysm, brain damage, brain injury, brain tumor, Brown-Sequard syndrome, bulbospinal muscular atrophy, CADASIL (cerebral autosomal dominant arteriopathy subcortical infarcts and leukoencephalopathy), Canavan disease, Carpal tunnel syndrome, causalgia, cavernomas, cavernous angioma, cavernous malformation, Central cervical cord Syndrome, Central cord syndrome, Central pain syndrome, central pontine myelinolysis, centronuclear myopathy, cephalic disorder, ceramidase deficiency, cerebellar degeneration, cerebellar hypoplasia, cerebral aneurysm, cerebral arteriosclerosis, cerebral atrophy, cerebral beriberi, cerebral cavernous malformation, cerebral gigantism, cerebral hypoxia, cerebral palsy, cerebral vasculitis, Cerebro-Oculo-Facio-Skeletal syndrome (COFS), cervical spinal stenosis, Charcot-Marie-Tooth disease, chiari malformation, Cholesterol ester storage disease, chorea, choreoacanthocytosis, Chronic fatigue syndrome, chronic inflammatory demyelinating polyneuropathy (CIDP), chronic orthostatic intolerance, chronic pain, Cockayne syndrome type II, Coffin-Lowry syndrome, colpocephaly, coma, Complex regional pain syndrome, compression neuropathy, concussion, congenital facial diplegia, congenital myasthenia, congenital myopathy, congenital vascular cavernous malformations, corticobasal degeneration, cranial arteritis, craniosynostosis, cree encephalitis, Creutzfeldt-Jakob disease, cumulative trauma disorders, Cushing's syndrome, Cytomegalic inclusion body disease (CIBD), cytomegalovirus infection, Dancing eyes-dancing feet syndrome (opsoclonus myoclonus syndrome), Dandy-Walker syndrome (DWS), Dawson disease, decompression sickness, De morsier's syndrome, dejerine-klumpke palsy, Dejerine-Sottas disease, Delayed sleep phase syndrome, dementia, dementia—multi-infarct, dementia—semantic, dementia—subcortical, dementia with lewy bodies, dentate cerebellar ataxia, dentatorubral atrophy, depression, dermatomyositis, developmental dyspraxia, Devic's syndrome, diabetes, diabetic neuropathy, diffuse sclerosis, Dravet syndrome, dysautonomia, dyscalculia, dysgraphia, dyslexia, dysphagia, dyspraxia, dyssynergia cerebellaris myoclonica, dyssynergia cerebellaris progressiva, dystonia, dystonias, Early infantile epileptic, Empty sella syndrome, encephalitis, encephalitis lethargica, encephalocele, encephalopathy, encephalopathy (familial infantile), encephalotrigeminal angiomatosis, encopresis, epilepsy, epileptic hemiplegia, erb's palsy, erb-duchenne and dejerine-klumpke palsies, erythromelalgia, essential tremor, extrapontine myelinolysis, Fabry's disease, Fahr's syndrome, fainting, familial dysautonomia, familial hemangioma, familial idiopathic basal ganglia calcification, familial periodic paralyses, familial spastic paralysis, Farber's disease, febrile seizures, fibromuscular dysplasia, fibromyalgia, Fisher syndrome, floppy infant syndrome, foot drop, Foville's syndrome, Friedreich's ataxia, frontotemporal dementia, Gaucher's disease, generalized gangliosidoses, Gerstmann's syndrome, Gerstmann-Straussler-Scheinker disease, giant axonal neuropathy, giant cell arteritis, Giant cell inclusion disease, globoid cell leukodystrophy, glossopharyngeal neuralgia, Glycogen storage disease, gray matter heterotopia, Guillain-Barre syndrome, Hallervorden-Spatz disease, head injury, headache, hemicrania continua, hemifacial spasm, hemiplegia alterans, hereditary neuropathies, hereditary spastic paraplegia, heredopathia atactica polyneuritiformis, herpes zoster, herpes zoster oticus, Hirayama syndrome, Holmes-Adie syndrome, holoprosencephaly, HTLV-1 associated myelopathy, HIV infection, Hughes syndrome, Huntington's disease, hydranencephaly, hydrocephalus, hydrocephalus—normal pressure, hydromyelia, hypercortisolism, hypersomnia, hypertension, hypertonia, hypotonia, hypoxia, immune-mediated encephalomyelitis, inclusion body myositis, incontinentia pigmenti, infantile hypotonia, infantile neuroaxonal dystrophy, Infantile phytanic acid storage disease, Infantile refsum disease, infantile spasms, inflammatory myopathy, inflammatory myopathies, iniencephaly, intestinal lipodystrophy, intracranial cyst, intracranial hypertension, Isaac's syndrome, Joubert syndrome, Karak syndrome, Kearns-Sayre syndrome, Kennedy disease, Kinsbourne syndrome, Kleine-Levin syndrome, Klippel feil syndrome, Klippel-Trenaunay syndrome (KTS), Kluver-Bucy syndrome, Korsakoff s amnesic syndrome, Krabbe disease, Kugelberg-Welander disease, kuru, Lafora disease, lambert-eaton myasthenic syndrome, Landau-Kleffner syndrome, lateral femoral cutaneous nerve entrapment, Lateral medullary (wallenberg) syndrome, learning disabilities, Leigh's disease, Lennox-Gastaut syndrome, Lesch-Nyhan syndrome, leukodystrophy, Levine-Critchley syndrome, lewy body dementia, Lipid storage diseases, lipoid proteinosis, lissencephaly, Locked-In syndrome, Lou Gehrig's, lumbar disc disease, lumbar spinal stenosis, lupus—neurological sequelae, lyme disease-neurological sequelae, Machado-Joseph disease (spinocerebellar ataxia type 3), macrencephaly, macropsia, megalencephaly, Melkersson-Rosenthal syndrome, Menieres disease, meningitis, meningitis and encephalitis, Menkes disease, meralgia paresthetica, metachromatic leukodystrophy, metabolic disorders, microcephaly, micropsia, migraine, Miller fisher syndrome, mini-stroke (transient ischemic attack), misophonia, mitochondrial myopathy, Mobius syndrome, Moebius syndrome, monomelic amyotrophy, mood disorder, Motor neurone disease, motor skills disorder, Moyamoya disease, mucolipidoses, mucopolysaccharidoses, multi-infarct dementia, multifocal motor neuropathy, multiple sclerosis, multiple system atrophy, multiple system atrophy with orthostatic hypotension, muscular dystrophy, myalgic encephalomyelitis, myasthenia—congenital, myasthenia gravis, myelinoclastic diffuse sclerosis, myoclonic encephalopathy of infants, myoclonus, myopathy, myopathy—congenital, myopathy-thyrotoxic, myotonia, myotonia congenita, myotubular myopathy, narcolepsy, neuroacanthocytosis, neurodegeneration with brain iron accumulation, neurofibromatosis, Neuroleptic malignant syndrome, neurological complications of AIDS, neurological complications of lyme disease, neurological consequences of cytomegalovirus infection, neurological manifestations of AIDS, neurological manifestations of pompe disease, neurological sequelae of lupus, neuromyelitis optica, neuromyotonia, neuronal ceroid lipofuscinosis, neuronal migration disorders, neuropathy-hereditary, neurosarcoidosis, neurosyphilis, neurotoxicity, neurotoxic insult, nevus cavernosus, Niemann-pick disease, Non 24-hour sleep-wake syndrome, nonverbal learning disorder, normal pressure hydrocephalus, O'Sullivan-McLeod syndrome, occipital neuralgia, occult spinal dysraphism sequence, Ohtahara syndrome, olivopontocerebellar atrophy, opsoclonus myoclonus, Opsoclonus myoclonus syndrome, optic neuritis, orthostatic hypotension, Overuse syndrome, chronic pain, palinopsia, panic disorder, pantothenate kinase-associated neurodegeneration, paramyotonia congenita, Paraneoplastic diseases, paresthesia, Parkinson's disease, paroxysmal attacks, paroxysmal choreoathetosis, paroxysmal hemicrania, Parry-Romberg syndrome, Pelizaeus-Merzbacher disease, Pena shokeir II syndrome, perineural cysts, periodic paralyses, peripheral neuropathy, periventricular leukomalacia, persistent vegetative state, pervasive developmental disorders, photic sneeze reflex, Phytanic acid storage disease, Pick's disease, pinched nerve, *Piriformis* syndrome, pituitary tumors, PMG, polio, polymicrogyria, polymyositis, Pompe disease, porencephaly, Post-polio syndrome, postherpetic neuralgia (PHN), postinfectious encephalomyelitis, postural hypotension, Postural orthostatic tachycardia syndrome, Postural tachycardia syndrome, Prader-Willi syndrome, primary dentatum atrophy, primary lateral sclerosis, primary progressive aphasia, Prion diseases, progressive hemifacial atrophy, progressive locomotor ataxia, progressive multifocal leukoencephalopathy, progressive sclerosing poliodystrophy, progressive supranuclear palsy, prosopagnosia, Pseudo-Torch syndrome, Pseudotoxoplasmosis syndrome, pseudotumor cerebri, Rabies, Ramsay hunt syndrome type I, Ramsay hunt syndrome type II, Ramsay hunt syndrome type III, Rasmussen's encephalitis, Reflex neurovascular dystrophy, Reflex sympathetic dystrophy syndrome, Refsum disease, Refsum disease—infantile, repetitive motion disorders, repetitive stress injury, Restless legs syndrome, retrovirus-associated myelopathy, Rett syndrome, Reye's syndrome, rheumatic encephalitis, rhythmic movement disorder, Riley-Day syndrome, Romberg syndrome, sacral nerve root cysts, saint vitus dance, Salivary gland disease, Sandhoff disease, Schilder's disease, schizencephaly, schizophrenia, Seitelberger disease, seizure disorder, semantic dementia, sensory integration dysfunction, septo-optic dysplasia, severe myoclonic epilepsy of infancy (SMEI), Shaken baby syndrome, shingles, Shy-Drager syndrome, Sjogren's syndrome, sleep apnea, sleeping sickness, snatiation, Sotos syndrome, spasticity, spina bifida, spinal cord infarction, spinal cord injury, spinal cord tumors, spinal muscular atrophy, spinocerebellar ataxia, spinocerebellar atrophy, spinocerebellar degeneration, Steele-Richardson-Olszewski syndrome, Stiff-Person syndrome, striatonigral degeneration, stroke, Sturge-Weber syndrome, subacute sclerosing panencephalitis, subcortical arteriosclerotic encephalopathy, SUNCT headache, superficial siderosis, swallowing disorders, Sydenham's chorea, syncope, synesthesia, syphilitic spinal sclerosis, syringohydromyelia, syringomyelia, systemic lupus erythematosus, tabes *dorsalis*, tardive dyskinesia, tardive dysphrenia, tarlov cyst, Tarsal tunnel syndrome, Tay-Sachs disease, temporal arteritis, tetanus, Tethered spinal cord syndrome, Thomsen disease, thomsen's myotonia, Thoracic outlet syndrome, thyrotoxic myopathy, tic douloureux, todd's paralysis, Tourette syndrome, toxic encephalopathy, transient ischemic attack, transmissible spongiform encephalopathies, transverse myelitis, traumatic brain injury, tremor, trigeminal neuralgia, tropical spastic paraparesis, Troyer syndrome, trypanosomiasis, tuberous sclerosis, ubisiosis, uremia, vascular erectile tumor, vasculitis syndromes of the central and peripheral nervous systems, viliuisk encephalomyelitis (VE), Von economo's disease, Von Hippel-Lindau disease (VHL), Von recklinghausen's disease, Wallenberg's syndrome, Werdnig-Hoffman disease, Wernicke-Korsakoff syndrome, West syndrome, Whiplash, Whipple's disease, Williams syndrome, Wilson's disease, Wolman's disease, X-linked spinal and bulbar muscular atrophy, or Zellweger syndrome. Further, the above method can further comprise additional means for investigating neurological conditions as described in U.S. Patent Application Publication No. 20120207726 and 2011018390.

e. Infectious Diseases

Additional applications of the disclosure provide methods to detect infectious diseases caused by bacterial, viral, parasite, and fungal infectious agents.

In some applications, the disclosure can be used to monitor a viral infection of a cell. Viral genomes can evolve quickly and often differ from each other in a few nucleotides or segments, whereas the remaining genome remains unaltered. As a result, primers or probes can be made to recognize the conserved regions and to identify the particular variable nucleotide(s) that are unique to the strain. See for example US patent application US20160259881 which described a dPCR for detecting virus and viral recombination. Examples of viruses used with the disclosure can include but are not limited to, human immunodeficiency virus (HIV), or papilloma virus (HPV), influenza strains such as, H1N1, H5N1, H3N2, H7N9, or H1N2, or a recombinant thereof.

In some applications, the methods can be used to detect or monitor a viral or microbial infection associated with a bioterrorist or biowarfare attack. In some applications, the methods are used to monitor an epidemic or a pandemic in a population or a patient. In some applications, disclosure can be used to detect and diagnosis drug resistance caused by infectious agents. Non-limiting examples of drug-resistance infectious agents that can be used with the disclosure are, vancomycin-resistant *Enterococcus faecium*, methicillin-resistant *Staphylococcus aureus*, penicillin-resistant *Streptococcus pneumonia*, multi-drug resistant *Mycobacterium tuberculosis*, and AZT-resistant human immunodeficiency virus.

Additional applications of the disclosure provide methods to detect or quantify antibiotic resistant strain of a pathogen in a biological sample. In one embodiment, the method can comprise the steps of: (a) performing real-time PCR on nucleic acids from the test sample, wherein the PCR reaction mixture is a reaction mixture described herein; (b) determining the Ct values of the signals generated by the probes that detect a pathogen-specific sequence, whether a gene or intergenic region (herein referred to as a "pathogen-specific gene"), and a polynucleotide sequence that confers antibiotic resistance (herein referred to as an "antibiotic resistance gene"); and (c) comparing the Ct value of the pathogenic-specific gene to the Ct value of the antibiotic resistance gene. In another embodiment, the method can further comprise the steps of (d) amplifying a "bridging region" (a region connecting the usual point of insertion of an element containing an antibiotic resistance gene [the "insertion point"] and a known location in the genome of the target pathogen) and; (e) determining the Ct value of the bridging region.

Additional applications of the disclosure provide methods to detect, diagnose, prognose, or monitor microorganism infections or contaminants in the food or feed industry. For example the disclosure can be used for the identification and characterization of production organisms such as yeast for production of beer, wine, cheese, yogurt, bread, and so forth. In some applications, the disclosure can be used for quality control and certification of products and processes (e.g., livestock, pasteurization, and meat processing) for contaminants. In some applications, the disclosure can be applied to the characterization of plants, bulbs, and seeds for breeding purposes, identification of the presence of plant-specific pathogens, and detection and identification of veterinary infections and in animal breeding programs.

Additional applications of the disclosure provide methods to detect or monitor environmental contaminants. Examples of environmental monitoring methods used with the disclosure include but are not limited to, detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

Additional applications of the disclosure provide methods for forensics or epidemiology studies. Examples of forensic methods used with the disclosure can include but are not limited to, human identification for military personnel and criminal investigation, paternity testing and family relation analysis, HLA compatibility typing, Short Tandem Repeats (STR) and screening blood, sperm, or transplantation organs for contamination. In some applications, the disclosure provides methods and applications for archaeological studies.

Additional applications of the disclosure provide methods to detect or quantify copy number variations. Examples of diseases associated with copy number variations used with the disclosure can include but are not limited to, trisomy 13, trisomy, 21, trisomy 18, Diverge/velocardiofacial syndrome (22ql 1 0.2 deletion), Prader-Willi syndrome (15ql 1-ql3 deletion), Williams-Beuren syndrome (7ql 1.23 deletion), Miller-Dieker syndrome (MDLS) (17 pl3.3 microdeletion), Smith-Magenis syndrome (SMS) (17pl l 0.2 microdeletion), Neurofibromatosis Type 1 (NF1) (17ql 1.2 microdeletion), Phelan-McErmid Syndrome (22ql3 deletion), Rett syndrome (loss-of-function mutations in MECp2 on chromosome Xq28), Merzbacher disease (CNV of PLP1), spinal muscular atrophy (SMA) (homozygous absence of telomerec SMNI on chromosome 5ql3), Potocki-Lupski Syndrome (PTLS, duplication of chromosome 17p.l 1.2). Additional copies of the PMP22 gene can be associated with Charcot-Marie-Tooth neuropathy type IA (CMTI A) and hereditary neuropathy with liability to pressure palsies (HNPP). The methods of detecting CNVs described herein can be used to diagnose CNV disorders described herein and in publications incorporated by reference. Additional diseases that can be used with the disclosure are described in Lupski J. (2007) Nature Genetics 39: S43-S47.

Additional applications of the disclosure provide methods to detect or quantify fetal aneuploidies from a maternal sample (e.g., maternal blood sample, chorionic villus sample, or amniotic fluid). Examples of fetal aneuploidies used with the disclosure can include but are not limited to, trisomy 13, trisomy 18, trisomy 21 (Down Syndrome), Klinefelter Syndrome (XXY), monosomy of one or more chromosomes (X chromosome monosomy, Turner's syndrome), trisomy X, trisomy of one or more chromosomes, tetrasomy or pentasomy of one or more chromosomes (e.g., XXXX, XXYY, XXXY, XYYY, XXXXX, XXXXY, XXXYY, XYYYY and XXYYY), triploidy (three of every chromosome, e.g. 69 chromosomes in humans), tetraploidy (four of every chromosome, e.g. 92 chromosomes in humans), and multiploidy. In some applications, the aneuploidy can be a segmental aneuploidy. Examples of segmental aneuploidies used with the disclosure can include but are not limited to, Ip36 duplication, dup(17)(pl 1.2pl 1.2) syndrome, Down syndrome, Pelizaeus-Merzbacher disease, dup (22)(ql 1.2ql 1.2) syndrome, and cat-eye syndrome.

Additional applications of the disclosure provide methods to detect or quantify an abnormal fetal genotype caused by one or more deletions of sex or autosomal chromosomes. Examples of abnormal fetal genotype caused by one or more deletions which used with the disclosure can include but are not limited to, Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azospermia (factor a), Azospermia (factor b), Azospermia (factor c), or Ip36 deletion. In some cases, a decrease in chromosomal number results in an XO syndrome. In another application, the above method can further comprise other methods for detecting fetal aneuploidy as described in U.S. Pat. No. 8,293,470.

Additional applications of the disclosure provide methods to detect or quantify genomic copy number variations. Examples of excessive genomic DNA copy number variations used with the disclosure can include but are not limited to, Li-Fraumeni cancer predisposition syndrome (Shlien et al. (2008) PNAS 105: 11264-9), CNV is associated with malformation syndromes, including CHARGE (coloboma, heart anomaly, choanal atresia, retardation, genital, and ear anomalies), Peters-Plus, Pitt-Hopkins, or thrombocytopenia-absent radius syndrome (see e.g., Ropers H H (2007) Am J of Hum Genetics 81: 199-207). The relationship between copy number variations and cancer is described, e.g., in Shlien A. and Malkin D. (2009) Genome Med. 1(6): 62. Copy number variations are also associated with, e.g., autism, schizophrenia, and idiopathic learning disability. See e.g., Sebat J., et al. (2007) Science 316: 445-9; Pinto J. et al. (2010) Nature 466: 368-72; Cook E. H. and Scherer S. W. (2008) Nature 455: 919-923. Copy number variations can be associated with resistance of cancer patients to certain therapeutics. For example, amplification of thymidylate synthase can result in resistance to 5-fluorouracil treatment in metastatic colorectal cancer patients. See Wang et al. (2002) PNAS USA vol. 99, pp. 16156-61. Methods of determining CNVs are described, e.g., in PCT Application Publication No. WO2012/109500.

Additional applications of the disclosure provide methods to detect or quantify gene expression level of RNA. (e.g., messenger RNA level). In some applications, the method is used to detect or quantify lower RNA expression levels as compared to a wild-type or standard. In some applications, the method is used to detect or quantify higher RNA expression levels as compared to a wild-type or standard.

Additional applications of the disclosure provide methods to detect and conduct various genetic analyses. Example of genetic analyses used with the disclosure can include but is not limited to, if a sequence is: mutated state or in a wild-type state, has one or more mutations (e.g., a de novo mutation, nonsense mutation, missense mutation, silent mutation, frameshift mutation, insertion, substitution, point mutation, single nucleotide polymorphism (SNP), single nucleotide variant, de novo single nucleotide variant, deletion, rearrangement, amplification, chromosomal translocation, interstitial deletion, chromosomal inversion, loss of heterozygosity, loss of function, gain of function, dominant negative, or lethal). In some applications, the disclosure can be used for the detection of specific point mutations associated with the onset and progression of cancers. In another application, the above method can further comprise additional methods for analyzing nucleic acids, e.g., for detecting mutations, gene expression, or copy number variation, as described in U.S. Patent Application Publication Nos. 20120252015, 2012021549, 20120214163, 20120225428, 20120245235, 20120252753, 20100196898, 20120270739, 20110171646, and U.S. Pat. No. 8,304,194.

Additional applications of the disclosure provide methods to detect or quantify fetal genetic abnormalities that involve quantitative differences between maternal and fetal genetic sequences. Examples of differences in genetic abnormalities between the a mother and her fetus used with the disclosure can include but are not limited to, heterozygous and homozygous between maternal and fetal DNA, and aneuploidies. For example, a missing copy of chromosome X (monosomy X) results in Turner's Syndrome, while an additional copy of chromosome 21 results in Down Syndrome. Other diseases such as Edward's Syndrome and Patau Syndrome are caused by an additional copy of chromosome 18, and chromosome 13, respectively.

Additional applications of the disclosure provide methods to detect or quantify a various chromosomal aneuploidies. Examples of chromosomal aneuploidies used with the disclosure can include but are not limited to, translocation, insertion, amplification, additions, transversion, inversion, aneuploidy, polyploidy, monosomy, trisomy, trisomy 21, trisomy 13, trisomy 14, trisomy 15, trisomy 16, trisomy 18, trisomy 22, triploidy, tetraploidy, and sex chromosome abnormalities including but not limited to XO, XXY, XYY, and XXX. Examples of diseases where the target sequence may exist in one copy in the maternal DNA (heterozygous) but cause disease in a fetus (homozygous), include but are not limited to, sickle cell anemia, cystic fibrosis, hemophilia, and Tay Sachs disease. Accordingly, using the methods described here, one may distinguish genomes with one mutation from genomes with two mutations.

Additional applications of the disclosure provide methods to detect or quantify inherited genetic diseases. Genetic disease can be screened either prenatal or postnatally. Examples of detectable genetic diseases used with the present disclosure can include but are not limited to, 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia. Tay-Sachs Disease, thalassemia, Klinefelter Syndrome, Huntington Disease, autoimmune diseases, lipidosis, obesity defects, hemophilia, inborn errors of metabolism, and diabetes. Additional gene mutations used are described in the following databases: The GDB Human Genome Database, The Official World-Wide Database for the Annotation of the Human Genome Hosted by RTI International, North Carolina USA.

Additional applications of the disclosure provide methods to detect or quantify sickle-cell anemia. Sickle-cell anemia is an autosomal recessive disease. Nine-percent of US blacks are heterozygous, while 0.2% are homozygous recessive. The recessive allele causes a single amino acid substitution in the beta chains of hemoglobin.

Additional applications of the disclosure provide methods to detect or quantify Tay-Sachs Disease. Tay-Sachs Disease is an autosomal recessive resulting in degeneration of the nervous system. Symptoms manifest after birth. Children homozygous recessive for this allele rarely survive past five years of age. Sufferers lack the ability to make the enzyme N-acetyl-hexosaminidase, which breaks down the GM2 ganglioside lipid.

Additional applications of the disclosure provide methods to detect or quantify Phenylketonuria (PKU). PKU is a recessively inherited disorder whose sufferers lack the ability to synthesize an enzyme to convert the amino acid phenylalanine into tyrosine Individuals homozygous recessive for this allele have a buildup of phenylalanine and abnormal breakdown products in the urine and blood.

Additional applications of the disclosure provide methods to detect or quantify Hemophilia. Hemophilia is a group of diseases in which blood does not clot normally. Factors in blood are involved in clotting. Hemophiliacs lacking the normal Factor VIII have Hemophilia A, and those who lack Factor IX have hemophilia B. These genes are carried on the X chromosome, so primers and probes may be used in the present method to detect whether or not a fetus inherited the mother's defective X chromosome, or the father's normal allele.

Additional applications of the disclosure provide methods to detect and quantify genetic abnormalities caused by a differentially methylated regions (DMRs) on a nucleic acid. The term "differentially methylated region" or "DMR" is intended to refer to a region in chromosomic DNA that is differentially methylated between fetal and maternal DNA. The invention provides a new approach for noninvasive prenatal test (NIPT) based on the detection of cffDNA. In some applications DMRs selected for assaying are those that are hypermethylated in fetal DNA and hypomethylated in maternal. That is, these selected DMRs exhibit a greater degree (i.e., more) methylation in fetal DNA as compared to maternal DNA. In other applications, DMRs are those that are hypomethylated in fetal DNA and hypermethylated in maternal blood. In some applications, a large panel (approximately 2000) of DMRs for each of the chromosomes 13, 18, 21, X and Y can be assayed using the methods provided herein. In some applications, the disclosure can be used for detect or quantify a plurality of DMRs on chromosome 21 for diagnosis of trisomy 21.

A plurality of DMRs on chromosome 21 comprise two or more, three or more, four or more, five or more, six or more, seven or more, eight or more, nine or more, ten or more, eleven or more, or twelve regions. In various other embodiments, the plurality of DMRs are on a chromosome selected from the group consisting of chromosome 13, chromosome 18, X chromosome and Y chromosome, to allow for diagnosis of aneuploidies of any of these chromosomes.

A reagent is used to differentially modify methylated as compared to non-methylated DNA. For example, treatment of DNA with bisulfite converts cytosine to uracil, but leaves 5-methylcytosine residues unaffected, and results in a new sequence with A, T, G, and U, which is a perfect template for the primers with limited nucleotide composition. In particular embodiment, at least one of the DMRs is located in RASSF1A and/or TBX3 gene, or selected from the genes: RASSF1A, TBX3, HLCS, ZFY, CDC42EP1, MGC15523, SOX14, GSTP1, DAPS, ESR1, ARC, HSD1784, H1C1, and SPN.

In one aspect, the invention provides NIPT method using a sample of maternal blood. The hypomethylated DNA is chemically altered or enzymatically digested, leaving hypermethylated DNA unaffected. The levels of plurality of DMRs of the targets of interest are determined with primers with limited nucleotide composition. The term "level of the plurality of DMRs" means the amount, prevalence, or copy number of the DMRs. In a fetus with a fetal aneuploidy, as compared to a normal fetus, there is a larger amount of the DMRs as a result of the aneuploidy. The fetal aneuploidy is diagnosed by comparing the level of plurality of DMRs of target of interests to the reference targets of the same sample or the reference targets of a normal maternal reference sample.

Additional applications of the disclosure provide methods for determining the allele identity in a biological sample for the diagnosis of drug metabolism (e.g., pharmacokinetics or pharmacodynamics), drug safety, toxicity or adverse reactions. In some applications the disclosure can be used to for determining the pharmacogenetics of a biological sample from a patient's germline DNA (e.g., SNP). In some applications the disclosure can be used to for determining the pharmacogenomics of a biological sample from a patient's somatic DNA (e.g., tumoral DNA). In some applications, the disclosure can be applied to mutations that are acquired during the course of therapeutic intervention in the treatment of a disease that can decide the course and efficacy of a given treatment. Some non-limiting examples of measuring the efficacy of a drug treatment are detecting or quantifying: minimal residual disease (MRD) in a leukemia patient or sample, a germline SNP(s), or a somatic mutation(s). Examples of pharmacogenetic genes and their variants used with the disclosure can be found in various databases, such as the "Pharmacogenomics Knowledge Base" and are published regularly in the journal *Pharmacogenetics and Genomics*.

Additional applications of the disclosure provide methods to conduct association studies to determine genetic variations underlying disease risk or pharmacogenetics. Genetic association studies test is conducted to find a correlation between disease and a genome region(s) (e.g., locus, haplotype, using statistical methods such quantitative trait loci (QTL)). A higher frequency of a genetic variation in a population of affected with the disease is generally interpreted as being associated with an increase in disease risk. Examples of genetic variations used with the disclosure to conduct an association study can include but are not limited to, SNPs, microsatellite markers, insertion, deletions, variable-number tandem repeats (VNTRs), and copy-number variants (CNVs). In some applications, a case-control association study is conducted. In some applications, a family-based association study or a QTL.

Additional applications of the disclosure provide methods to conduct sequencing library preparation for NGS, single cell amplification, and detection by RNA-seq.

A further method of the disclosure is a combination diagnostic for presence of aneuploidy in a cell. The most common chromosomal aneuploidy is Down syndrome (Trisomy 21), Edwards syndrome (Trisomy 18), and Patau syndrome (Trisomy 13). It is estimated that T21 occurs in 1 out of 691 live births, T18 occurs in 1 out of 3762 live births, and T13 occurs in 1 out of 7906 live births. The rate is higher in the fetuses that do not reach term.

The invasive prenatal diagnostic test such as amniocentesis or chorionic villus sampling are the current gold standard for chromosomal aneuploidy, but are associated with 0.2-0.5% risk of fetal loss. Non-invasive prenatal test (NIPT) such as massively parallel sequencing (MPS) or next generation sequencing (NGS) of libraries generated from cell free DNA (cfDNA) of maternal blood has been shown to be a reliable method of chromosomal aneuploidy detection. However, the NGS assays have to be performed in centralized laboratories, and the current work flow of NGS is very time consuming and expensive. Thus the current NGS NIPT assays are not suitable for large size patient samples or world regions that have no ready access to centralized laboratories.

The invention provides a digital amplification based NIPT for chromosomal aneuploidy of T21, T18, and T13, among other aneuploidies. The test utilizes cfDNA from maternal blood and simultaneously quantifies any or preferably all of chromosomes 21, 18, and 13. The digital amplification can be performed on any regular PCR machine that supports 96 well plate, and the end point reading is performed on a ddPCR reader. Maternal blood is collected during pregnancy. cfDNA is purified from the maternal blood, preferably from plasma. Samples are tested by ddPCR to identify true negatives and positives with an acceptable confidence (e.g., at least 95% confidence). Samples that cannot be classified as true negatives or positives with acceptable confidence (in other words inconclusive samples) are then subjected to sequencing, preferably by a next generation technique.

The disclosure further provides methods for fetal fraction determination and fetal gender determination from a maternal sample that contains fetal material. Examples of fetal specific targets include Y chromosome for a male fetus, and differentially methylated regions (DMR) between fetal and maternal DNA. The presence of Y chromosome indicates a male fetus. The fetal fraction (FF) can be calculated by the following equation, FF=(NY/NYC)/(NY/NYC+NM/NMC)*2*100%, where NY is the copy number of Y specific targets determined by digital amplification, NYC is the number of copies of the Y specific targets present in 1 genome equivalent material, NM is the copy number of total maternal specific targets, and NMC is the number of copies of the maternal specific targets in 1 genome equivalent material. The fetal fraction can be calculated by another equation, FF=(NDMT/NDMC−NDMMT/NDMC)/(NDMUT/NDMC), where NDMT is the copy number of DMRs after methylation specific treatment determined by digital amplification, NDMC is the number of copies of the DMRs in 1 genome equivalent material, NDMMT is the copy number of DMRs in the maternal control sample that does not contain fetal material after methylation specific treatment, NDMUT is the copy number of DMRs without methylation specific treatment. Examples of methylation specific treatment includes but is not limited to methylation sensitive restriction enzyme digestion, and bisulfide treatment.

The disclosure also provides methods to measure a level of released DNA from cells potentially contaminating cfDNA in maternal blood. Maternal blood is collected, stored, transported, and treated before cfDNA is extracted from the plasma. Preservation of the blood and prevention of blood cell from lysis is critical in this process to ensure the quality of cfDNA. Release of blood DNA into the plasma changes the size distribution of extracted cfDNA and reduces fetal fraction, which complicates the downstream applications. The sizes of targeted amplicons fit the size distribution of cfDNA and the sizes of targeted genomic regions exceed 90%, 95%, 99% of the sizes of cfDNA. Multiple targets are quantified simultaneously by dPCR and their amplitudes are adjusted so that positive droplets for each of the targets form a distinct cluster on the 2-dimensional graph and are readily differentiated from multi-target positive droplets. The number of multi-target positive droplets are then calculated theoretically to compare with the observed multi-target positive droplets. The extra amount of multi-target positive droplets indicate the presence of blood cell DNA in the cfDNA extraction and its percentage is calculated by XCMT/CGE*100%, where XCMT is copy number of multi-target regions and CGE is copy number of genome equivalent material in the sample.

The disclosure further provides a method to reduce the fragment sizes for dPCR partitioning. The process of genomic DNA purification results in fragmented DNA with different sizes depending on the methods and operation. Large fragments are more difficult to denature due to their structures and stronger hybridizations. In the dPCR format, accurate quantification rely on successful partitioning of the targets of interest into individual compartment following a Poisson distribution. Therefore multi-target detection or multi-copy gene detection would result in false quantification if two or more targets or two or more copies of the same target are present on the same DNA fragment and are partitioned into 1 compartment. The desired DNA fragment sizes are smaller than 500 bp, 400 bp, 300 bp, 200 bp, 170 bp, 150 bp, or 100 bp. Examples of DNA fragmentation include physical fragmentation methods, such as sonication, acoustic shearing, hydrodynamic shearing, and shearing by electromagnetic force, etc; enzymatic fragmentation methods, such as single or multiple restriction endonuclease digestion, fragmentase treatment, DNaseI treatment, and transposase treatment, etc. In some embodiment, DNA fragmentation is performed before dPCR assembly. In some embodiment, DNA fragmentation and dPCR assembly is combined.

The disclosure further provides methods for target copy number calculation in dPCR when the multiple targets are detected in the same fluorescence channel(s) and are resolved by different signal intensities or different combinations of signal intensities on 1-D amplitude, 2-D amplitude, or 3-D amplitude. The assay is designed so that in each of the fluorescence channels two or more targets are detected. In a given channel, target one (T1) is associated with higher amplitude and the other target (T2) is associated with lower amplitude. When two types of targets are in the same partition, the amplitude of the partition is the same as the higher amplitude. Assume the number of total partitions is T, the number of partitions with higher amplitude is H, and the number of partitions with lower amplitude is L, copy number of T1 is $(\ln(T)-\ln(T-H))*(RV/PV)$, copy number of T2 is $(\ln(T)-\ln(T-H-L))*(RV/PV))-(\ln(T)-\ln(T-H))*(RV/PV)$, where RV is total reaction volume and PV is partition volume. The same principle applies to reactions in other fluorescence channels and to reactions with more than two types of targets.

To carry out the various applications of the methods provide by the present disclosure, various conventional techniques can be used in combination to tailor the methods to the particular application. Such conventional techniques can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, N.Y.; Gait, "Oligonucleotide Synthesis: A Practical Approach" 1984, IRL Press, London, Nelson and Cox (2000), Lehninger, (2004) Principles of Biochemistry $4^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

EXAMPLES

Example 1: Underrepresented Primers Reduce Background Signal in dPCR

This experiment was conducted to determine if primers with an underrepresented nucleotide type (e.g., three nucleotide-type primers) can reduce the background signal in a dPCR reaction as compared to a traditional primer comprising four nucleotides. Primers with an underrepresented nucleotide are sometimes referred to as underrepresented primers.

In the experiment the fluorescence signals generated from a dPCR reaction comprising the underrepresentative primers was compared to a PCR reaction comprising one pair of four nucleotide primers after performing droplet digital PCR reactions (ddPCR) on template containing (n=4) and no template reactions (n=2).

Briefly, a 20 uL ddPCR reaction comprising 1000 copies of E. coli genomic DNA template, 10 uL QX200 EvaGreen® Digital PCR Supermix (2×), and 800 nM of each primer. Both the three nucleotide-type primers and the traditional primers targeted the same genomic region in E. coli. The traditional four nucleotides primers contained two guanines and the three nucleotide-type primer consisted of the ATC nucleotides. Lastly, negative controls comprising no DNA template but otherwise the same 20 uL ddPCR reaction mixture as above were also ran.

Next, water-in-oil droplets were generated with a commercial droplet generator (Bio-Rad Laboratories, Inc.). The cycle for the PCR reaction were as follows: 95° C. for 5 min, followed by 40 cycles of: 95° C. for 15 secs, 60° C. for 30 sec, 4° C. for 5 min, and heated at 95° C. for 5 min. The fluorescence signal was measured and analyzed using a QX200 droplet reader and QuantaSoft™ software (both from Bio-Rad Laboratories, Inc.).

Figure 7:
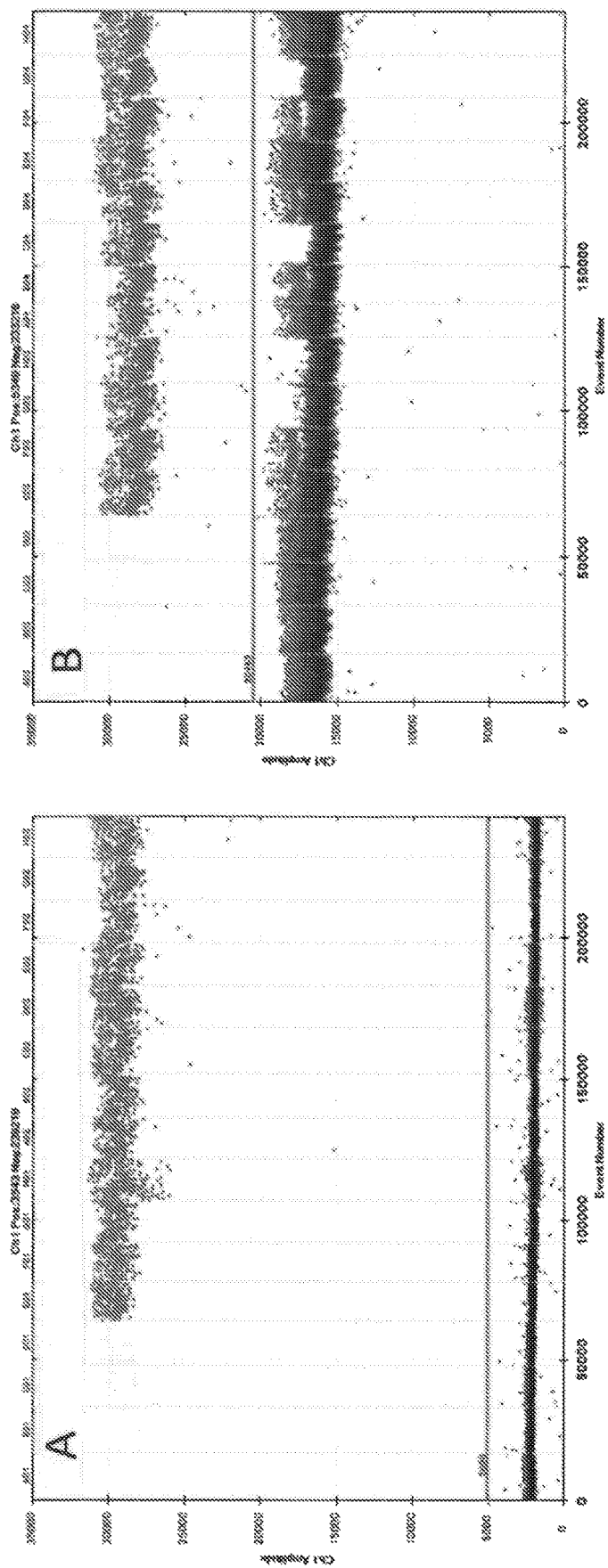
FIGS. 7A, B compares background fluorescence between three nucleotide primers and four nucleotide primers in a digital PCR platform

The results are shown in FIGS. 7A, B. Positive template containing droplets of both three nucleotide-type primer reactions (A) and four nucleotide primer reactions (B) both generated fluorescence signals at 28,000-31,000. While the background signal of three nucleotide-type primer reactions gave extremely low background signal at 2000 compared the (B) four nucleotide primer reactions is at 16,000-18,000.

Taken together, these results indicate that three nucleotide-type primers greatly reduce background signal compared the conventional four nucleotide primers. Additionally, these results suggest that the nucleotide-type primer reduces primer-primer interactions in the reaction.

Example 2: Discrimination of Trisomic and Euploid DNA

This experiment was conducted to determine if underrepresentative primers allows accurate and sensitive multiplexing with dPCR platforms.

In the experiment, a 5-multiplex ddPCR reaction were ran using five pairs of primers in a single reaction tube, to quantify copy number variation of chromosomes (Chr) 21, 18, 13, X, and Y.

A 20 uL ddPCR reaction contained 250 copies of template DNA (either a first or a second DNA template type), 10 uL QX200 EvaGreen® Digital PCR Supermix (2×), a pair of Chr 21 primers, a pair of Chr 18 primers, a pair of Chr13 primers, a pair of Chr X primers, and a pair of Chr Y primers. The PCR conditions were as follows: 95° C. for 5 min, then 40 cycles of: 95° C. for 15 sec, 60° C. for 30 sec, 4° C. for 5 min, and heated at 95° C. for 5 min.

An average of 11%-13.4% of cell-free DNA in maternal blood is of fetal origin. The first DNA template was a euploid sample comprised of normal human genomic DNA. The second DNA template was a trisomic sample comprised of normal human genomic DNA spiked with 10% trisomy 21 genomic DNA from a Down Syndrome patient which typically contains additional full or partial copy of Chr 21.

Thirty-two replicates were performed for each type of template DNA to reach the desired number of positive droplets. The fluorescence signal was measured and analyzed using a QX200 droplet reader and QuantaSoft™ software (both from Bio-Rad Laboratories, Inc.).

Figure 8:
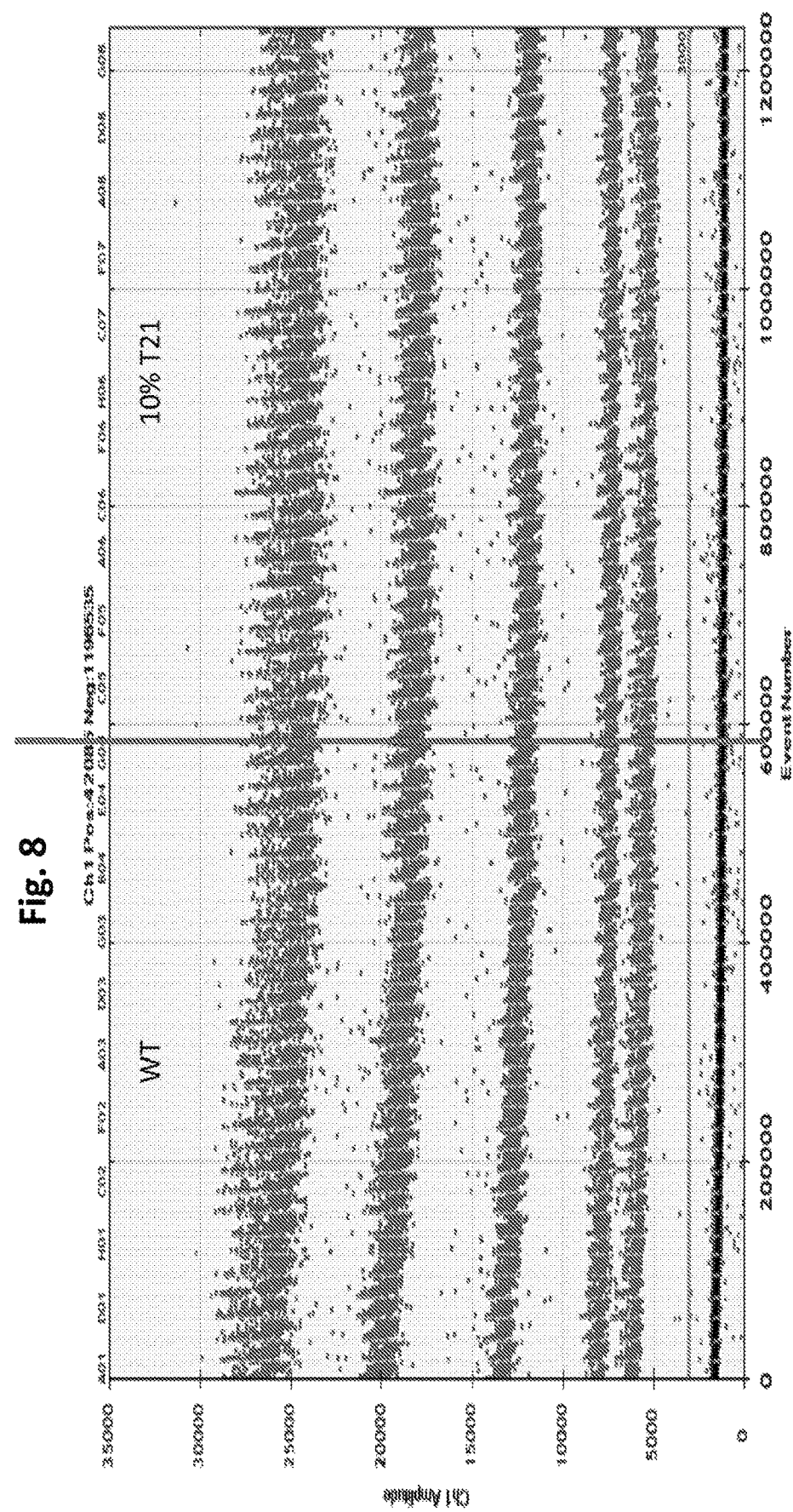
FIG. 8 shows the results from a 5-multiplex dPCR reaction to distinguish between trisomic and euploidy samples.

The results are shown in FIG. 8. The graph shows five species of positive droplets indicating that all five chromosomes 21, 18, 13, X and Y (from top to bottom) are detected and distinguished from the background signal (black dots). Further, the copy numbers of all five chromosomes were also quantified, (see Table 1A below).

TABLE 1A

Copy numbers of each chromosome detected in 5-multiplex dPCR

|  | XY | 13 | 18 | 21 |
| --- | --- | --- | --- | --- |
| WT | 249.15 | 239.61 | 244.11 | 245.32 |
| Ratio | 1.00 | 0.96 | 0.98 | 0.98 |
| 10% T21 | 250.44 | 246.90 | 249.50 | 261.46 |
| Ratio | 1.00 | 0.99 | 1.00 | 1.04 |

The first DNA template was a euploid sample (indicated as WT), comprising a balanced number of chromosomes. In this sample, chromosome 21 was estimated as 245.32 copies, chromosome 18 was estimated as 244.11 copies, chromosome 13 was estimated as 239.61 copies, and chromosome XY was estimated together as one species at 249.15 copies.

In second DNA template was a trisomic sample, comprising 10% additional copy of Chr 21 (indicated as 10% T21). In this sample chromosome 21 was estimated as 261.46 copies, chromosome 18 was estimated as 249.50 copies, chromosome 13 was estimated as 246.90 copies, and chromosome XY was estimated together as one species at 250.44 copies. And the ratios using chromosome XY as a reference are shown in the table.

T-tests were performed between each pair of chromosomes for both DNA template types (WT and 10% T21) to determine if they were significantly different from each other (see Table 1B).

TABLE 1B

Shows the p-value obtained by the -test between each pair of chromosomes for the WT and 10% T21 DNA templates.

| WT | XY | 13 | 18 | 21 |
| --- | --- | --- | --- | --- |
| XY | 1.00 | 0.05 | 0.26 | 0.42 |
| 13 | 0.05 | 1.00 | 0.41 | 0.32 |
| 18 | 0.26 | 0.41 | 1.00 | 0.82 |
| 21 | 0.42 | 0.32 | 0.82 | 1.00 |
| 10% T21 | XY | 13 | 18 | 21 |
| XY | 1.00 | 0.46 | 0.83 | 0.04 |
| 13 | 0.46 | 1.00 | 0.50 | 0.00 |
| 18 | 0.83 | 0.50 | 1.00 | 0.01 |
| 21 | 0.04 | 0.00 | 0.01 | 1.00 |

In the WT DNA templates, no chromosome aneuploidy were found. In the 10% T21 sample, the copy number of Chr 21 was significantly higher while the copy numbers of chromosomes 18, 13, and XY were not significantly different from each another.

These results indicated that using the underrepresentative primers and methods provided by the disclosure can accurately quantify copy number variation in a 5-multiplex reaction to five different chromosomes in a single reaction and obtain statistically significant discrimination between trisomic and euploid samples.

Example 3: Determining Chromosome Aneuploidy in cffDNA Using a 14-Multiplex dPCR In addition to fetal DNA being at low abundance in maternal blood, it is also fragmented as it enters the bloodstream. Therefore more amplicons per target chromosome are needed to detect enough positive droplets in non-invasive prenatal testing (NIPT) applications.

This experiment was conducted to determine if a 14-multiplex dPCR assay using the underrepresentative primers in a single reaction tube can accurately quantify and detect a very low amount of trisomic DNA templates.

A 20 uL ddPCR reaction contained 500 copies of template DNA (comprising either a first, second or third DNA sample), 10 uL QX200 EvaGreen® Digital PCR Supermix (2×), Chr 21 primers, and Chr 18 primers. Because dPCR assay designed with more amplicons per target chromosome requires less amount of cffDNA input seven different amplicons were chosen for chromosome 21 (Chr 18) and seven different amplicons were chosen for chromosome 18 (Chr 18). The PCR conditions were: 95° C. for 5 min, followed by 40 cycles of: 95° C. for 15 sec, 60° C. for 30 sec, 4° C. for 5 min, and heated at 95° C. for 5 min. The fluorescence signal was measured and analyzed using a QX200 droplet reader and QuantaSoft™ software (both from Bio-Rad Laboratories, Inc.).

Eight replicates were performed for each type of genomic DNA to reach the desired number of positive droplets. The first DNA sample was comprised of normal human genomic DNA, the second DNA sample was comprised of normal human genomic DNA spiked with 10% trisomy 21, genomic DNA from a Down Syndrome patient, and the third DNA sample was comprised of normal human genomic DNA spiked with 10% trisomy 18, genomic DNA from a Edwards Syndrome patient.

Figure 9:
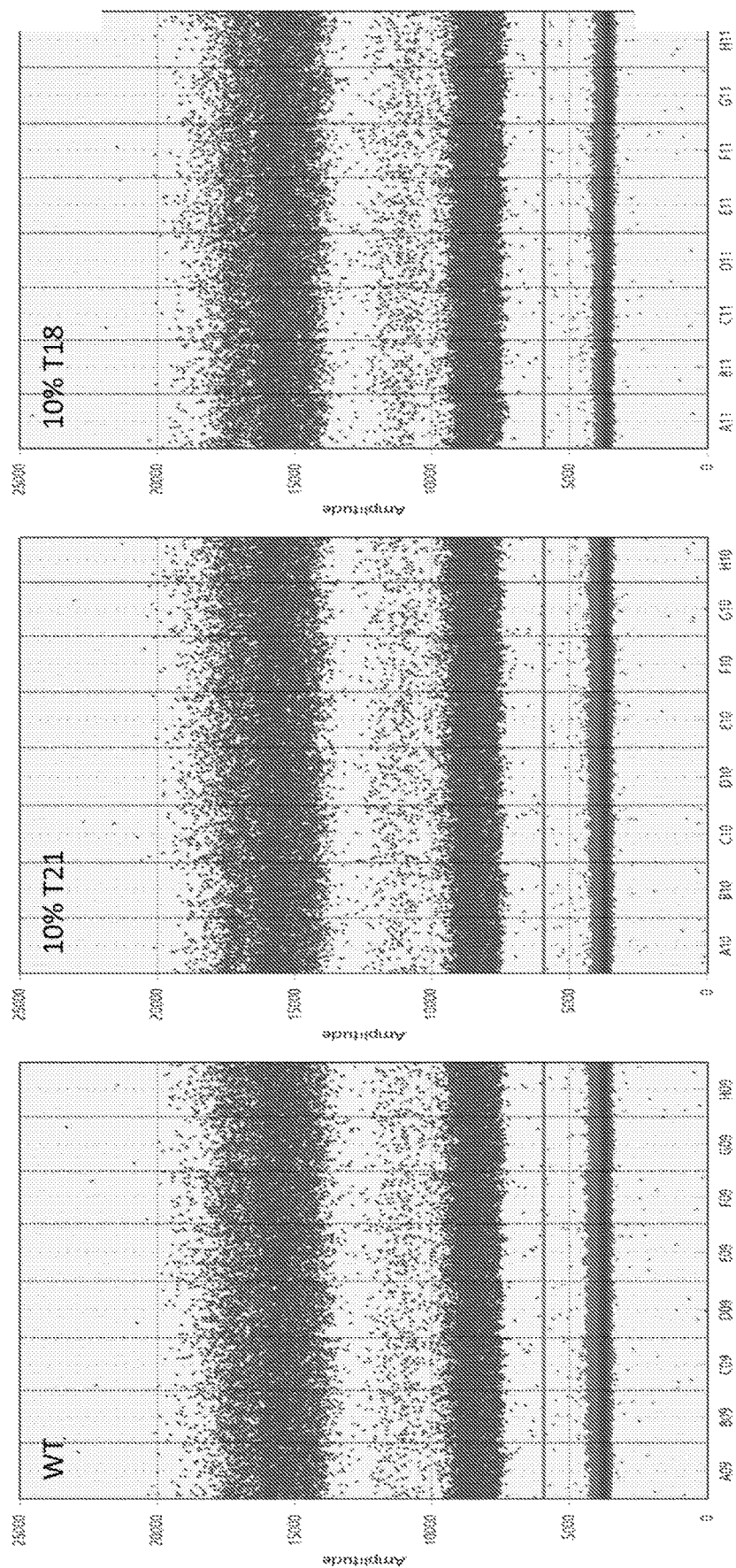
FIG. 9 shows the results from a 14-multiplex dPCR reaction to detect or quantify copy number variations in cffDNA.

FIG. 9 shows the positive droplets detected in each DNA sample type. In FIG. 9 normal human genomic DNA (indicated as WT), normal human genomic DNA spiked with 10% DNA from trisomy 21 (indicated as 10% T21), and normal human genomic DNA spiked with 10% trisomy 18 (indicated as 10% T18). Droplets containing Chr 21 amplicons are located at 14,000-20,000 on the graph; droplets containing Chr 18 amplicons are located at 7,000-12,000 on the graph.

Table 2A shows the copy numbers detected for Chr 21, Chr 18 in each replicate, and the ratio of Chr 21 to Chr 18 for three DNA sample types.

|       | 21     | 18     | 21/18 |              |
|-------|--------|--------|-------|--------------|
| WT    | 3851.5 | 3903.4 | 0.99  | 21 CV 1.66%  |
|       | 3907.7 | 3994.9 | 0.98  | 18 CV 3.30%  |
|       | 3824.5 | 4095.1 | 0.93  | ratio CV 2.42% |
|       | 3854.3 | 3967.9 | 0.97  | Total CV 2.32% |
|       | 3816.9 | 3890.6 | 0.98  |              |
|       | 3904.4 | 4180.8 | 0.93  |              |
|       | 3704.1 | 3795.9 | 0.98  |              |
|       | 3822.2 | 3831.7 | 1.00  |              |
| 10% T21 | 3997.4 | 3873.1 | 1.03 | 21 CV 2.62%  |
|       | 4078.7 | 3829.5 | 1.07  | 18 CV 2.52%  |
|       | 4115.3 | 3791.3 | 1.09  | ratio CV 3.06% |
|       | 4125.5 | 3982.2 | 1.04  | Total CV 2.07% |
|       | 3930.3 | 3975.9 | 0.99  |              |
|       | 4039.2 | 4034.9 | 1.00  |              |
|       | 4265.0 | 4053.2 | 1.05  |              |
|       | 4195.1 | 4015.1 | 1.04  |              |
| 10% T18 | 4089.1 | 4270.5 | 0.96 | 21 CV 3.14%  |
|       | 4109.7 | 4532.9 | 0.91  | 18 CV 4.49%  |
|       | 4137.9 | 4555.2 | 0.91  | ratio CV 2.61% |
|       | 4271.1 | 4472.5 | 0.95  | Total CV 3.67% |
|       | 4057.0 | 4452.8 | 0.91  |              |
|       | 4003.0 | 4168.4 | 0.96  |              |
|       | 3878.0 | 4123.8 | 0.94  |              |
|       | 3906.4 | 4074.7 | 0.96  |              |

Table 2B, shows the mean copy numbers for the three DNA sample types and p-values obtained from the t-test.

|         | 21     | 18     | 21/18 | TTest |
|---------|--------|--------|-------|-------|
| WT      | 3835.7 | 3957.6 | 0.97  |       |
| 10% T21 | 4093.3 | 3944.4 | 1.04  | 0.00  |
| 10% T18 | 4056.5 | 4331.4 | 0.94  | 0.02  |

The p-values obtained from the t-test indicate that the multiplex assay was able to detect statistically significant differences in copy number variation between trisomy T21 and T18 samples and the normal, euploid samples.

These results show that underrepresentative primers and methods provided by the disclosure can detect chromosomal abnormalities with the sensitivity of detection as low as 10% DNA concentration difference in a sample using a 14-multiplex dPCR assay. Additionally, this experiment shows that underrepresentative primers and can be used with dPCR platforms to detect or quantify trisomy of Chr 21 and Chr 18 in a low abundant cffDNA, as required for non-invasive prenatal testing (NIPT) methods.

Example 4: Determination of Down Syndrome, Edwards Syndrome, and Patau Syndrome in cffDNA Using a 15-Multiplexing dPCR In this experiment, 15-multiplexing dPCR was conducted in a single reaction tube using five different amplicons were chosen for chromosome 21, each with the same FAM fluorophore labeled probe, five different amplicons were chosen for chromosome 18 each detected with the same FAM fluorophore labeled probe, and 5 amplicons were chosen for chromosome 13 each detected with the same HEX fluorophore labeled probe.

Four types of DNA samples were tested, normal human genomic DNA, normal human genomic DNA spiked with 10% trisomy 21 genomic DNA, from a Down Syndrome patient, normal human genomic DNA spiked with 10% trisomy 18 genomic DNA, from a Edwards Syndrome patient, and normal human genomic DNA spiked with 10% trisomy 13 genomic DNA from a Patau Syndrome patient.

A 20 uL ddPCR reaction contained 500 copies of template DNA, 10 uL QX200 Probe Digital PCR Supermix (2×), Chr 21 primers, Chr18 primers, Chr 13 primers, probe 1, probe 2, and probe 3. The PCR conditions were, 95° C. for 5 min, followed by 50 cycles of: 95° C. for 15 sec, 60° C. for 45 sec, 98° C. for 10 min, and incubated at 4° C. for 5 min. Eight replicates were performed for each DNA sample type to reach the desired number of positive droplets. The fluorescence signal was measured and analyzed using a QX200 droplet reader and QuantaSoft software (both from Bio-Rad Laboratories, Inc.).

Figure 10:
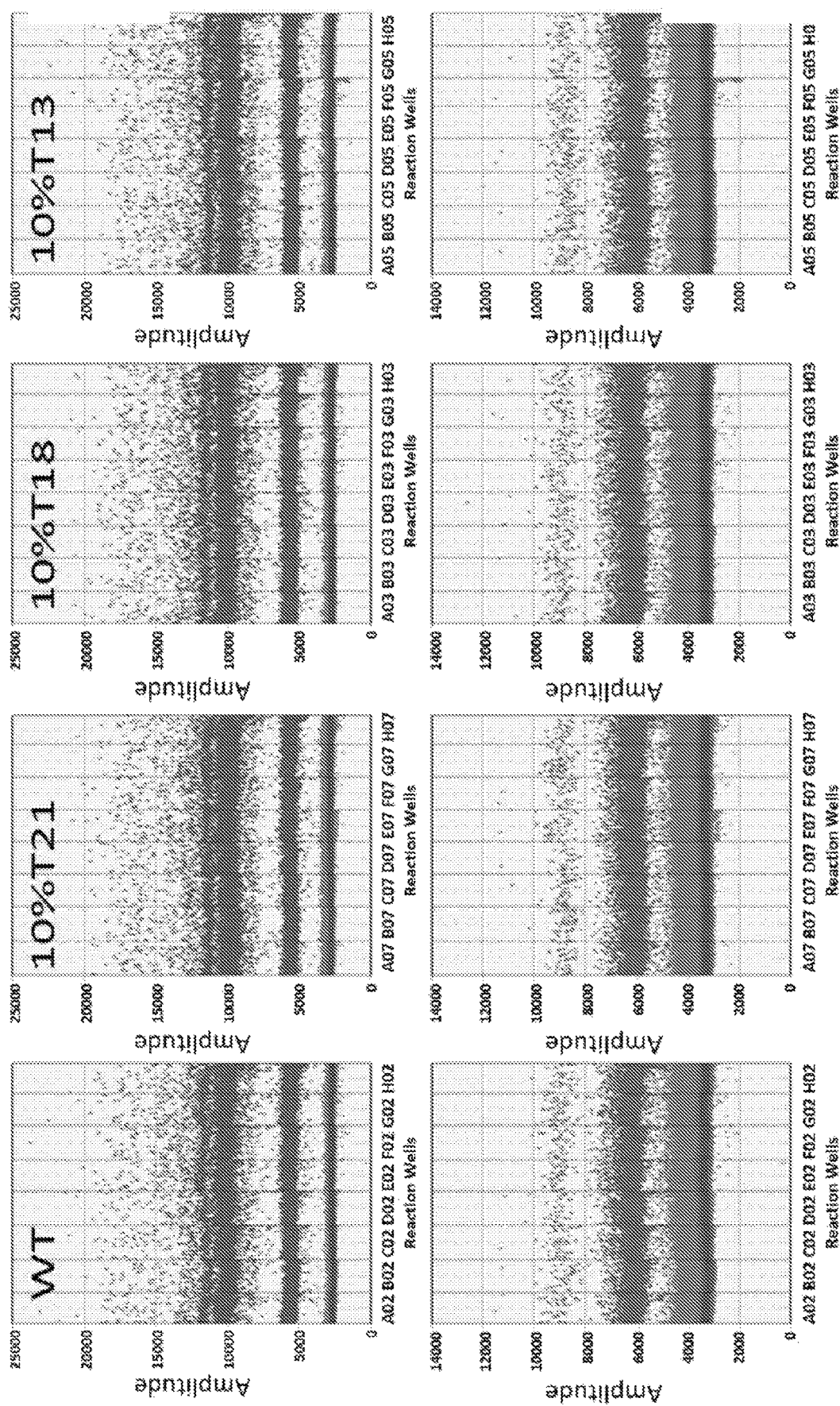
FIG. 10 shows results from a 15-multiplex dPCR assay to detect or quantify copy number variations in cffDNA.

FIG. 10 shows the positive amplicon droplets for each DNA sample type. Positive droplets containing Chr 21 amplicons are at located cluster (A), droplets containing Chr 18 amplicons are located at cluster (B) and droplets containing Chr 13 amplicons located at cluster (C).

Tables 3A, 3B, and 3C show copy number quantified for Chr 21, 13, and 18, respectively, and the ratios for each replicate for the four DNA sample types (WT, 10% T21, 10% T18, and 10% T13). At the bottom of Tables 3A, 3B, and 3C the mean copy number and p-value obtained from the t-tests between the WT (normal) and T21, T18, and T13 trisomic samples is shown.

TABLE 3A

Quantification of Copy Number for Chromosome 21

| 500WT | | | | 500-10% T21 | | | |
|---|---|---|---|---|---|---|---|
| 21 + 18 | 21 | 18 | 13 | 21 + 18 | 21 | 18 | 13 |
| 3886.13 | 1947.13 | 1938.99 | 1919.03 | 3946.81 | 2002.70 | 1944.11 | 1944.06 |
| 3916.62 | 1943.51 | 1973.12 | 2014.30 | 3776.63 | 1919.72 | 1856.91 | 1708.56 |
| 3784.30 | 1883.06 | 1901.23 | 2014.90 | 3934.02 | 2005.60 | 1928.42 | 2015.58 |
| 3880.90 | 2014.60 | 1866.30 | 2079.43 | 3935.26 | 2084.82 | 1850.44 | 1947.06 |
| 3874.87 | 1963.88 | 1910.99 | 1978.89 | 4061.44 | 2131.48 | 1929.96 | 2027.19 |
| 3880.69 | 1925.12 | 1955.58 | 1972.96 | 4076.68 | 2121.37 | 1955.32 | 2055.14 |

TABLE 3A-continued

Quantification of Copy Number for Chromosome 21

| 3885.15 | 1886.78 | 1998.37 | 1977.26 | 3938.14 | 2020.44 | 1917.70 | 1899.01 |
|---|---|---|---|---|---|---|---|
| 3798.14 | 1846.55 | 1951.59 | 1934.42 | 3900.51 | 1983.86 | 1916.64 | 1921.92 |
| Mean | 481.58 | 484.26 | 496.60 | Mean | 508.44 | 478.11 | 484.95 |

| Ratio | 21/18 | 21/13 | 18/13 | Ratio | 21/18 | 21/13 | 18/13 |
|---|---|---|---|---|---|---|---|
| 1 | 1.00 | 1.01 | 1.01 | 1 | 1.03 | 1.03 | 1.00 |
| 2 | 0.98 | 0.96 | 0.98 | 2 | 1.03 | 1.12 | 1.09 |
| 3 | 0.99 | 0.93 | 0.94 | 3 | 1.04 | 1.00 | 0.96 |
| 4 | 1.08 | 0.97 | 0.90 | 4 | 1.13 | 1.07 | 0.95 |
| 5 | 1.03 | 0.99 | 0.97 | 5 | 1.10 | 1.05 | 0.95 |
| 6 | 0.98 | 0.98 | 0.99 | 6 | 1.08 | 1.03 | 0.95 |
| 7 | 0.94 | 0.95 | 1.01 | 7 | 1.05 | 1.06 | 1.01 |
| 8 | 0.95 | 0.95 | 1.01 | 8 | 1.04 | 1.03 | 1.00 |
| Mean | 1.00 | 0.97 | 0.98 | Mean | 1.06 | 1.05 | 0.99 |
|  |  |  |  | TTest | 0.00 | 0.00 | 0.59 |

TABLE 3B

Quantification of Copy Number for Chromosome 13

| 500WT | | | | 500-10% T13 | | | |
|---|---|---|---|---|---|---|---|
| 21 + 18 | 21 | 18 | 13 | 21 + 18 | 21 | 18 | 13 |
| 3808.92 | 1925.70 | 1883.23 | 1960.65 | 3797.54 | 1928.23 | 1869.31 | 2035.39 |
| 3695.42 | 1764.97 | 1930.45 | 1960.80 | 3798.13 | 1824.59 | 1973.54 | 2101.79 |
| 3791.28 | 1882.92 | 1908.36 | 1979.30 | 3703.71 | 1822.78 | 1880.93 | 2161.46 |
| 3764.12 | 1885.58 | 1878.54 | 2001.61 | 3783.33 | 1846.10 | 1937.23 | 2143.86 |
| 3863.60 | 1854.14 | 2009.46 | 2001.80 | 3856.88 | 1930.98 | 1925.89 | 2147.23 |
| 3739.17 | 1860.01 | 1879.16 | 2002.80 | 3832.75 | 1946.50 | 1886.25 | 2064.22 |
| 3872.64 | 1892.81 | 1979.83 | 2164.76 | 3974.42 | 1897.64 | 2076.79 | 2104.37 |
| 3730.44 | 1906.16 | 1824.27 | 1951.59 | 3793.16 | 1942.02 | 1851.14 | 2187.52 |
| Mean | 467.88 | 477.92 | 500.73 | Mean | 473.09 | 481.28 | 529.56 |

| Ratio | 21/18 | 21/13 | 18/13 | Ratio | 21/18 | 21/13 | 18/13 |
|---|---|---|---|---|---|---|---|
| 1 | 1.02 | 0.98 | 0.96 | 1 | 1.03 | 0.95 | 0.92 |
| 2 | 0.91 | 0.90 | 0.98 | 2 | 0.92 | 0.87 | 0.94 |
| 3 | 0.99 | 0.95 | 0.96 | 3 | 0.97 | 0.84 | 0.87 |
| 4 | 1.00 | 0.94 | 0.94 | 4 | 0.95 | 0.86 | 0.90 |
| 5 | 0.92 | 0.93 | 1.00 | 5 | 1.00 | 0.90 | 0.90 |
| 6 | 0.99 | 0.93 | 0.94 | 6 | 1.03 | 0.94 | 0.91 |
| 7 | 0.96 | 0.87 | 0.91 | 7 | 0.91 | 0.90 | 0.99 |
| 8 | 1.04 | 0.98 | 0.93 | 8 | 1.05 | 0.89 | 0.85 |
| Mean | 0.98 | 0.94 | 0.95 | Mean | 0.98 | 0.89 | 0.91 |
|  |  |  |  | TTest | 0.86 | 0.04 | 0.03 |

TABLE 3C

Quantification of Copy Number for Chromosome 18

| 500WT | | | | 500-10% T18 | | | |
|---|---|---|---|---|---|---|---|
| 21 + 18 | 21 | 18 | 13 | 21 + 18 | 21 | 18 | 13 |
| 3808.92 | 1925.70 | 1883.23 | 1960.65 | 4144.68 | 1917.74 | 2226.94 | 2184.66 |
| 3695.42 | 1764.97 | 1930.45 | 1960.80 | 4031.93 | 1941.23 | 2090.70 | 2023.47 |
| 3791.28 | 1882.92 | 1908.36 | 1979.30 | 3965.90 | 1905.40 | 2060.50 | 2113.21 |
| 3764.12 | 1885.58 | 1878.54 | 2001.61 | 4084.25 | 1919.66 | 2164.59 | 2108.15 |
| 3863.60 | 1854.14 | 2009.46 | 2001.80 | 4187.42 | 1999.15 | 2188.27 | 2135.89 |
| 3739.17 | 1860.01 | 1879.16 | 2002.80 | 4219.04 | 2042.31 | 2176.73 | 2155.85 |
| 3872.64 | 1892.81 | 1979.83 | 2164.76 | 4127.07 | 1954.72 | 2172.35 | 2098.22 |
| 3730.44 | 1906.16 | 1824.27 | 1951.59 | 4146.76 | 2004.90 | 2141.86 | 2036.32 |
| Mean | 467.88 | 477.92 | 500.73 | Mean | 490.16 | 538.19 | 526.74 |

| Ratio | 21/18 | 21/13 | 18/13 | Ratio | 21/18 | 21/13 | 18/13 |
|---|---|---|---|---|---|---|---|
| 1 | 1.02 | 0.98 | 0.96 | 1 | 0.86 | 0.88 | 1.02 |
| 2 | 0.91 | 0.90 | 0.98 | 2 | 0.93 | 0.96 | 1.03 |
| 3 | 0.99 | 0.95 | 0.96 | 3 | 0.92 | 0.90 | 0.98 |
| 4 | 1.00 | 0.94 | 0.94 | 4 | 0.89 | 0.91 | 1.03 |
| 5 | 0.92 | 0.93 | 1.00 | 5 | 0.91 | 0.94 | 1.02 |

TABLE 3C-continued

Quantification of Copy Number for Chromosome 18

| 6 | 0.99 | 0.93 | 0.94 | 6 | 0.94 | 0.95 | 1.01 |
|---|------|------|------|---|------|------|------|
| 7 | 0.96 | 0.87 | 0.91 | 7 | 0.90 | 0.93 | 1.04 |
| 8 | 1.04 | 0.98 | 0.93 | 8 | 0.94 | 0.98 | 1.05 |
| Mean | 0.98 | 0.94 | 0.95 | Mean | 0.91 | 0.93 | 1.02 |
|  |  |  |  | TTest | 0.00 | 0.82 | 0.00 |

All of the t-tests performed had significant p-values as shown in Tables 3A, #B and 3C. These results indicate the 15-multiplex dPCR assay using the underrepresentative primers in a single reaction can detect chromosomal aneuploidy in Ch 21, Ch 13, and Chr 18 in a small amount of cffDNA.

Example 5: Determining Copy Number Variation Based on Conversion of Methylated Cytosine The conversion of methylated cytosine was performed on commercially available genomic DNA purified from *E. coli* (ATCC 700927D-5), with the EZ DNA Methylation™ Kit by ZYMO RESEARCH following manufacturer's instruction. 200 ng *E. coli* genomic DNA was converted in the experiment and purified afterwards. We next mixed converted DNA with original DNA (mimicking the methylated DNA) at ratios ranging from 1:100 (converted:original) to 100:1 (converted:original).

Two ddPCR reactions were performed on each of the different mixtures, one targeting the converted DNA sequence and the other one targeting the original DNA sequence. A 20 uL ddPCR reaction contained 500 copies of template DNA, 10 uL QX200 Evagreen® Digital PCR Supermix (2×), and the primer mix. The PCR conditions were, 95° C. for 5 min, followed by 40 cycles of: 95° C. for 15 sec, 60° C. for 30 sec, 4° C. for 5 min, 90° C. for 10 min, and incubated at 4° C. for 5 min. Eight replicates were performed for each DNA sample type to reach the desired number of positive droplets. The fluorescence signal was measured and analyzed using a QX200 droplet reader and QuantaSoft™ software (both from Bio-Rad Laboratories, Inc.).

This example demonstrates that majority of cytosines in the DNA were converted to uracils, and primers that target converted DNA or original DNA successfully quantified the corresponding targets.

Although the invention has been described in detail for purposes of clarity of understanding, certain modifications may be practiced within the scope of the appended claims. All publications including accession numbers, websites and the like, and patent documents cited in this application are hereby incorporated by reference in their entirety for all purposes to the same extent as if each were so individually denoted. To the extent difference version of a sequence, website or other reference may be present at different times, the version associated with the reference at the effective filing date is meant. The effective filing date means the earliest priority date at which the accession number at issue is disclosed. Unless otherwise apparent from the context any element, embodiment, step, feature or aspect of the invention can be performed in combination with any other.

SEQUENCE LISTING

The sequence listing provides sequences of nucleic acids used in the Examples.

| SEQ ID NO: |  |  |  |
|---|---|---|---|
| 1. | Ecoli-3N-F1 | TTTAATACCTCAATCTCTATCACAATATCCACATTC | Example 1 |
| 2. | Ecoli-3N-R1 | AACAACAATATCTACTCAATCTCCACACTCCCCTAC | Example 1 |
| 3. | Ecoli-4N-F1 | TTTAATACCTCAATGTGTATCACAATATCCACATTC | Example 1 |
| 4. | Ecoli-4N-R1 | AACAAGAATATCTACTCAATCTCCAGACTCCCCTAC | Example 1 |
| 5. | Chr21-F1 | CCCACACTCTTCTTCAAGGTTCACCTTCC | Example 2 |
| 6. | Chr21-R1 | GACCTTCATCACCTTTTGTTTCATCTC | Example 2 |
| 7. | Chr18-F1 | CCTACTTCTGTCAATTCATCAGACTCATTCTCCATCC | Example 2 |
| 8. | Chr18-R1 | AACATCTCTTCCCCAAAGGATCACAACTCCTC | Example 2 |
| 9. | Chr13-F1 | CTCTTGCCTACACCTGCATTTACCCCAAC | Example 2 |
| 10. | Chr13-R1 | TCCACAGCTCCTGCTTATATCAAAACC | Example 2 |
| 11. | ChrX-F1 | CATACCTCCTTGTCTTGAACCCCAAACCTTCC | Example 2 |
| 12. | ChrX-R1 | AATCTTCTACCGATGCCTTTCTTATTTCCCC | Example 2 |
| 13. | ChrY-F1 | CATACCTCCTTGTCTTGAACCCCAAACCTTCC | Example 2 |
| 14. | ChrY-R1 | AATCTTCTACCGATGCCTTTCTTATTTCCCC | Example 2 |

| | | | |
|---|---|---|---|
| 15. | Chr21-F2 | CCCACACTCTTCTTCAAGGTTCACCTTCC | Example 3 |
| 16. | Chr21-R2 | GACCTTCATCACCTTTTGTTTCATCTC | Example 3 |
| 17. | Chr21-F3 | CTCTCAAAGTTTTCTGCCTCAAATTCC | Example 3 |
| 18. | Chr21-R3 | TTTCGAAACCCCTCATTCCACGAAAAATACCC | Example 3 |
| 19. | Chr21-F4 | TGTCCCCCTAAAATTCATATGCCAATCTTAACCTCC | Example 3 |
| 20. | Chr21-R4 | TCTCCACCCCATGACCTAATCACCTCCCAAAGTTCCCCACCTTC | Example 3 |
| 21. | Chr21-F5 | AACCCTTATAACCAGAGATCTTTCTCC | Example 3 |
| 22. | Chr21-R5 | TCAAGTCCCTCTCATGCTTCTAATCAC | Example 3 |
| 23. | Chr21-F6 | AACACTCCCATGATTCAGTTATCTCCCAC | Example 3 |
| 24. | Chr21-R6 | TCCTCACCCAAATCTCCTATTGTAGCTTCCATAATTCCCAC | Example 3 |
| 25. | Chr21-F7 | TGTCCTAACCCAAATCCCATCTTGAATTTTAATCCCC | Example 3 |
| 26. | Chr21-R7 | GAAACTACTCCCATGATTCAATTACCTCCTACC | Example 3 |
| 27. | Chr18-F2 | TTTGAAAGTATTCCCTCCTCCTC | Example 3 |
| 28. | Chr18-R2 | CTTCCCTGCTGAATTCTATCAAAC | Example 3 |
| 29. | Chr18-F3 | TTGTCCTTTCCCAGTTATTTCCCTCAAC | Example 3 |
| 30. | Chr18-R3 | CACTTTGCTTCCAATCATTGATTCCACCC | Example 3 |
| 31. | Chr18-F4 | CCCCCCCCCAAAAAAAGGAAATACAAATC | Example 3 |
| 32. | Chr18-R4 | TCTTTAGCTAAATCAGCTCACTACCC | Example 3 |
| 33. | Chr18-F5 | CAAAGCCTTCTCTCGCACATTCTTTC | Example 3 |
| 34. | Chr18-R5 | AACCACGTCCTTTCCTCCGTCATCCCTACACCAAC | Example 3 |
| 35. | Chr18-F6 | CCCCCACTCAAATCTCATCTTGTAGCTCCCATAATCCCC | Example 3 |
| 36. | Chr18-R6 | ACTTGTCCCCATGATTCAATTATCTCCCACC | Example 3 |
| 37. | Chr18-F7 | TTCTAAAACTCTTTGCTGCACCCCCATTTAAC | Example 3 |
| 38. | Chr18-R7 | AATTTCAGCCTAAATTTCCCGACACCTTCATTTTCTCCC | Example 3 |
| 39. | cChr21-F1 | TCCTATCCGGCCTTCCATATCACCCCTCCCCACACTCTTCTTCAAGGTTCACCTTCC | Example 4 |
| 40. | cChr21-R1 | GACCTTCATCACCTTTTGTTTCATCTC | Example 4 |
| 41. | cChr21-F2 | TCCTATCCGGCCTTCCATATCACCCCTCCCCACACTCTTCTTCAAGGTTCACCTTCC | Example 4 |
| 42. | cChr21-R2 | GACCTTCATCACCTTTTGTTTCATCTC | Example 4 |
| 43. | cChr21-F3 | TCCTATCCGGCCTTCCATATCACCCCTCCTCTCAAAGTTTTCTGCCTCAAATTCC | Example 4 |
| 44. | cChr21-R3 | TTTCGAAACCCCTCATTCCACGAAAAATACCC | Example 4 |
| 45. | cChr21-F4 | TCCTATCCGGCCTTCCATATCACCCCTCTGTCCCCCTAAAATTCATATGCCAATCTTAACCTCC | Example 4 |
| 46. | cChr21-R4 | TCTCCACCCCATGACCTAATCACCTCCCAAAGTTCCCCACCTTC | Example 4 |
| 47. | cChr21-F5 | TCCTATCCGGCCTTCCATATCACCCCTCAACCCTTATAACCAGAGATCTTTCTCC | Example 4 |
| 48. | cChr21-R5 | TCAAGTCCCTCTCATGCTTCTAATCAC | Example 4 |
| 49. | cChr18-F1 | ACCACTCTTCCTCAGAAGATATCCTTCCCCTACTTCTGTCAATTCATCAGACTCATTCTCCATCC | Example 4 |
| 50. | cChr18-R1 | AACATCTCTTCCCCAAAGGATCACAACTCCTC | Example 4 |
| 51. | cChr18-E2 | ACCACTCTTCCTCAGAAGATATCCTTCCTTTGAAAGTATTCCCTCCTCCTC | Example 4 |
| 52. | cChr18-R2 | CTTCCCTGCTGAATTCTATCAAAC | Example 4 |
| 53. | cChr18-E3 | ACCACTCTTCCTCAGAAGATATCCTTCCTTGTCCTTTCCCAGTTATTTCCCTCAAC | Example 4 |

| | | | |
|---|---|---|---|
| 54. | cChr18-R3 | CACTTTGCTTCCAATCATTGATTCCACCC | Example 4 |
| 55. | cChr18-E4 | ACCACTCTTCCTCAGAAGATATCCTTCCCCCCCCCCCAAAAAAAGGAAATACAAATC | Example 4 |
| 56. | cChr18-R4 | TCTTTAGCTAAATCAGCTCACTACCC | Example 4 |
| 57. | cChr18-F5 | ACCACTCTTCCTCAGAAGATATCCTTCCCAAAGCCTTCTCTCGCACATTCTTTC | Example 4 |
| 58. | cChr18-R5 | AACCACGTCCTTTCCTCCGTCATCCCTACACCAAC | Example 4 |
| 59. | cChr13-F1 | AACCCCGTACAAAATCGCCACCACCAACCTCTTGCCTACACCTGCATTTACCCCAAC | Example 4 |
| 60. | cChr13-R1 | TCCACAGCTCCTGCTTATATCAAAACC | Example 4 |
| 61. | cChr13-E2 | AACCCCGTACAAAATCGCCACCACCAACTAAAACACATTCAACACTGTCTCCCAGACACCCAAAC | Example 4 |
| 62. | cChr13-R2 | CTCTTCCCCACCATGTGTTCATTCATTC | Example 4 |
| 63. | cChr13-E3 | AACCCCGTACAAAATCGCCACCACCAACTCCTCTAGCATTAATAGTTACCACACCTC | Example 4 |
| 64. | cChr13-R3 | TACTGACCAATCCAATGTCAAATTCCTCTACCAC | Example 4 |
| 65. | cChr13-E4 | AACCCCGTACAAAATCGCCACCACCAACAAACCCCAATGCCCAAATCTTGCCATTTTTTCAC | Example 4 |
| 66. | cChr13-R4 | TACCCTTCCTTCCCTGAACACAGTCAATCATTTCTC | Example 4 |
| 67. | cChr13-F5 | AACCCCGTACAAAATCGCCACCACCAACCTCTGCCCTCACGACCCAATCACCTTTCAAAC | Example 4 |
| 68. | cChr13-RS | CCTCCAAAACTCATCTGGAAATTTATTCCCCCAC | Example 4 |
| 69. | Pr1 | FAM-AGGAGTTCCTATCCGGCCTTCCATATCACCCCTCACTCCT | Example 4 |
| 70. | Pr2 | FAM-AGGAGTACCACTCTTCCTCAGAAGATATCCTTCCACTCCT | Example 4 |
| 71. | Pr3 | HEX-AGGAGTAACCCCGTACAAAATCGCCACCACCAACACTCCT | Example 4 |

What is claimed is:

1. A method of performing a digital amplification on a target nucleic acid in a sample comprising:
   partitioning a sample comprising a target nucleic acid into aliquots,
   conducting amplification reactions in the aliquots, wherein an amplified segment of the target nucleic acid is formed by extension of a pair of forward and reverse primers on the target nucleic acid if the target nucleic acid is present in the aliquot; wherein
   the primers are underrepresented in one or more of the four standard nucleotide types, the underrepresented nucleotide type(s) being the same in the primers, wherein an underrepresented nucleotide type is present at up to 2 internal positions, and optionally at a 5' terminal position, of each of the forward primer and the reverse primer, and wherein the 3' position of the forward primer and the 3' position of the reverse primer are occupied by the complement of an underrepresented nucleotide type; and
   detecting an amplified segment, if present, in each aliquot.

2. The method of claim 1, further comprising determining the copy number of the target nucleic acid from the number of aliquots containing the amplified segment.

3. The method of claim 1, wherein the target nucleic acid is cell-free DNA.

4. The method of claim 1, wherein the sample is a tissue or a body fluid.

5. The method of claim 1, wherein the amplification reactions in the aliquots are polymerase chain reactions.

6. The method of claim 1, wherein the target nucleic acid is treated with bisulfite to determine the methylation state of the target nucleic acid.

7. The method of claim 1, wherein the detecting indicates whether a predefined genetic abnormality is present in the target nucleic acid.

8. The method of claim 7, wherein the predefined genetic abnormality is a chromosome aneuploidy, single nucleotide polymorphism (SNP), insertion, or deletion.

9. The method of claim 8, wherein the chromosome aneuploidy is trisomy 21, trisomy 18, trisomy 13, triple X, or monosomy X.

10. The method of claim 9, wherein a chromosome aneuploidy is determined based on absolute quantifications of copy numbers of target nucleic acids on two chromosomes, one of which is subject to the aneuploidy and the other of which is not.

11. The method of claim 9, performed on a plurality of target nucleic acids including a target nucleic acid from chromosome 21, a target nucleic acid from chromosome 18 and a target nucleic acid from chromosome 13, wherein the detecting indicates one of the target nucleic acids includes the aneuploidy.

12. The method of claim 9, performed on samples from a population, wherein the method identifies samples containing the chromosome aneuploidy, chromosomes lacking the aneuploidy and inconclusive samples, and the method further comprising sequencing DNA from the inconclusive samples to determine whether the samples determined to be inconclusive by the digital amplification analysis have the chromosome aneuploidy.

13. The method of claim 1, wherein the sample is a cell-free nucleic acid sample.

14. The method of claim 13, wherein the cell-free nucleic acid sample is from a pregnant female and the target nucleic is a fetal nucleic acid.

15. The method of claim 14, wherein the fetal nucleic acid is a segment of the Y-chromosome or encoded by the Y-chromosome.

16. The method of claim 14, wherein the fetal nucleic acid is differentially methylated compared with a corresponding maternal nucleic acid.

17. The method of claim 13, performed with a plurality of target nucleic acids which include a fetal nucleic acid target and a corresponding maternal target nucleic acid.

18. The method of claim 13, performed with a plurality of target nucleic acids which include a genomic target released by lysed blood cells and a cell-free target nucleic acid.

19. The method of claim 13, wherein the amplification is droplet digital PCR (ddPCR).

20. The method of claim 1, wherein the amplified segment is detected with an intercalating dye.

21. The method of claim 1, wherein the amplified segment is detected with a fluorophore-labeled oligonucleotide probe.

22. The method of claim 1, further comprising fragmenting the target nucleic acid before performing the digital amplification.

23. The method of claim 1, further comprising identifying primer binding sites for the forward and reverse primers with a computer programmed to search the target nucleic acid for primer binding sites underrepresented in the complement of the standard nucleotide type(s) underrepresented in the forward and reverse primers.

24. The method of claim 1, wherein the primers have one and only one underrepresented standard nucleotide type.

25. The method of claim 1, wherein the primers have one and only one underrepresented standard nucleotide type, and the underrepresented nucleotide type is present at the 5' terminal position of one of the primers.

26. The method of claim 1, performed in multiplex with a plurality of target nucleic acids and a pair of forward and reverse primers for each of the target nucleic acids.

27. The method of claim 26, wherein the underrepresented nucleotide type is present at up to 2 internal positions, and optionally at a 5' terminal position of each of the forward primer and the reverse primer pairs.

28. The method of claim 1, wherein the target nucleic acid is DNA.

29. The method of claim 1, wherein the target nucleic acid is RNA.

30. The method of claim 1, wherein the amplification reactions are isothermal reactions.

31. A method of performing a digital amplification on a target nucleic acid in a sample comprising:
   partitioning a sample comprising a target nucleic acid into aliquots,
   conducting amplification reactions in the aliquots, wherein an amplified segment of the target nucleic acid is formed by extension of a pair of forward and reverse primers on the target nucleic acid if the target nucleic acid is present in the aliquot; wherein
   the primers are underrepresented in one or more of the four standard nucleotide types, the underrepresented nucleotide type(s) being the same in the primers, the underrepresented nucleotide type(s) being present at two or fewer internal positions and/or the 5' end position;
   and detecting an amplified segment, if present, in each aliquot,
   wherein the sample comprises a plurality of target nucleic acids, and the amplification is performed with a plurality of forward and reverse primer pairs corresponding to the respective target nucleic acids, each of which is underrepresented in the same standard nucleotide type(s), optionally wherein the pluralities are each at least 2, 3, 4, 5, 6, 7, 8, 9 or 10.

32. The method of claim 31, wherein each of the primer pairs is underrepresented in the same one and only one standard nucleotide type.

33. A method of performing a digital amplification on a target nucleic acid in a sample comprising:
   partitioning a sample comprising a target nucleic acid into aliquots,
   conducting amplification reactions in the aliquots, wherein an amplified segment of the target nucleic acid is formed by extension of a pair of forward and reverse primers on the target nucleic acid if the target nucleic acid is present in the aliquot; wherein
   the primers are underrepresented in one or more of the four standard nucleotide types, the underrepresented nucleotide type(s) being the same in the primers, the underrepresented nucleotide type(s) being present at two or fewer internal positions and/or the 5' end position;
   and detecting an amplified segment, if present, in each aliquot, wherein the forward primer and/or reverse primer is linked at its 5' end to an artificial sequence underrepresented in a nucleotide type, which is underrepresented in the forward and reverse primers.

* * * * *